United States Patent
Brownhill et al.

(10) Patent No.: US 12,178,597 B2
(45) Date of Patent: Dec. 31, 2024

(54) DEVICE, APPARATUS AND METHOD OF DETERMINING SKIN PERFUSION PRESSURE

(71) Applicant: Smith & Nephew PLC, Watford (GB)

(72) Inventors: Varuni Rachindra Brownhill, Hull (GB); Scott Grubb, Cambridge (GB); Allan Kenneth Frazer Grugeon Hunt, Beverley (GB); Reece Knight, Kingston upon Hull (GB); Peter Laitenberger, Cambridge (GB); Lee Partington, Hessle (GB); Marcus Damian Phillips, Wakefield (GB)

(73) Assignee: Smith & Nephew PLC, Watford (GB)

( * ) Notice: Subject to any disclaimer, the term of this patent is extended or adjusted under 35 U.S.C. 154(b) by 870 days.

(21) Appl. No.: 16/492,531

(22) PCT Filed: Mar. 9, 2018

(86) PCT No.: PCT/EP2018/055940
§ 371 (c)(1),
(2) Date: Sep. 9, 2019

(87) PCT Pub. No.: WO2018/162728
PCT Pub. Date: Sep. 13, 2018

(65) Prior Publication Data
US 2021/0137446 A1 May 13, 2021

(30) Foreign Application Priority Data

Mar. 9, 2017 (GB) .................................. 1703775
Mar. 9, 2017 (GB) .................................. 1703781
Mar. 9, 2017 (GB) .................................. 1703783

(51) Int. Cl.
*A61B 5/0255* (2006.01)
*A61B 5/00* (2006.01)
(Continued)

(52) U.S. Cl.
CPC .......... *A61B 5/445* (2013.01); *A61B 5/02255* (2013.01); *A61B 5/0261* (2013.01);
(Continued)

(58) Field of Classification Search
CPC ... A61B 5/445; A61B 5/02255; A61B 5/0261; A61B 5/6846; A61B 5/7282;
(Continued)

(56) References Cited

U.S. PATENT DOCUMENTS 3,896,802 A 7/1975 Williams
4,334,530 A 6/1982 Hassell
(Continued)

FOREIGN PATENT DOCUMENTS

CN 105232229 1/2016
CN 105395184 3/2016
(Continued)

OTHER PUBLICATIONS

"Little Miss Plasters", kidstravelclub.co.uk., accessed Aug. 26, 2016, in 2 pages. URL: http://www.kidstravelclub.co.uk/little-miss-girls-childrens-plasters.
(Continued)

*Primary Examiner* — Navin Natnithithadha
(74) *Attorney, Agent, or Firm* — Knobbe, Martens, Olson & Bear, LLP

(57) ABSTRACT

Disclosed embodiments relate to apparatuses and methods for a skin perfusion pressure determination device. In some embodiments, a skin perfusion pressure determination device can include a sensor module having a first sensor for sensing a first parameter associated with a pressure exerted on a target area by the sensor module and a second sensor for sensing a second parameter associated with an amount of blood perfusion at the target area. In some embodiments, the first sensor and the second sensor can be arranged such that,
(Continued)

when the sensor module is pressed against the target area the first sensor produces an output corresponding to the sensed first parameter and the second sensor produces an output corresponding to the sensed second parameter.

20 Claims, 47 Drawing Sheets

(51) Int. Cl.
    *A61B 5/0225*     (2006.01)
    *A61B 5/026*     (2006.01)
    *A61F 13/00*     (2006.01)
    *A61B 5/024*     (2006.01)
    *A61F 13/84*     (2006.01)

(52) U.S. Cl.
    CPC .......... *A61B 5/6843* (2013.01); *A61B 5/7282* (2013.01); *A61B 5/7405* (2013.01); *A61B 5/742* (2013.01); *A61B 5/7455* (2013.01); *A61F 13/00051* (2013.01); *A61B 5/02422* (2013.01); *A61B 5/0255* (2013.01); *A61F 2013/00089* (2013.01); *A61F 2013/8473* (2013.01)

(58) Field of Classification Search
    CPC ..... A61B 5/7405; A61B 5/742; A61B 5/7455; A61B 5/02422; A61B 5/0255; A61B 5/6843; A61B 5/02007; A61B 5/022; A61B 5/683; A61F 13/00051; A61F 2013/00089; A61F 2013/8473
    See application file for complete search history.

(56) References Cited

U.S. PATENT DOCUMENTS

| | | | |
|---|---|---|---|
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,014,611 B1 | 3/2006 | Geddes et al. |
| 7,077,832 B2 | 7/2006 | Fleischmann |
| 7,088,591 B2 | 8/2006 | Kishimoto et al. |
| 7,201,063 B2 | 4/2007 | Taylor et al. |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,838,717 B2 | 11/2010 | Haggstrom et al. |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | McAdams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,207,392 B2 | 6/2012 | Haggstrom et al. |
| 8,238,996 B2 | 8/2012 | Burnes |
| 8,241,231 B2 | 8/2012 | Bausewein et al. |
| 8,332,053 B1 | 12/2012 | Patterson et al. |
| 8,333,874 B2 | 12/2012 | Currie et al. |
| 8,366,692 B2 | 2/2013 | Weston |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | McAdams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,829,263 B2 | 9/2014 | Haggstrom et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,974,428 B2 | 3/2015 | Shuler et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,192,700 B2 | 11/2015 | Weston et al. |
| 9,204,806 B2 | 12/2015 | Stivoric et al. |
| 9,220,455 B2 | 12/2015 | Sarrafzadeh et al. |
| 9,226,402 B2 | 12/2015 | Hsu |
| 9,282,897 B2 | 3/2016 | Ross, Jr. et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 9,999,711 B2 | 6/2018 | Weston et al. |
| 10,004,643 B2 | 6/2018 | Luckemeyer et al. |
| 10,046,096 B2 | 8/2018 | Askem et al. |
| 10,080,524 B1 | 9/2018 | Xi |
| 10,086,117 B2 | 10/2018 | Locke et al. |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,201,644 B2 | 2/2019 | Haggstrom et al. |
| 10,207,031 B2 | 2/2019 | Toth |
| 10,209,213 B2 | 2/2019 | Kang et al. |
| 10,285,620 B2 | 5/2019 | Jung et al. |

(56) References Cited

U.S. PATENT DOCUMENTS

| | | |
|---|---|---|
| 10,288,590 B2 | 5/2019 | Hammond et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 11,229,553 B2 | 1/2022 | Chen et al. |
| 11,647,922 B2 | 5/2023 | Scherer |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0036690 A1 | 2/2003 | Geddes et al. |
| 2003/0036751 A1 | 2/2003 | Anderson et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0034293 A1 | 2/2004 | Kimball |
| 2004/0230132 A1 | 11/2004 | Shehada |
| 2005/0088832 A1 | 4/2005 | Su et al. |
| 2005/0240107 A1 | 10/2005 | Alfano et al. |
| 2005/0280531 A1 | 12/2005 | Fadem et al. |
| 2005/0281445 A1 | 12/2005 | Marcotte et al. |
| 2006/0052678 A1 | 3/2006 | Drinan et al. |
| 2006/0058690 A1 | 3/2006 | Bartnik et al. |
| 2006/0129039 A1 | 6/2006 | Lindner et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2006/0276700 A1 | 12/2006 | O'Neil et al. |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner, Jr. et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0268111 A1 | 10/2010 | Drinan et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0092958 A1 | 4/2011 | Jacobs |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | McKenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi et al. |
| 2012/0166680 A1 | 6/2012 | Masoud et al. |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0066172 A1 | 3/2013 | Kulcke |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1 | 10/2013 | Duesterhoft et al. |
| 2013/0274629 A1 | 10/2013 | Duesterhoft et al. |
| 2013/0317367 A1 | 11/2013 | Shuler |
| 2014/0012108 A1 | 1/2014 | McPeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | McGuin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. et al. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0236019 A1 | 8/2014 | Rahum |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0073271 A1* | 3/2015 | Lee ................ A61B 5/02007 600/475 |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0282748 A1 | 10/2015 | Hamaguchi et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad Maragheh |
| 2016/0022223 A1 | 1/2016 | Grundfest et al. |
| 2016/0029900 A1 | 2/2016 | LaPlante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | McQuilkin et al. |
| 2016/0074234 A1 | 3/2016 | Abichandi et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |

(56) References Cited

U.S. PATENT DOCUMENTS

| | | |
|---|---|---|
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0242331 A1 | 8/2016 | Park et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0346164 A1 | 12/2016 | Ward et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano et al. |
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cemasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0304510 A1 | 10/2017 | Askem et al. |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0003579 A1 | 1/2018 | Esposito et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribiero et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0128681 A1 | 5/2018 | Otsuka |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0001032 A1 | 1/2019 | Weston et al. |
| 2019/0021911 A1 | 1/2019 | Askem et al. |
| 2019/0038014 A1 | 2/2019 | Greer, Jr. et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0134280 A1 | 5/2019 | Toth |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2020/0147407 A1 | 5/2020 | Efremkin |
| 2020/0330258 A1 | 10/2020 | Hansen et al. |
| 2021/0212855 A1 | 7/2021 | Hansen et al. |

FOREIGN PATENT DOCUMENTS

| | | | |
|---|---|---|---|
| CN | 106102322 | 11/2016 | |
| DE | 10 2012 211015 | 1/2014 | |
| DE | 10 2013 013013 | 2/2015 | |
| EP | 2 422 757 | 2/2012 | |
| EP | 2 454 990 | 5/2012 | |
| EP | 2 565 630 | 3/2013 | |
| EP | 2 574 275 | 4/2013 | |
| EP | 1 734 858 | 7/2014 | |
| EP | 3 034 054 | 6/2016 | |
| EP | 3 231 478 | 10/2017 | |
| EP | 3 409 190 | 12/2018 | |
| EP | 3424417 A1 | 1/2019 | |
| EP | 3 499 510 | 6/2019 | |
| GB | 1476894 | 6/1977 | |
| GB | 2316171 | 2/1998 | |
| GB | 2563602 | 12/2018 | |
| JP | 2006280770 A | 10/2006 | |
| JP | 2009-225863 | 10/2009 | |
| KR | 10 2012 0119523 | 10/2012 | |
| KR | 101224629 B1 | 1/2013 | |
| KR | 10 2014 0024743 | 3/2014 | |
| KR | 10 2014 0058041 | 5/2014 | |
| KR | 10 2016 0071044 | 6/2016 | |
| KR | 20190105898 A | 9/2019 | |
| NL | 1 027 236 | 4/2006 | |
| WO | WO-9415531 A1 | 7/1994 | |
| WO | WO 2000/021433 | 4/2000 | |
| WO | WO 2000/043046 | 7/2000 | |
| WO | WO-0185024 A1 | 11/2001 | |
| WO | WO 2003/067229 | 8/2003 | |
| WO | WO 2006/041997 | 4/2006 | |
| WO | WO 2007/030379 | 3/2007 | |
| WO | WO 2008/006150 | 1/2008 | |
| WO | WO 2008/010604 | 1/2008 | |
| WO | WO 2009/052607 | 4/2009 | |
| WO | WO 2009/120951 | 10/2009 | |
| WO | WO 2009/141777 | 11/2009 | |
| WO | WO 2010/020919 | 2/2010 | |
| WO | WO 2010/105053 | 9/2010 | |
| WO | WO 2011/082420 | 7/2011 | |
| WO | WO 2011/113070 | 9/2011 | |
| WO | WO 2011/123848 | 10/2011 | |
| WO | WO 2012/141999 | 10/2012 | |
| WO | WO 2013/026999 | 2/2013 | |
| WO | WO 2013/044226 | 3/2013 | |
| WO | WO 2013/155193 | 10/2013 | |
| WO | WO 2014/036577 | 3/2014 | |
| WO | WO-2014094173 A1 | 6/2014 | |
| WO | WO-2014116816 A1 | 7/2014 | |
| WO | WO-2015047015 A1 * | 4/2015 | ........... A61B 5/0006 |
| WO | WVO 2015/112095 | 7/2015 | |
| WO | WO 2015/168720 | 11/2015 | |
| WO | WO 2016/025438 | 2/2016 | |
| WO | WO-2016022295 A1 | 2/2016 | |
| WO | WO 2016/030752 | 3/2016 | |
| WO | WO 2016/058032 | 4/2016 | |
| WO | WO-2016073777 A1 | 5/2016 | |
| WO | WO 2016/100218 | 6/2016 | |
| WO | WO 2016/109744 | 7/2016 | |
| WO | WO 2016/110564 | 7/2016 | |
| WO | WO 2016/187136 | 11/2016 | |
| WO | WO 2016/205872 | 12/2016 | |
| WO | WO 2016/205881 | 12/2016 | |
| WO | WO 2017/021006 | 2/2017 | |
| WO | WO 2017/021965 | 2/2017 | |
| WO | WO 2017/033058 | 3/2017 | |
| WO | WO 2017/037479 | 3/2017 | |
| WO | WO 2017/041014 | 3/2017 | |
| WO | WO 2017/041386 | 3/2017 | |
| WO | WO 2017/041387 | 3/2017 | |
| WO | WO-2017041385 A1 | 3/2017 | |
| WO | WO 2017/119996 | 7/2017 | |
| WO | WO 2017/205728 | 11/2017 | |
| WO | WO-2017201419 A1 | 11/2017 | |
| WO | WO 2017/214188 | 12/2017 | |
| WO | WO 2018/035612 | 3/2018 | |
| WO | WO 2018/060417 | 4/2018 | |

(56) References Cited

FOREIGN PATENT DOCUMENTS

| | | |
|---|---|---|
| WO | WO 2018/064569 | 4/2018 |
| WO | WO 2018/115461 | 6/2018 |
| WO | WO 2018/144938 | 8/2018 |
| WO | WO 2018/144941 | 8/2018 |
| WO | WO 2018/144943 | 8/2018 |
| WO | WO 2018/144946 | 8/2018 |
| WO | WO 2018/162728 | 9/2018 |
| WO | WO 2018/162732 | 9/2018 |
| WO | WO 2018/162735 | 9/2018 |
| WO | WO 2018/162736 | 9/2018 |
| WO | WO 2018/185138 | 10/2018 |
| WO | WO 2018/189265 | 10/2018 |
| WO | WO 2018/209090 | 11/2018 |
| WO | WO 2018/210692 | 11/2018 |
| WO | WO 2018/210693 | 11/2018 |
| WO | WO 2018/211458 | 11/2018 |
| WO | WO 2018/234443 | 12/2018 |
| WO | WO 2019/020550 | 1/2019 |
| WO | WO 2019/020551 | 1/2019 |
| WO | WO 2019/020666 | 1/2019 |
| WO | WO 2019/030384 | 2/2019 |
| WO | WO 2019/048624 | 3/2019 |
| WO | WO 2019/048626 | 3/2019 |
| WO | WO 2019/048638 | 3/2019 |
| WO | WO 2019/063481 | 4/2019 |
| WO | WO 2019/063488 | 4/2019 |
| WO | WO 2019/067264 | 4/2019 |
| WO | WO 2019/072531 | 4/2019 |
| WO | WO 2019/076967 | 4/2019 |
| WO | WO 2019/096828 | 5/2019 |
| WO | WO 2019/140441 | 7/2019 |
| WO | WO 2019/140444 | 7/2019 |
| WO | WO 2019/140448 | 7/2019 |
| WO | WO 2019/140449 | 7/2019 |

OTHER PUBLICATIONS

Aubakir, B. et al., "Vital Sign Monitoring Utilizing Eulerian Video Magnification and Thermography", 2016 38th Annual International Conference of the IEEE Engineering in Medicine and Biology Society, Aug. 16, 2016, pp. 3527-3530, in 4 pages.

Bandodkar, A. et al., "Battery-free, skin-interfaced microfluidic/electronic systems for simultaneous electrochemical, colorimetric, and volumetric analysis of sweat", Science Advances, vol. 5(1), Jan. 18, 2019, in 16 pages. URL: http://advances.sciencemag.org/content/5/1/eaav3294.

Cauwe, M. et al., "Technology development for a low-cost, roll-to-roll chip embedding solution based on PET foils", 18th European Microelectronics and Packaging Conference (EMPC), IEEE, Sep. 12, 2011, in 6 pages.

Farooqui, M. et al., "Low Cost Inkjet Printed Smart Bandage for Wireless Monitoring of Chronic Wounds", Scientific Reports, vol. 6, Jun. 29, 2016, in 14 pages.

Geng, Y. et al., "A Hybrid Low Power Biopatch for Body Surface Potential Measurement", IEEE Journal of Biomedical and Health Informatics, vol. 17(3), May 1, 2013, XP011506375.

Great Britain Office Action and Search Report, re GB Application No. 1703775.5, dated Aug. 2, 2017.

Great Britain Office Action and Search Report, re GB Application No. 1703781.3, dated Aug. 14, 2017.

Great Britain Office Action and Search Report, re GB Application No. 1703783.9, dated Aug. 22, 2017.

Great Britain Office Action, re GB Application No. 1814814.8, dated Mar. 8, 2019.

Great Britain Office Action, re GB Application No. 1814872.6, dated Mar. 13, 2019.

Iannetta, R.A. et al., "Successful case histories of polymer based circuitry on flexible film substrates", Electro/94 International Conference Proceedings Combined vols. IEEE, May 10-12, 1994, XP010149465.

Invitation to Pay Additional Fees and Partial Search Report, re PCT Application No. PCT/EP2018/055940, mailed Jun. 12, 2018.

International Search Report and Written Opinion, re PCT Application No. PCT/EP2019/074254, mailed Dec. 5, 2019.

Jinto, G. et al., "Reliability of Plastic-Encapsulated Electronic Components in Supersaturated Steam Environments", IEEE Transactions on Components, Packaging, and Manufacturing Technology, vol. 5, No. 10, Oct. 2015, in 9 pages.

Lu, B. et al., "A study of the autofluorescence of parylene materials for [mu]TAS applications", Lab on Chip, vol. 10, No. 14, Jul. 2010, pp. 1826-1834, in 9 pages.

Mcleod, A. et al., "Motion Magnification for Endoscopic Surgery", Progress in Biomedical Optics and Imaging, SPIE—International Society for Optical Engineering, Mar. 12, 2014, vol. 9036, in 8 pages.

Mostafalu, P. et al., "Wireless Flexible Smart Bandage for Continuous Monitoring of Wound Oxygenation", IEEE Transactions on Biomedical Circuits and Systems, vol. 9, No. 5, Oct. 2015, pp. 670-677, in 8 pages.

Narusawa, H., "The corona discharge causes short destruction that had bad influence on a power switching circuit", Adphox Corporation, Jan. 1, 2009, in 12 pages. URL: http://www.adphox.co.jp/keisokuki/ke-english-corona/CORONA_DISCHARGE_EN.pdf.

Raviglione, A. et al., "Real-Time Smart Textile-Based System to Monitor Pressure Offloading of Diabetic Foot Ulcers", Journal of Diabetes Science and Technology, vol. 11, Sep. 2017, in 5 pages.

Rose, D. et al., "Adhesive RFID Sensor Patch for Monitoring of Sweat Electrolytes", IEEE Transactions on Biomedical Engineering, vol. 62(6), Jun. 2015 (first published Nov. 11, 2015), in 9 pages.

Wakita, J. et al., "Variations in Optical Absorption and Fluorescence Spectra for Polyimide Thin Films Caused by Structural Isomerism", J. Photopolym. Sci. Technol. Jan. 1, 2003, in 1 page.

Willis, B., "Conformal Coating Inspection & Coating Faults", Vision Engineering, Jul. 21, 2016, in 35 pages. URL: http://www.visioneng.com/wp-content/uploads/2017/11/Confirmal-Coating-Inspection-and-Defects.21JUL16.pdf.

Willis, B., "Guide to Conformal Coating & Cleaning Defects Contents", Mar. 1, 2014, in 31 pages. URL: http://coatingguide.smartgroup.org/Files%20pdf/Coating%20Defects%20V2%2014March2014.pdf.

International Search Report and Written Opinion, re PCT Application No. PCT/EP2018/055940, mailed Sep. 3, 2018.

Hu F., et al., "Intelligent Sensor Networks: The Integration of Sensor Networks, Signal Processing and Machine Learning," 2013, Auberach Publications, pp. 3-5.

International Preliminary Report on Patentability and Written Opinion for Application No. PCT/EP2019/074254, mailed on Mar. 25, 2021, 10 pages.

International Preliminary Report on Patentability for Application No. PCT/EP2018/055940, mailed on Sep. 19, 2019, 9 pages.

Mehmood N., et al., "Applications Of Modern Sensors And Wireless Technology In Effective Wound Management: Modern Sensors And Wireless Technology," Journal of Biomedical Materials Research Part B, vol. 102, May 1, 2014, XP055739544, pp. 885-895.

* cited by examiner

DEVICE, APPARATUS AND METHOD OF DETERMINING SKIN PERFUSION PRESSURE

CROSS-REFERENCE TO RELATED APPLICATIONS

This application is a U.S. national stage application of International Patent Application No. PCT/EP2018/055940, filed Mar. 9, 2018, which claims priority to Patent Application No. GB 1703775.5, filed on Mar. 9, 2017, Patent Application No. GB 1703781.3, filed Mar. 9, 2017, and Patent Application No. GB 1703783.9, filed Mar. 9, 2017. All of these applications are hereby incorporated by reference in their entireties and made part of this disclosure.

FIELD

Embodiments described herein relates to a skin perfusion pressure determination device, apparatus and method of determining skin perfusion pressure.

BACKGROUND

Wound healing is natural process performed by the human body in response to injury. The amount of time taken for a wound to heal is dependent on many different factors which include the human body's ability to heal itself and any treatments that are applied to the wound to accelerate wound healing. Understanding the healing status of a wound and being able to monitor the healing process helps to inform decisions on further treatment of the wound and can also assist in the development of future wound therapies.

One factor that is known to be correlated with wound healing is the Skin Perfusion Pressure (SPP) in tissue adjacent the wound. SPP is the amount of pressure required to restore blood flow to blood vessels within skin tissue following a controlled occlusion of the blood vessels using a blood pressure cuff.

Techniques for detecting the restoration of blood flow include radioisotope clearance, laser doppler flow measurement and photoplethysmography. Such techniques are typically performed by clinicians and require instrumentation that is often bulky, complicated and expensive.

Additionally, a wound dressing is typically applied to a wound in order to protect the wound from pathogens, assist healing of the wound and to protect the area of the wound from further injury. In order to assess healing, the tissue in and around the wound may be inspected periodically. Inspection can be carried out by a clinician using the naked eye, but may also be carried out using optical devices that analyze the appearance of the wounded area to determine the state of the wound. To access the wounded area, the wound dressing must be removed. This is time consuming, inconvenient and often uncomfortable for the patient. Moreover, the original dressing is usually replaced by a fresh dressing even though the old dressing may not have needed replacing at the time of inspection In order to assess healing, a probe or other form of inspection device may be used to measure a parameter associated with wound healing at various points about the perimeter of the wound dressing. One example is the measurement of the amount of blood perfusion in the tissue surrounding the wound. The amount of blood perfusion will, however, vary about the periphery of the wound dressing. For example, the amount of blood perfusion of tissue at the periphery of a wound to a forearm may be greater in tissue closer to the elbow than in tissue closer to the wrist. Repeated measurements at different locations by clinicians can therefore produce results which are inconsistent and unreliable for determining the status of the healing process.

SUMMARY

It is an aim of the embodiments described herein to at least partly mitigate the above-mentioned problems.

It is an aim of certain embodiments to provide a skin perfusion pressure determination device, apparatus and a method of determining skin perfusion pressure for determining skin perfusion pressure at a target area.

Additionally, certain embodiments include a wound dressing which facilitates convenient inspection of the area of a wound without the inspection process being time consuming or uncomfortable for the patient.

Certain embodiments can provide a wound dressing which can be applied to a patient's wound in a predetermined orientation such that inspection of skin tissue in the vicinity of the wound can be conducted reliably, consistently and repeatedly.

Embodiments of the present disclosure relate to apparatuses and methods for wound treatment. Embodiments of the present disclosure provide a skin perfusion pressure determination device, apparatus and a method of determining skin perfusion pressure for determining skin perfusion pressure at a target area.

According to a some embodiments, there is provided a skin perfusion pressure determination device comprising a sensor module having a first sensor for sensing a first parameter associated with a pressure exerted on a target area by the sensor module and a second sensor for sensing a second parameter associated with an amount of blood perfusion at the target area, wherein the first sensor and the second sensor are arranged such that, when the sensor module is pressed against the target area the first sensor produces an output corresponding to the sensed first parameter and the second sensor produces an output corresponding to the sensed second parameter.

The first sensor may comprise a force sensor arranged to determine the force exerted by the sensor module on the target area.

The force sensor may be arranged such that when the sensor module is pressed against the target area, the second sensor is disposed between the target area and the force sensor.

The second sensor may comprise a light source and an optical detector arranged to receive light emitted by the light source which has been reflected by the target area.

The light source may comprise at least one light emitting diode and the optical detector comprises at least one photodetector. The second sensor may be a pulse sensor.

The device may be a portable device comprising a probe portion. The probe portion may comprise the sensor module.

The probe portion may comprise a pad portion having a lower surface which, in use, is pressed against the target area.

The device may be a portable device comprising a cuff portion for wrapping about a limb of a patient, the sensor module is arranged on an inner portion of the cuff.

The cuff may be inflatable. The cuff may be configured such that inflation of the cuff presses the sensor module against the target area.

The cuff may be manually actuated. The cuff may be configured to be inflated by an electromechanical actuator or fluid-based inflation device.

The device may comprise a wound dressing. The sensor module may be integral with the wound dressing.

The wound dressing may comprise an actuator arranged to press the sensor module against the target area.

The skin perfusion pressure determination device may further comprise a processor for processing an output of the first sensor and an output of the second sensor. The processor may be configured to determine that the output of the second sensor satisfies a predetermined condition associated with a predetermined amount of blood perfusion at the target area.

The predetermined condition may be a condition which corresponds to an amount of blood perfusion at the target area which exceeds a predetermine threshold.

The predetermined condition may be a condition that corresponds to the presence of a pulsatile component of blood flow at the target area.

The processor may be configured to produce an output which represents a pressure exerted on the target area by the sensor module when the second parameter satisfies the predetermined condition.

The skin perfusion pressure determination device may further comprise a memory for storing at least one of the predetermined condition and the output of the processor.

According to some embodiments, there is provided apparatus comprising the skin perfusion pressure determination device of the first aspect of the disclosure, wherein the apparatus comprises a display for displaying information representing at least one output of the first sensor and the second sensor.

According to some embodiments, there is provided a method of determining skin perfusion pressure comprising the steps: pressing a sensor module against a target area, wherein the sensor module has a first sensor for sensing a first parameter associated with a pressure exerted on a target area by the sensor module and a second sensor for sensing a second parameter associated with an amount of blood perfusion at the target area; subsequently reducing the pressure exerted on the target area by the sensor module; processing with a processor a first sensor output corresponding to the sensed first parameter and a second sensor output corresponding to the sensed second parameter to determine that the output of the second sensor satisfies a predetermined condition corresponding to an amount of blood perfusion at the target area and outputting an output from the processor which corresponds to the pressure exerted by the sensor module on the target area when the second parameter satisfies the predetermined condition.

The predetermined condition may be a condition which corresponds to an amount of blood perfusion at the target area which exceeds a predetermined threshold.

The predetermined condition may be a condition that corresponds to the presence of a pulsatile component of blood flow at the target area.

The step of reducing the pressure exerted by the sensor module on the target area may comprise the steps of: processing with the processor the second sensor output to determine that the second parameter satisfies a further predetermined condition associated with an amount of blood perfusion at the target area and subsequently reducing the pressure exerted by the sensor module on the target area.

The further predetermined condition may be a condition which corresponds to an amount of blood perfusion at the target area which is below a predetermined threshold.

According to some embodiments, there is provided a method of determining skin perfusion pressure comprising the steps: processing with a processor a first sensor output representing a sensed first parameter associated with a pressure applied to a target area and a second sensor output representing a sensed second parameter associated with an amount of blood perfusion at the target area to determine that the output of the second sensor satisfies a predetermined condition associated with an amount of blood perfusion at the target area and outputting an output from the processor which corresponds to the pressure exerted by the sensor module on the target area when the second parameter satisfies the predetermined condition.

The predetermined condition may be a condition which corresponds to an amount of blood perfusion at the target area which exceeds a predetermined threshold.

The predetermined condition may be a condition that corresponds to the presence of a pulsatile component of blood flow at the target area.

The method may further comprise the steps of: processing with the processor the second sensor output to determine that the second parameter satisfies a further predetermined condition associated with an amount of blood perfusion at the target area and subsequently reducing the pressure exerted by the sensor module on the target area.

The further predetermined condition may be a condition which corresponds to an amount of blood perfusion at the target area which is below a predetermined threshold.

Certain embodiments of the present disclosure allow a parameter associated with the amount of blood perfusion in skin tissue to be measured at the same location at which a pressure to occlude blood vessels in the skin is applied during measurement of skin perfusion pressure. An accurate measurement of skin perfusion pressure can therefore be determined at the location at which the pressure is applied.

Certain embodiments of the present disclosure allow for blood perfusion pressure to be determined using a device comprising a single sensor module for sensing parameters associated with applied pressure to a target area and the amount of blood perfusion at the target area simultaneously. The device can therefore be made compact, portable and easy to operate.

According to some embodiments, there is provided a wound dressing comprising:

a wound protecting portion which, in use, overlies a wound, and a peripheral portion which extends around at least part of the wound protecting portion, wherein the peripheral portion comprises at least one window which is arranged to locate a measurement probe having an optical sensor configured to sense light at a predetermined wavelength, wherein the window is transparent to light at the predetermined wavelength.

The predetermined wavelength may be a wavelength that corresponds to visible, ultraviolet or infrared light.

The predetermined wavelength may be between 495 nm and 1350 nm. In particular, the predetermined wavelength may be between 650 nm and 1350 nm.

The or each window may comprise an opening through the peripheral portion. The or each window may comprise an optically transparent material.

The optically transparent material may comprise at least one of polyvinyl chloride (PVC), cellulose acetate or acrylic or silicone or polyurethane or acylate.

The peripheral portion may have a lower surface and an adhesive on the lower surface for securing the wound dressing to a patient's skin.

The wound dressing may be an island-type dressing in which the wound protecting portion is disposed centrally and the peripheral portion extends around a perimeter of the wound protecting portion.

The peripheral portion may further comprise at least one lobe which projects away from the wound protecting portion, wherein the or each window is provided at least partially in the or each lobe respectively. The or each window may be circular or ovoid.

The wound dressing may comprise at least two windows adjacent the wound protecting portion. The wound protecting portion may be disposed between the windows.

The wound protecting portion may have four sides and the four windows which are disposed adjacent each of the sides respectively.

According to some embodiments, there is provided apparatus comprising: the wound dressing and a measurement probe comprising an optical sensor configured to sense light at the predetermined wavelength.

The measurement probe may comprise a pad portion having a lower surface which, in use, is pressed against a patient's skin, and the window has a size and shape which corresponds to the size and shape of the pad portion.

According to some embodiments, there is provided a method of sensing at least one characteristic associated with a wound or a region of tissue proximate to a wound, comprising the steps of: locating a wound dressing comprising a wound protecting portion over a wound whereby the wound protecting portion overlies the wound, locating a pad portion of a measurement probe at a window region of a peripheral portion of the wound dressing, and transmitting light from the measurement probe through the window.

The method may further comprise preventing light from the measurement probe penetrating through the wound dressing at remaining regions of the wound dressing away from the window.

The method may further comprise: one-by-one, locating the measurement probe consecutively at each of a plurality of windows on the wound dressing and taking respective probe measurements at each location.

Certain embodiments of the present disclosure allow for consistent inspection of a region of tissue at or proximate a wound using a measurement probe.

Certain embodiments of the present disclosure allow for repeated measurements at a region of tissue at or proximate a wound to be made at one or more predetermined locations by a measurement probe such that a record of measurements associated with wound healing can be compiled for each of the predetermined locations.

Certain embodiments of the present disclosure allow for inspection of a region of tissue at or proximate a wound without having to remove a wound dressing.

According to some embodiments, there is provided a wound dressing comprising an upper surface, and at least one indicium for determining the orientation of the wound dressing, about an axis which is orthogonal to the upper surface, relative to a surface on which the wound dressing is securable.

At least one indicium may be provided on the upper surface.

The wound dressing may comprise a wound protecting portion; and a peripheral portion which extends around at least part of the wound contacting portion, wherein the wound protecting portion comprises the at least one indicium.

The peripheral portion may have a lower surface and an adhesive on the lower surface for securing the wound dressing to a surface.

A plurality of indiciums may be provided on the upper surface. Each indicium may comprise at least one graphical marker which is different from each of the other graphical markers.

The wound dressing may have at least two poles and at least one graphical marker may be provided at each of the poles. Each marker may comprise an alphanumeric character. Each marker may comprise a directional marker.

The wound dressing may be an island-type dressing.

Each indicium may be a printed element or a recessed region or a protruding region of the wound dressing. Each indicium may comprise at least one of a color patch, a metal element, a magnetic element and a resonant tag. Each indicium may comprise an RFID tag.

The wound dressing may further comprise a least one sensor site and said at least one indicium provides a visible cue for locating the sensor site at a desired location with respect to a wound. Each sensor site may be associated with a respective at least one indicium.

Each sensor site may comprise a location where a wound dressing sensor is located, a location of a window configured to receive a portion of a probe portion of an inspection device, or a target area of the wound dressing configured to receive a portion of a probe portion of an inspection device.

Each indicium may comprise of an RFID tag and a graphical marker which are configured to be uniquely associated with a respective sensor site of the wound dressing.

According to some embodiments, there is provided a method of orientating a wound dressing to a desired orientation with respect to a surface, comprising the steps of: locating a wound dressing proximate to a wound, rotating the wound dressing about an axis orthogonal to an upper surface of the wound dressing to align at least one indicium on the upper surface at a desired rotatory orientation, and urging the wound dressing towards the wound thereby dressing the wound via the wound dressing.

The method may further comprise rotating the wound dressing to align at least one indicium on a peripheral portion of the wound dressing at a desired positional relationship with respect to a wound or a predetermined patient feature.

The method may further comprise the wound dressing further comprising at least one sensor site and the step of rotating the wound dressing comprises locating each sensor site at a desired location with respect to the wound.

The step of locating each sensor site may comprise locating a wound dressing sensor at the desired location or at a window portion of the wound dressing that locates a wound dressing sensor.

Certain embodiments of the present disclosure allow inspection of skin tissue in the vicinity of the wound to be conducted reliably, consistently and repeatedly.

Certain embodiments of the present disclosure allow for measurements of a parameter associated with wound healing to be compiled for specific locations in the vicinity of a wound such that progress of wound healing can be monitored accurately over a desired period of time.

According to some embodiments, there is provided a wound dressing comprising an upper surface; and at least one indicium for determining the orientation of the wound dressing, about an axis which is orthogonal to the upper surface, relative to a surface on which the wound dressing is securable; a wound protecting portion; and a peripheral portion which extends around at least part of the wound contacting portion, wherein the wound protecting portion comprises the at least one indicium, wherein a plurality of indiciums are provided on the upper surface, each indicium comprising at least one graphical marker which is different from each of the other graphical markers.

According to some embodiments, there is provided a wound dressing comprising: an upper surface; at least one indicium for determining the orientation of the wound dressing, about an axis which is orthogonal to the upper surface, relative to a surface on which the wound dressing is securable; a wound protecting portion; and a peripheral portion which extends around at least part of the wound contacting portion, wherein the wound protecting portion comprises the at least one indicium.

According to some embodiments, there is provided a wound dressing comprising an upper surface and at least one indicium for determining the orientation of the wound dressing, about an axis which is orthogonal to the upper surface, relative to a surface on which the wound dressing is securable, wherein each indicium comprises an RFID tag.

According to some embodiments, there is provided a wound dressing comprising an upper surface; at least one indicium for determining the orientation of the wound dressing, about an axis which is orthogonal to the upper surface, relative to a surface on which the wound dressing is securable; at least one sensor site, wherein said at least one indicium provides a visible cue for locating the sensor site at a desired location with respect to a wound, and wherein each indicium comprises of an RFID tag and a graphical marker which are configured to be uniquely associated with a respective sensor site of the wound dressing.

According to some embodiments, there is provided an apparatus comprising a wound dressing; a skin perfusion pressure determination device comprising a sensor module, the sensor module including a sensor configured to sense at least one characteristic associated with a wound or a region of tissue proximate to a wound; and a display configured to indicate at least one condition relating to the at least one characteristic associated with a wound or a region of tissue proximate to a wound sensed by the sensor module.

The skin perfusion pressure determination device can comprise a hand-held device.

The display can comprise a computer monitor, laptop, tablet, or smart phone.

The display can be configured to provide a visual indication of a measurement location, an applied force, an occlusion reached indication, high force warning, speed of movement indication, perfusion measurement result, or a measurement quality indication.

The display can be positioned on the skin perfusion pressure determination device.

The display can comprise one or more visual indicators.

The one or more visual indicators can comprise a multi-segment gauge type indicator, a symbol, a text and/or numeric indication, graphical indication, or circumferential indicators.

The one or more visual indicators can comprise one or more light emitting diodes (LED).

The one or more visual indicators can comprise an LED indicator, organic light emitting diodes (OLED) indicator, and/or EINK indicators.

The one or more visual indicators can comprise a multi-segment gauge type indicator, a symbol, a text and/or numeric indication, graphical indication, or circumferential indicators.

The sensor module can be configured to apply a pressure on a target area.

The sensor module can comprise a first sensor for sensing a first parameter associated with the pressure exerted on the target area by the sensor module and a second sensor for sensing a second parameter associated with an amount of blood perfusion at the target area.

The display can be configured to provide user instructions to increase the applied pressure or to reduce the applied pressure during a measurement process.

According to some embodiments, there is provided an apparatus comprising a wound dressing, a skin perfusion pressure determination device comprising a sensor module, the sensor module including a sensor configured to sense at least one characteristic associated with a wound or a region of tissue proximate to a wound, and an audible and/or tactile indicator configured to indicate at least one condition relating to the at least one characteristic associated with a wound or a region of tissue proximate to a wound sensed by the sensor module.

According to some embodiments, there is provided a method of determining at least one characteristic associated with a wound or a region of tissue proximate to a wound comprising: locating a wound dressing comprising a wound protecting portion over a wound whereby the wound protecting portion overlies the wound; positioning a skin perfusion pressure determination device comprising a sensor module at a target area on or adjacent to the wound dressing, wherein the sensor module includes a sensor configured to detect at least one characteristic associated with a wound or a region of tissue proximate to a wound; and receiving a visual, audible, or tactile indicator relating to the at least one characteristic associated with a wound or a region of tissue proximate to a wound detected with the sensor of the skin perfusion pressure determination device.

A visual indicator can be incorporated into a display.

The skin perfusion pressure determination device can comprise a hand-held device.

The display can comprise a computer monitor, laptop, tablet, or smart phone.

The skin perfusion pressure determination device can comprise the visual, audible, or tactile indicators.

The display can comprise one or more visual indicators.

A visual indicator can comprise one or more light emitting diodes (LED).

A visual indicator can comprise an LED indicator, organic light emitting diodes (OLED) indicator, and/or EINK indicator.

A visual indicator can comprise a multi-segment gauge type indicator, a symbol, a text and/or numeric indication, graphical indication, or circumferential indicators.

The at least one characteristic associated with a wound or a region of tissue proximate to a wound can comprise a skin perfusion pressure.

The method can further comprise applying pressure to the skin perfusion pressure determination device to exert a pressure on a target area.

The sensor module can have a first sensor for sensing a first parameter associated with the pressure exerted on the target area by the sensor module and a second sensor for sensing a second parameter associated with an amount of blood perfusion at the target area.

The visual, audible, or tactile indicator can provide user instructions to increase the applied pressure or to reduce the applied pressure of the skin perfusion pressure determination device on the target area.

The visual, audible, or tactile indicator can provide an indication of a measurement location, an applied force, an occlusion reached indication, high force warning, speed of movement indication, perfusion measurement result, or a measurement quality indication.

BRIEF DESCRIPTION OF THE DRAWINGS

Embodiments of the present disclosure will now be described, by way of example only, with reference to the accompanying drawings in which.

DETAILED DESCRIPTION

Figure 1:
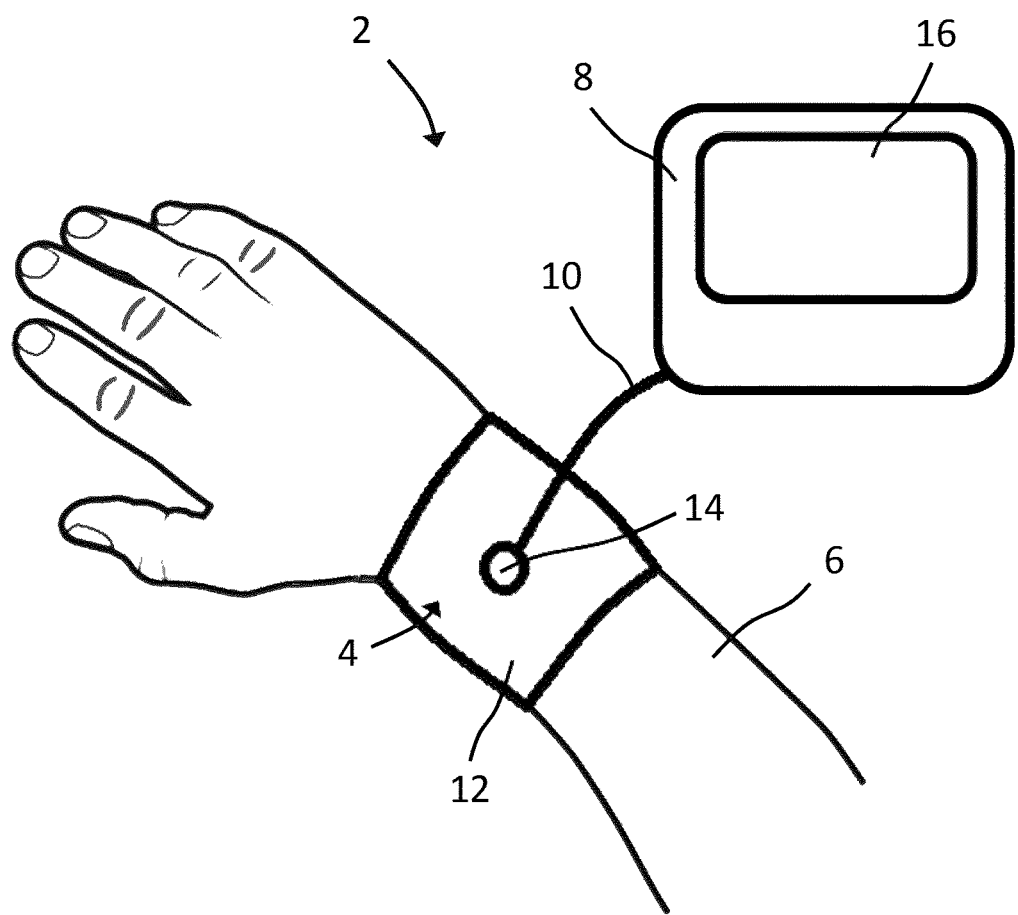
FIG. 1 is a schematic representation of a skin perfusion pressure determination device in use.

FIG. 1 shows an apparatus 2 for determining skin perfusion pressure comprising a skin perfusion pressure determination device 4 secured to a patient's arm 6 and a monitoring device 8 connected via a lead 10 to the skin perfusion pressure determination device 4. The skin perfusion pressure determination device 4 comprises a wound dressing 12 and a sensor module 14 formed integrally with the wound dressing 12. The wound dressing 12 is in the form of a detachable band that may be secured to the arm 6 of the patient by wrapping it around the arm 6 and securing opposite end portions together using a fastener, such as an adhesive strip or hook and loop fastener or the like. In other embodiments the skin perfusion pressure determination device may be a detachable band that does not comprise a wound dressing but may be secured adjacent a wound if desired. Bands may be secured to other parts of an animal or person's body including other limbs, such as a leg, or a torso. The lead 10 is connected to the sensor module 14 at one end and to the monitoring device 8 at the other end. The lead 10 provides a means for communication between the sensor module 14 and the monitoring device 8 and also provides a means for supplying power to the sensor module 14.

The monitoring device 8 is configured to receive and process a signal received from the sensor module 14 and display processed information on an integrated display 16.

Figure 2:
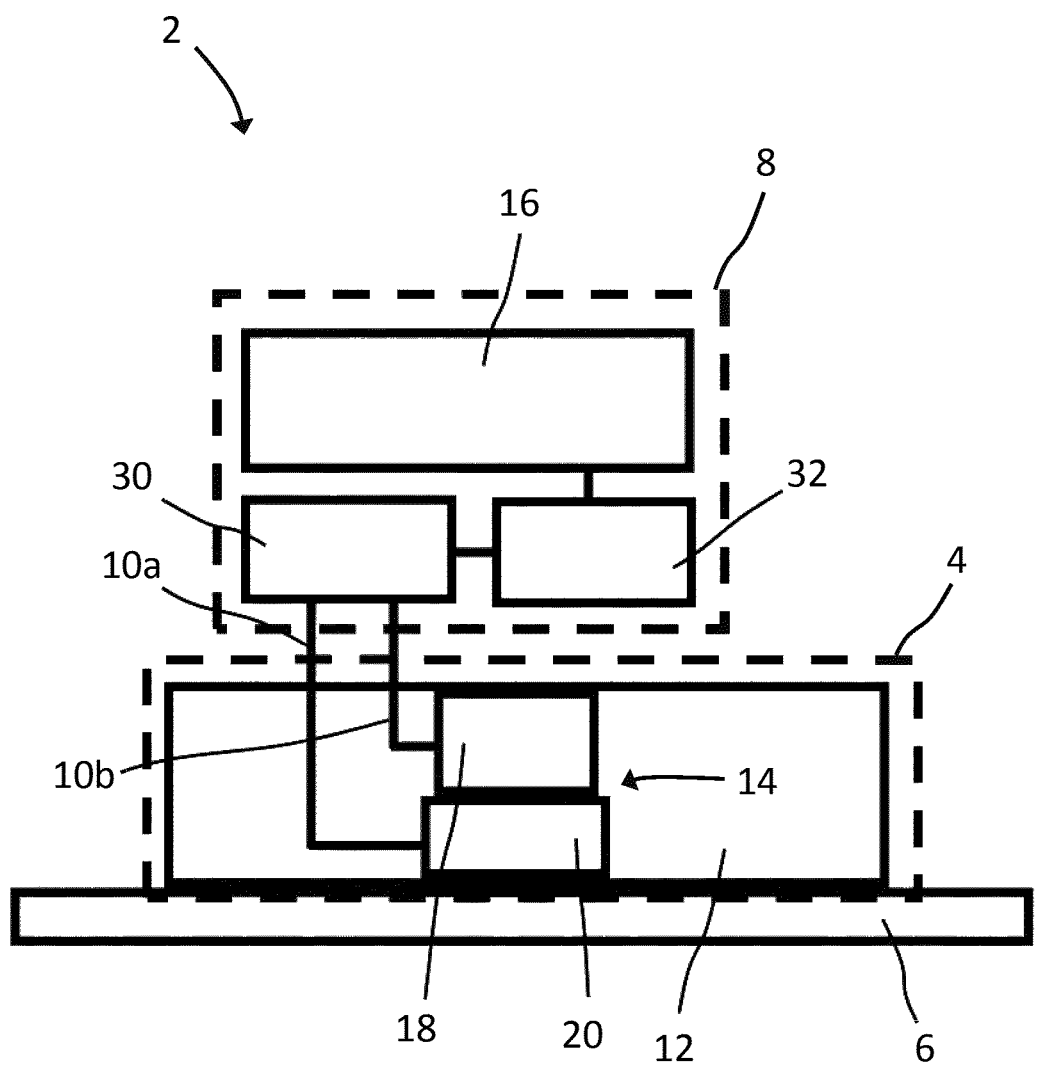
FIG. 2 is a schematic representation of components of the skin perfusion pressure determination device shown in FIG. 1.

FIG. 2 is a system diagram representing components of the apparatus 2 shown in FIG. 1.

FIG. 2 depicts components of the skin perfusion pressure determination device 4 and the monitoring device 8 which are enclosed, respectively, by broken lines. The sensor module 14 comprises a first sensor in the form of a force sensor 18 for sensing a force transmitted through the sensor module 14 to the patient's arm 6, and a second sensor in the form of an optical sensor 20 for sensing a parameter which corresponds to the amount of blood perfusion in the skin tissue of the arm 6 underneath the sensor module 14. In the present embodiment, the optical sensor 20 is a pulse sensor, but other suitable sensors may be used such as a reflective pulse oximeter sensor or the like. The force sensor 18 is a thin-film micro-force sensor with a diameter of 15 mm and a force range of 45N. The force sensor 18 also comprises associated read-out electronics.

The force sensor 18 is disposed on an upper portion of the optical sensor 20 and the optical sensor 20 is arranged such that it faces away from the force sensor 18 towards the arm 6.

The sensors 18, 20 are connected via respective electrical wires 10a, 10b, which comprise the lead 10, to an input of the monitoring device 8.

Figure 3:
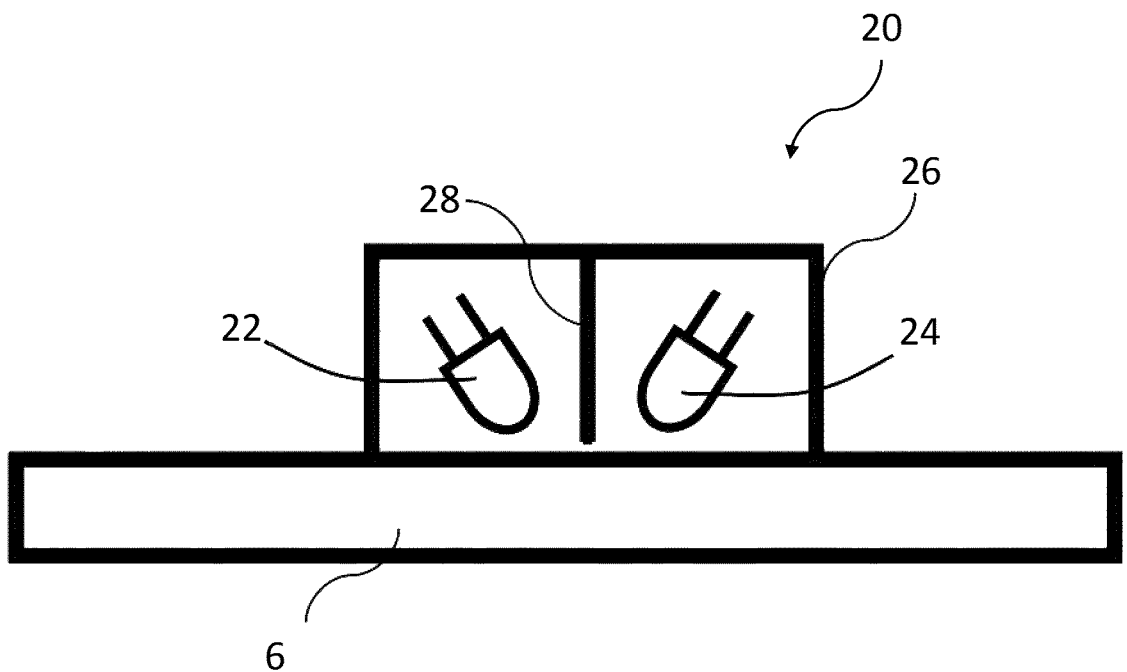
FIG. 3 is a schematic representation of a sensor for sensing a parameter associated with blood perfusion.

FIG. 3 is a schematic representation of the optical sensor 20 in isolation wherein the optical sensor 20 is located against the arm 6. The optical sensor 20 comprises a light emitter in the form of a light emitting diode (LED) 22 which emits light at a predetermined wavelength (or emits light across a predetermined range of wavelengths) and a light detector in the form of a photodiode 24 which is configured to detect light emitted by the LED 22.

The LED 22 and the photodiode 24 are disposed within a housing 26 and separated by a shield 28 which is opaque to the wavelength or range of wavelengths of light detectable by the photodiode 24. The shield 28 prevents emitted light from the LED being transmitted directly to the photodiode 24. The lower portion of the housing 26 is open or transparent so that light emitted by the LED 22 can pass through the lower portion to the skin tissue of the arm 6 and light reflected or scattered by the skin tissue of the arm 6 can pass back through the lower portion of the housing 26 to the photodiode 24. The shield 28 is spaced slightly from the skin tissue so that it does not contact the skin and so does not prevent light from passing underneath the shield 28. Light received by the photodiode 24 is therefore light which has been emitted by the LED 22 and either reflected, scattered or absorbed and reemitted by the skin tissue of the arm 6.

In the embodiment shown, the LED 22 emits light in the green band of the visible spectrum having a wavelength between 495 nm and 570 nm. Green light is known to be absorbed highly by hemoglobin within blood and so the amount of absorption of green light is correlated with the amount of blood in the skin tissue. Measuring the amount of absorption of green light emitted by the LED 22 can therefore be used to determine the amount of blood, and hence indicate the amount of blood perfusion, in a target area of tissue beneath the sensor module 14.

Referring again to FIG. 2, the monitoring device 8 comprises signal processing electronics 30 connected to the leads 10a, 10b and a processor 32 for processing signals received from the force sensor 18 and the optical sensor 20. The processor 32 is configured to display data representing the processed signals on the display 16. The signal processing electronics 30 are further configured to supply power to the sensor module 14. However, it will be appreciated that a separate power source may be provided, and that a power source may be integrated into the wound dressing. In other embodiments, the skin perfusion pressure determination device may comprise the processor and the processor may be configured to provide a digital output to the monitoring device.

A method of determining skin perfusion pressure using the apparatus 2 will now be described with reference to FIGS. 1 to 5.

The sensor module 14 is placed against the arm 6 of a patient so that the lower portion of the housing 26 of the sensor module 14, which is open or transparent, is adjacent the target area of skin tissue, as shown in FIG. 3. The lower portion of the housing 26 may be in contact with the target area. The skin perfusion pressure determination device 4 is then secured to a patient's arm 6 by wrapping the wound dressing 12 about the arm 6 and securing end portions of the wound dressing 12 together, as shown in FIG. 1. The sensor module 14 is connected to the monitoring device 8 by the lead 10 so that the sensor module 14 is in communication with the monitoring device 8.

Outputs from the force sensor 18 and the optical sensor 20 are then monitored and displayed on the display 16. Examples of outputs from the force sensor 18 and the optical sensor 20 are shown in the respective lower and upper traces of FIG. 5.

The upper trace is a photoplethysmogram (PPG) which provides an indication of the amount of light emitted by the LED 22 that is absorbed by the skin tissue at the target area (i.e. the trace is inversely proportional to the amount of light reflected by the skin tissue at the target area and received by the photodiode 24). Therefore, a relatively large amount of blood in the skin tissue, which absorbs a relatively large amount of light emitted by the LED 22, produces a relatively high output trace value, and vice versa. Of course, the trace could be inverted such that the amount of light reflected by the skin tissue is plotted in which case, a large amount of blood within the skin tissue would produce a relatively low output trace value.

The upper trace will typically have a pulsatile component and a non-pulsatile component. The pulsatile component represents light absorbed by pulsatile arterial blood whereas the non-pulsatile component represents light absorbed by non-pulsatile arterial blood, venous blood and skin tissue. The pulsatile component arises due to the change in blood volume caused by the pressure pulse of the cardiac cycle pushing blood through the blood vessels and capillaries and is therefore associated with blood flow. The pulsatile component can therefore be monitored to obtain an indication of the amount of blood perfusion in the underlying tissue.

Figure 5:
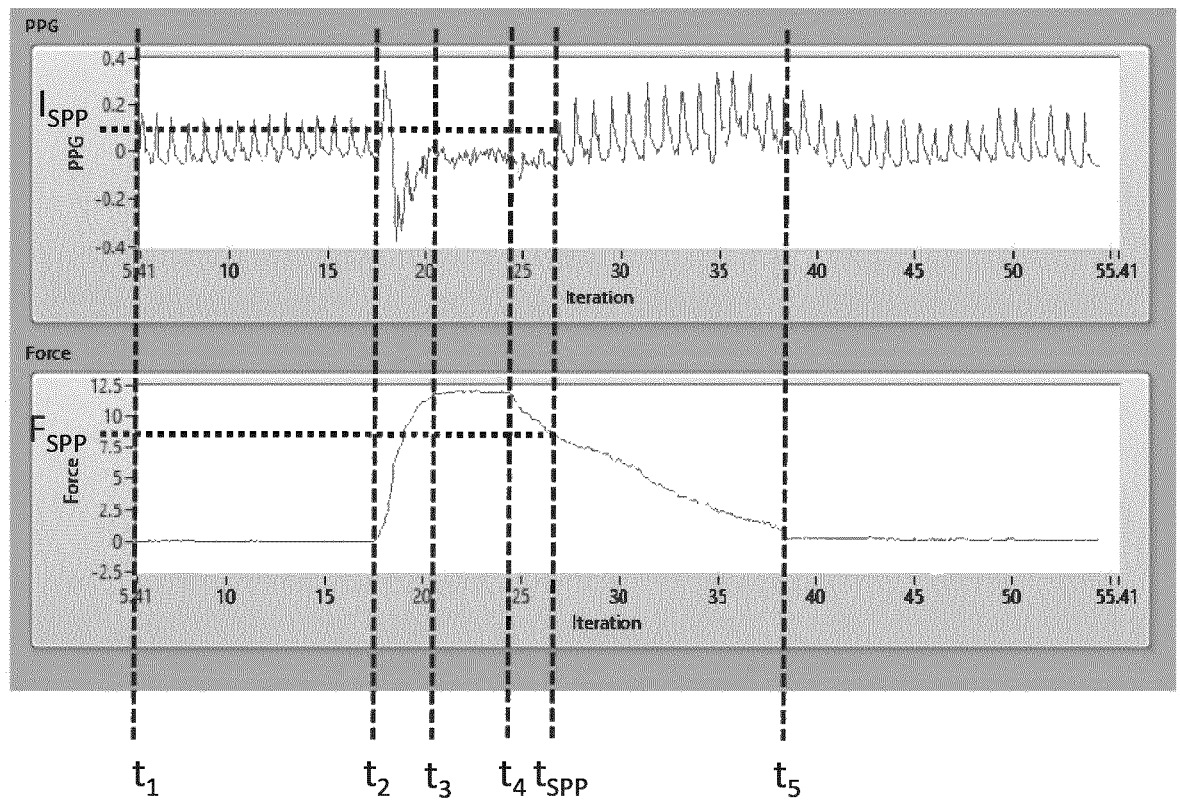
FIG. 5 is an example of a display derived from an output of the skin perfusion pressure determination device shown in FIG. 1.

The amount of light absorbed by the skin tissue initially once the skin perfusion pressure determination device 4 has been secured to the patient's arm 6 is shown between times $t_1$ and $t_2$ of the upper trace in FIG. 5. Each peak represents a pulse of arterial blood through the skin tissue at the target area.

Figure 4:
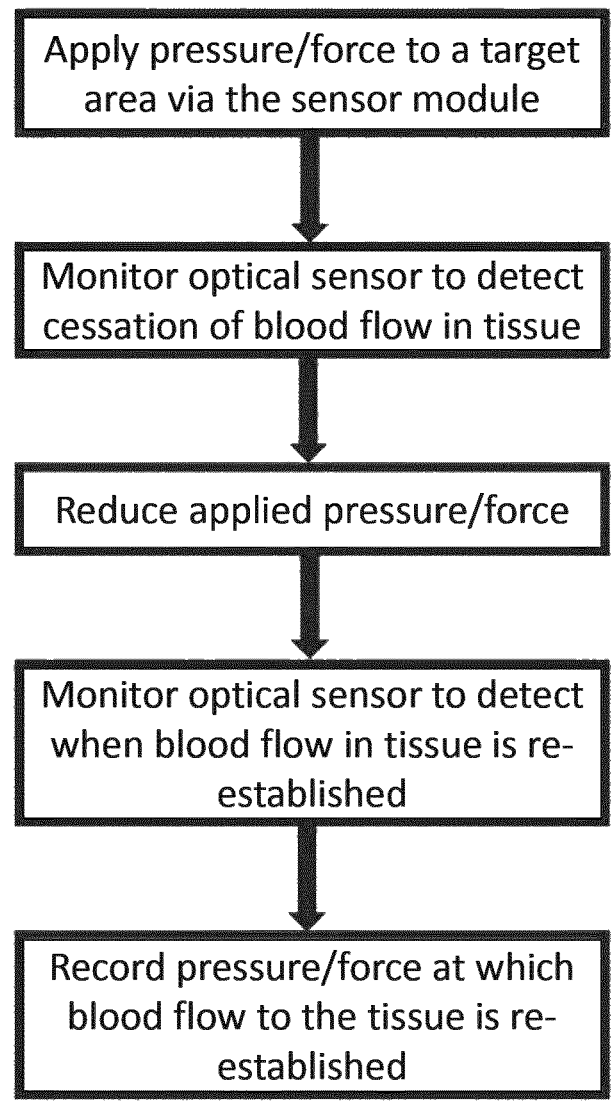
FIG. 4 is a flow chart depicting a method for determining skin perfusion pressure.

Time $t_2$ is the time at which a skin perfusion pressure measurement is commenced and corresponds to initiation of the first step of the method depicted by the flow diagram in FIG. 4.

In use, a clinician (or the patient themselves) presses the sensor module 14 against the arm 6 to occlude the blood vessels within the tissue below the target area. The amount of force is increased until the pulsatile component of the trace drops below a predetermined level or ceases to be evident, as shown at time $t_3$. Once the trace drops below the predetermined level, the clinician continues to hold the sensor module 14 against the arm 6 to ensure that the pulsatile arterial blood flow has ceased in the tissue at the target area, as shown between times $t_3$ and $t_4$. In the example shown, there remains a non-zero noise component of the trace which fluctuates at a level below the predetermined level. At time $t_4$, the clinician begins to reduce the force applied to the sensor module 14 slowly until time $t_5$ at which time the pressure module 14 has been released completely and pulsatile arterial blood flow in the tissue at the target area is completely restored.

The force exerted by the clinician on the tissue at the target area via the sensor module 14 is recorded by the lower trace. As can be seen from the lower trace, no force is recorded between times $t_1$ and $t_2$. The force increases relatively rapidly between times $t_2$ and $t_3$ as the clinician presses the sensor module 14 against the arm 6 of the patient and then plateaus while the clinician holds the sensor module 14 against the arm 6 between times $t_3$ and $t_4$. As the clinician begins to slowly release the sensor module 14 at time $t_4$, the applied force reduces steadily back to zero at time $t_5$ and pulsatile arterial blood flow returns to the skin tissue.

Pulsatile arterial blood flow returns when the blood pressure is sufficient to overcome the occlusion pressure on the blood vessels within the tissue which is applied by the clinician pressing on the sensor module 14. The return of blood flow is represented by a return of the pulsatile component in the upper trace, as shown at time $t_{SPP}$. Different criteria can be used to determine the return of pulsatile arterial blood flow. For example, return of blood flow could be determined by the return of the value of the upper trace to a predetermined threshold $I_{SPP}$ value such as a value greater than a maximum expected noise value. Alternatively, the threshold value $I_{SPP}$ may be a value that is determined based on the pulse amplitude observed before a force is applied to occlude the blood vessels (i.e. the pulse amplitude between times $t_1$ and $t_2$). In one example, a threshold value $I_{SPP}$ may be used which is a predetermined percentage of the pulse amplitude observed before a force is applied to occlude the blood vessels. Other algorithms may be used to determine return of the pulsatile component of the trace.

The magnitude of the force $F_{SPP}$ of the lower trace at time $t_{SPP}$ is then recorded. The recorded force $F_{SPP}$ can subsequently be used to determine a skin perfusion pressure. This may be done by calculation, look-up tables or based on a pre-calibration of the force sensor 18. For example, if the contact area of the portion of the sensor module 14 pressed against the skin tissue is known, the pressure applied to the skin tissue can be calculated. In this instance, the target area corresponds to the contact area of the sensor module 14. In the described embodiment, the contact area of the sensor module 14 is circular and has a diameter of 10 mm and therefore a surface area of approximately 80 mm². The larger the contact area, the greater the force required to stop blood flow. The smaller the contact area, the greater the fluctuations in pressure caused by fluctuations in the force applied so that, for very small contact areas it becomes difficult for a clinician to release the applied force in a controlled manner in order to determine the force at which blood flow returns. A very small contact area can also make it difficult for an accurate reading to be taken by the blood perfusion sensor. The contact area of the sensor module 14 may therefore be between 1 mm² and 1000 mm², for example between 10 mm² and 400 mm².

A benefit of the arrangement is that contemporaneous measurements of the pressure exerted by the sensor module 14 on the target area and the amount of blood perfusion are made at the target area. The measurements can be taken and recorded simultaneously to produce an accurate and reliable measurement of blood perfusion pressure at a desired location on a patient's body.

Measurement of skin perfusion pressure may be performed as a single measurement or determined from trends evident from repeated measurements over time. Such measurements may be used to aid the prediction of wound healing.

Use of an LED light source, in particular a surface-mount LED, provides a compact, widely available, inexpensive, very reliable and a low power consumption light source. In the embodiment described above an LED which emits light in the green band of the visible spectrum is used. However, other suitable light sources could be used which emit light having a wavelength that is absorbed or reflected by blood. Light sources which emit light having a wavelength (or range of wavelengths) between 600 nm and 1350 nm may be used. In particular, light sources which emit light in the red band of the visible spectrum having a wavelength of between 600 nm and 750 nm or which emit light in the near-infrared band of the visible spectrum having a wavelength of between 850 nm and 1000 nm may be used. Light sources which emit light in the near-infrared window of biological tissue having a wavelength of between 650 nm and 1350 nm are beneficial because light has its maximum depth of penetration in tissue at these wavelengths and so a greater proportion of the emitted light will reach the blood vessels within the tissue.

Alternative light detectors may be used. For example, phototransistors or complementary metal-oxide semiconductor (CMOS) based sensors may be used. These sensors, and the photodiodes of the described embodiment, are preferred because they are inexpensive, compact and widely available.

Alternative sensors for determining a parameter associated with a pressure exerted on the target area may be used. In particular, sensors which have a thickness which corresponds to, or is less than, the thickness of a typical wound dressing may be used. Suitable capacitive, resistive thin-film or micromachined sensors or strain gauges or the like may be used. Such sensors are suitable for incorporation onto wound dressings, as described below. It will be appreciated that although the embodiment described above comprises a force sensor, alternative types of sensor which produce an output which can be used to determine a parameter associated with the pressure exerted on or stress created at the target area by a sensor module may be used. Such sensors may include sensors configured to output a pressure applied by the sensor or the sensor module to the target area.

In the embodiment described above, a simple trace showing the outputs from the sensor module 14 is provided to aid the clinician or patient. The processor may, however, be configured to display instructions to a patient/clinician on the display 16 such as instructions to increase the applied force or to reduce the applied force at each stage of the measurement process. An audible signal may be generated to inform a clinician/patient of the pulse strength. The audible signal may be continuous or a series of beeps that vary in frequency or volume depending on the magnitude of the pulsatile component of the trace. For example, an audible beep pattern may become silent when the pulsatile component drops below a threshold value and re-emerges when the pulsatile component returns indicating the return of blood flow in the tissue at the target area. In addition to written instructions, a light or a symbol or a color signal or an audible signal could be used to instruct a user to increase or decrease a force applied.

Figure 6:
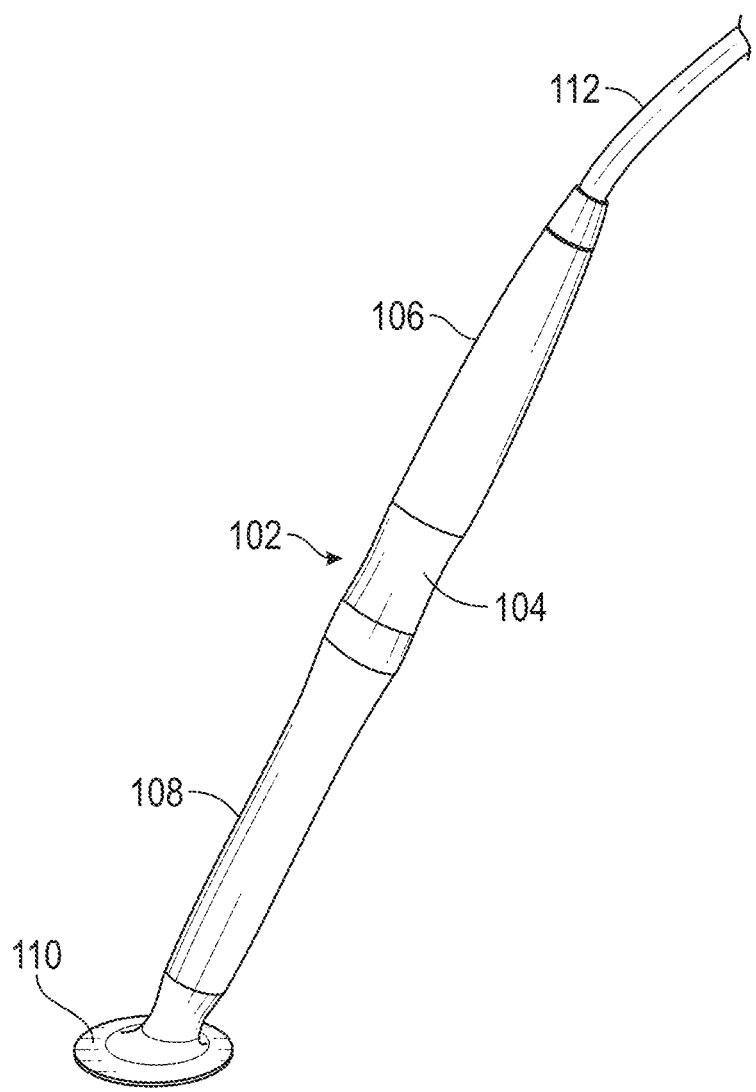
FIG. 6 shows an alternative embodiment of a skin perfusion pressure determination device comprising a probe portion.

FIG. 6 shows an example of an alternative embodiment of part of an apparatus 102 comprising a hand-held skin perfusion pressure determination device 104 comprising a grip portion 106 and a probe portion 108. The probe portion 108 has a pad portion 110 in which a sensor module (not shown) is housed. The sensor module is in accordance with the sensor module 14 shown in FIG. 2. The hand-held device 104 is connected to a monitoring device similar to that shown in FIG. 1 by a lead 112.

In use, the grip portion 106 is held by a clinician and used to press the pad portion 110 against a target area of a patient's skin. The method shown in FIG. 4 and described above is then followed to determine the skin perfusion pressure at the target area.

Figure 7A:
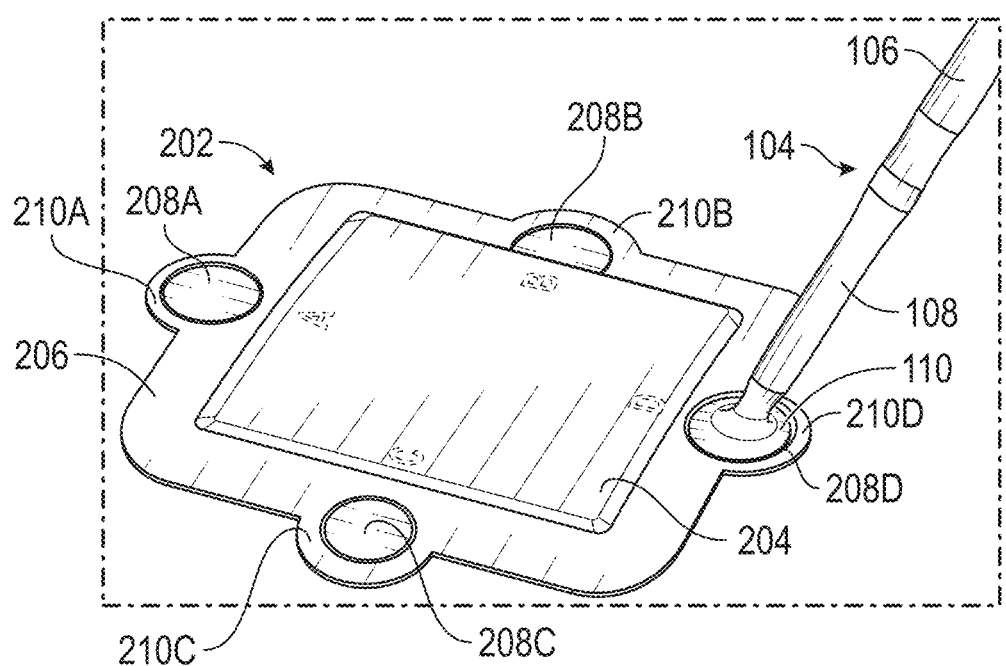
FIG. 7A shows the skin perfusion pressure determination device shown in FIG. 6 in use with a wound dressing.

FIG. 7A shows the hand-held device 104 in use with a wound dressing 202. The wound dressing 202 comprises a central wound protecting portion 204 and a peripheral securing portion 206. As illustrated in FIG. 7A, the peripheral securing portion 206 extends around the perimeter of the central wound protecting portion 204 and forms the perimeter of the wound dressing 202. The securing portion 206 has an adhesive, such as an acrylic adhesive or silicone adhesive or the like, on its lower surface for securing the wound dressing 202 to a patient's skin.

Four circular windows 208A, 208B, 208C, 208D are provided in respective lobes 210A, 210B, 210C, 210D of the securing portion 206. The lobes 210A, 210B, 210C, 210D are spaced apart about the wound protecting portion 204 so that each lobe 210A, 210B, 210C, 210D is positioned opposite one of the other lobes 210A, 210B, 210C, 210D. Each window 208A, 208B, 208C, 208D is defined by an opening through which the pad portion 110 can be pressed directly against a patient's skin. Each window 208A, 208B, 208C, 208D has a size and shape which corresponds to the size and shape of the pad portion 110 in order to help locate the pad portion 110 as it is pressed against a patient's skin. The windows 208A, 208B, 208C, 208D provide a convenient way in which blood perfusion pressure can be measured at a target area close to the location of a wound without having to remove a wound dressing. The fixed location of the windows 208A, 208B, 208C, 208D also ensures that measurements of skin perfusion pressure can be repeatedly and reliably made at the same location or locations to assess wound healing. This facilitates consistent and robust tracking of wound healing. Other shapes of windows that help locate a suitably shaped pad portion of a hand-held device could of course be utilized. At least some of the lobes 210A, 210B, 210C, 210D may be detachable, for example, by being connected to the remainder of the wound dressing 202 via one or more perforated sections. Furthermore, the windows 208A, 208B, 208C, 208D could be revealed and/or created at the time of use by removing detachable portions of the wound dressing 202 immediately before application of the wound dressing 202. The detachable portions may be connected to the remainder of the wound dressing 202 via one or more perforated sections. The quantity, location and size of the lobes may be tailored in accordance with requirements such as body location for the wound dressing or wound size or wound type.

The wound dressing 202 has an upper surface on which indicia are provided in order to determine the orientation of the wound dressing 202. In some embodiments, the indicia can be used to determine orientation, detect the target area or location of measurement, and/or identify the wound dressing. Since the time between measurements can be between about one day to about seven days, the indicia can assist the user in assuring accurate and repeated measurements can be taken form the same location and/or dressing.

In some embodiments, the indicia can comprise alphanumeric characters A, B, C and D, as shown in FIG. 7A, but may comprise directional markers or the like for determining the orientation of the wound dressing and for uniquely identifying each of the windows 208A, 208B, 208C, 208D of the wound dressing 202. Each indicium may comprise a symbol or one of more color patches or folds in the dressing material or dimples or indentations or holes or metal elements or magnetic elements or resonant tags. As used herein, the upper surface of the wound dressing refers to the surface of the wound dressing that is furthest from or distal to the wound bed.

Figure 7B:
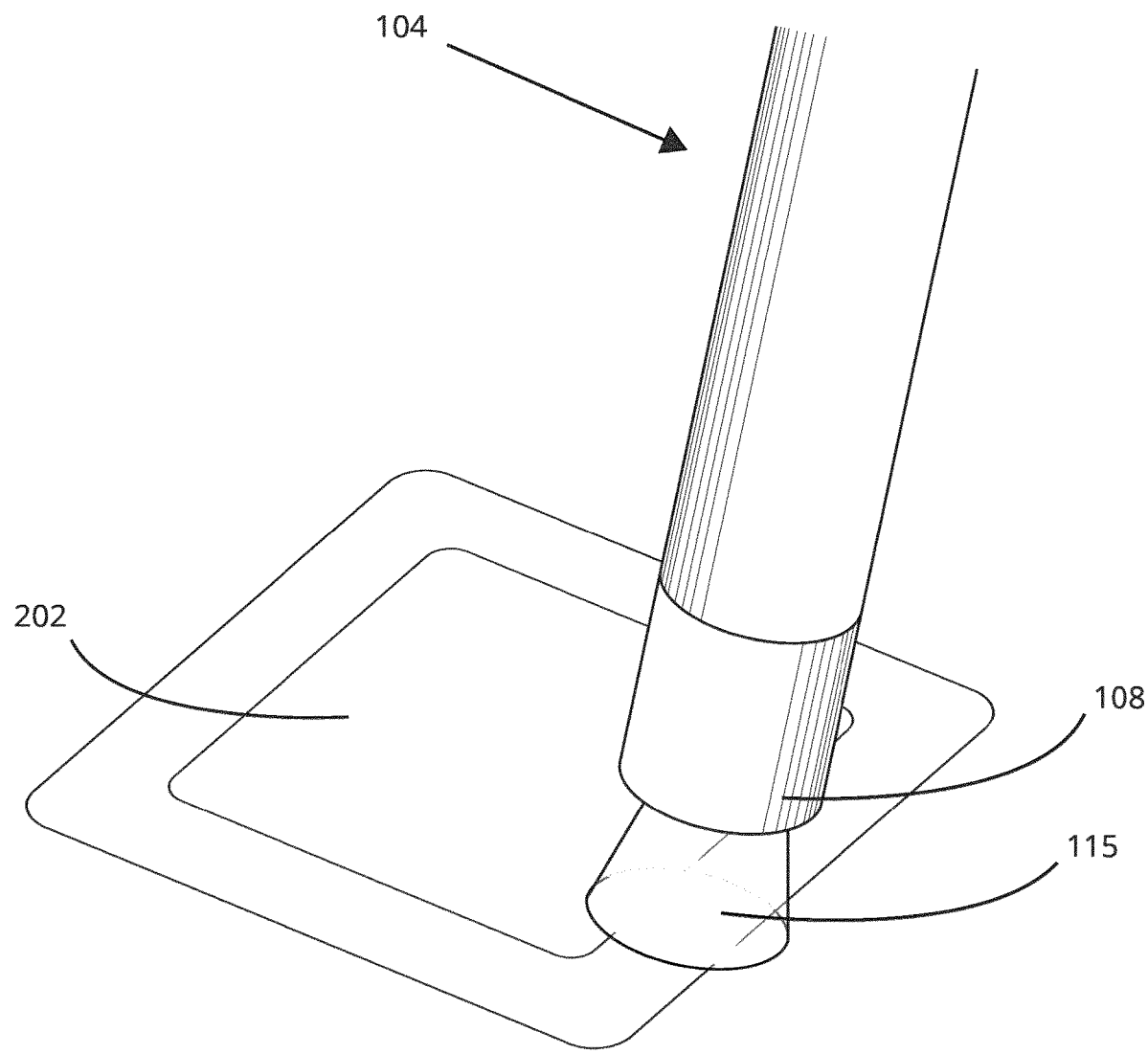
FIG. 7B illustrates an embodiment of a hand-held skin perfusion pressure determination device.
Figure 7C:
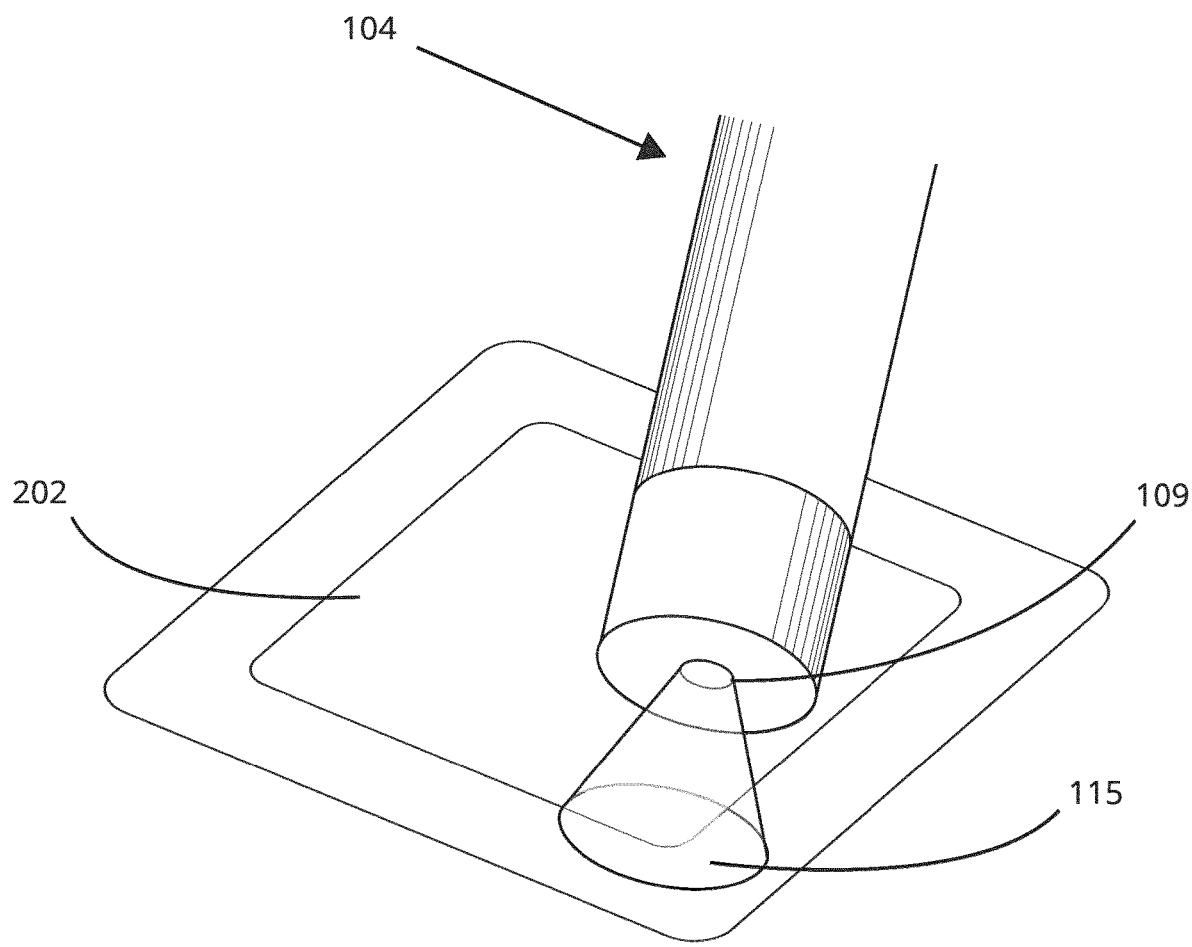
FIG. 7C-7D illustrates an embodiment of a hand-held skin perfusion pressure determination device with an illumination source.
Figure 7D:
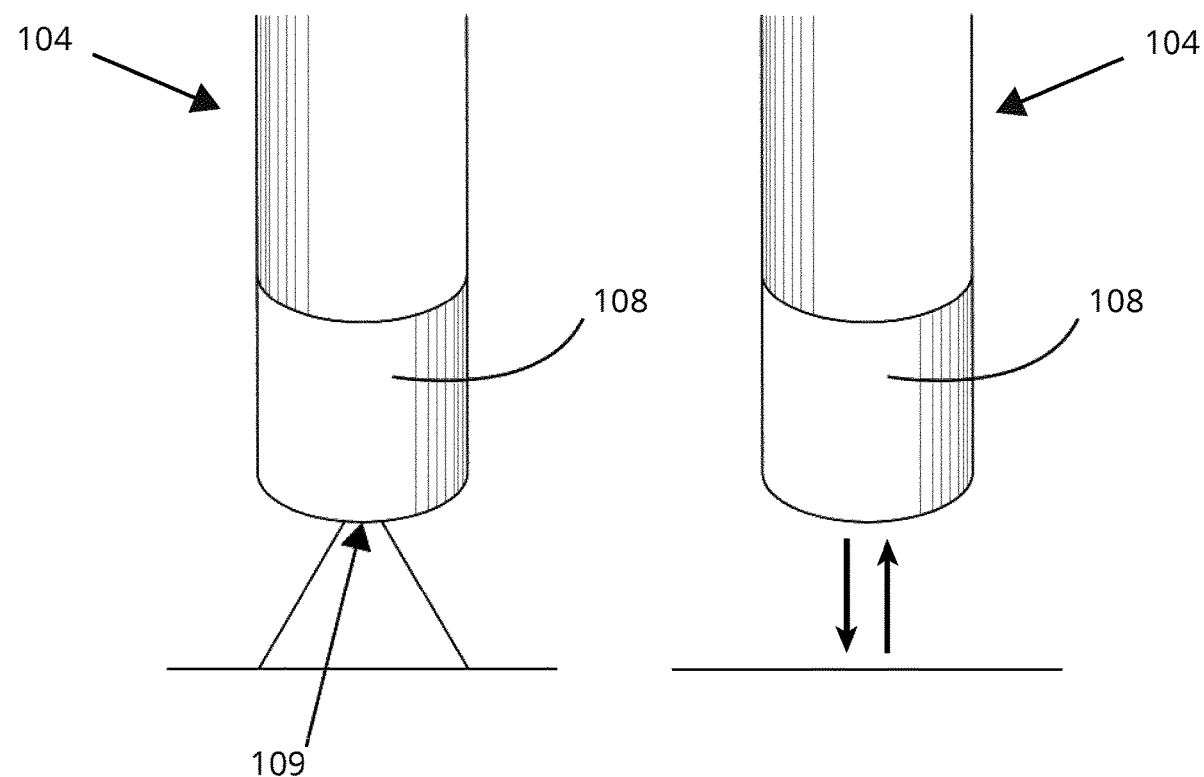

Other indicia and patterns can be used to determine orientation, detect the target area or location of measurement, and/or identify the wound dressing. In some embodiments, locations on the wound dressing can be color-coded. In some embodiments, the wound dressing can have color patches or be color-coded to identify the orientation, location, and/or identify the wound dressing. The coloring can be used to identify the target area for taking a skin perfusion pressure measurement. Color patches can be used next to or on the intended measurement location. In some embodiments, the color can be detected using a color sensor on or in the measurement device. The probe portion 108 of the hand-held skin perfusion pressure determination device or other device with a sensor module can include a color sensor which can be used to detect a color patch on or near the wound dressing 202. In some embodiments, the hand-held skin perfusion pressure determination device 104 can include an illumination source. As shown in FIGS. 7B and 7C, the illumination source 109 of the hand-held skin perfusion pressure determination device 104 can illuminate an area 115 on the upper surface of the wound dressing. In some embodiments, the wound dressing can be marked with a color patch that is visible when illuminated by the illumination source. For example, the color patch could be a color that is visible on an ultraviolet spectrum and can be visible when illuminated by an ultraviolet light from the illumination source 109. In some embodiments, the illumination source can illuminate the upper surface of the wound dressing and the reflected light can be detected by the color sensor or other sensor as illustrated in FIG. 7D. In some embodiments, such imaging or illumination can be used to detect bacteria in wounds (for example systems such as MolecuLight).

Figure 7E:
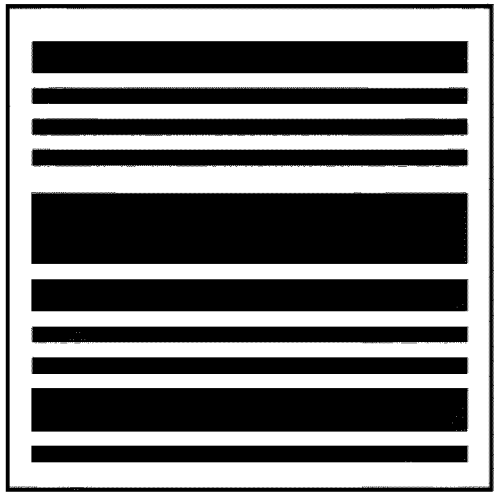
FIGS. 7E-7K illustrate embodiments of optical pattern indicia.
Figure 7F:
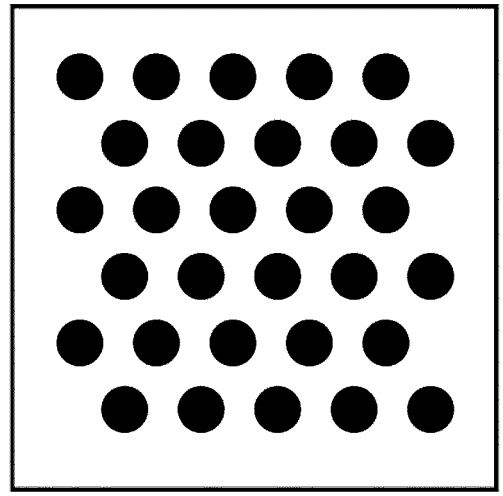
Figure 7G:
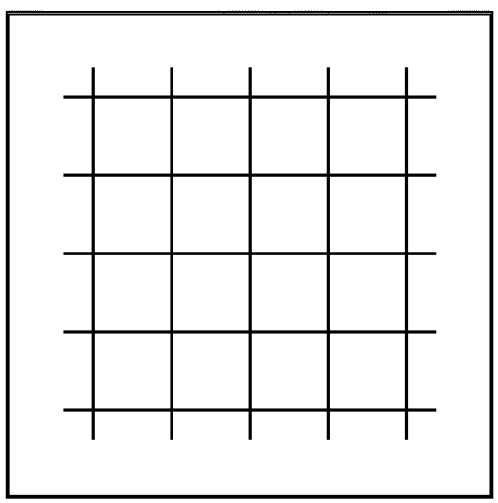
Figure 7H:
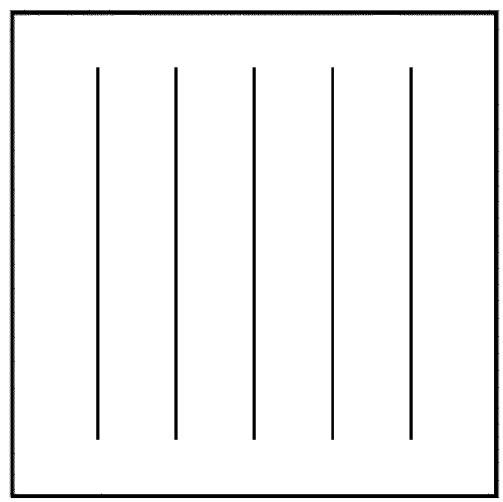
Figure 7I:
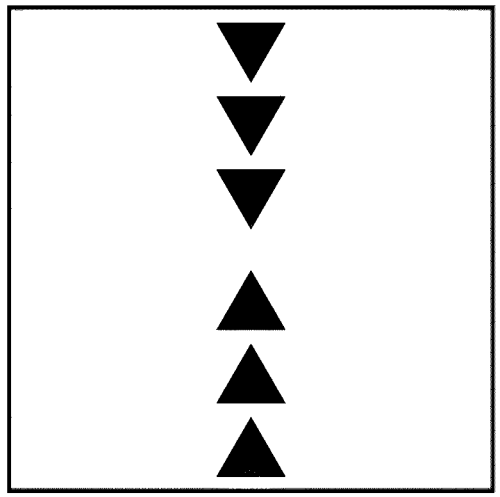
Figure 7J:
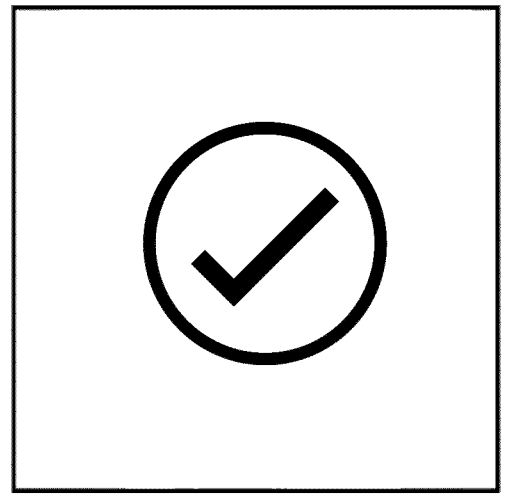
Figure 7K:
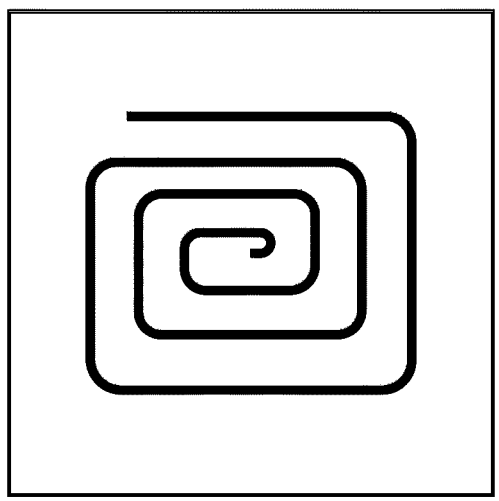

In some embodiments, the wound dressing can include an optical pattern to identify the target area on the wound dressing. FIGS. 7E-7K illustrate various optical patterns that can be used. FIG. 7E illustrates an embodiment of a bar code. FIG. 7F illustrates an embodiment of a dot pattern. FIGS. 7G and 7H illustrate embodiments of line patterns that can be used including grid pattern (shown in FIG. 7G) or parallel lines (shown in FIG. 7H). In some embodiments, directional indicators similar to those shown in FIG. 7I can be used on the wound dressing. In some embodiments, symbols or drawings similar to those shown in FIGS. 7J and 7K can be used.

Figure 7L:
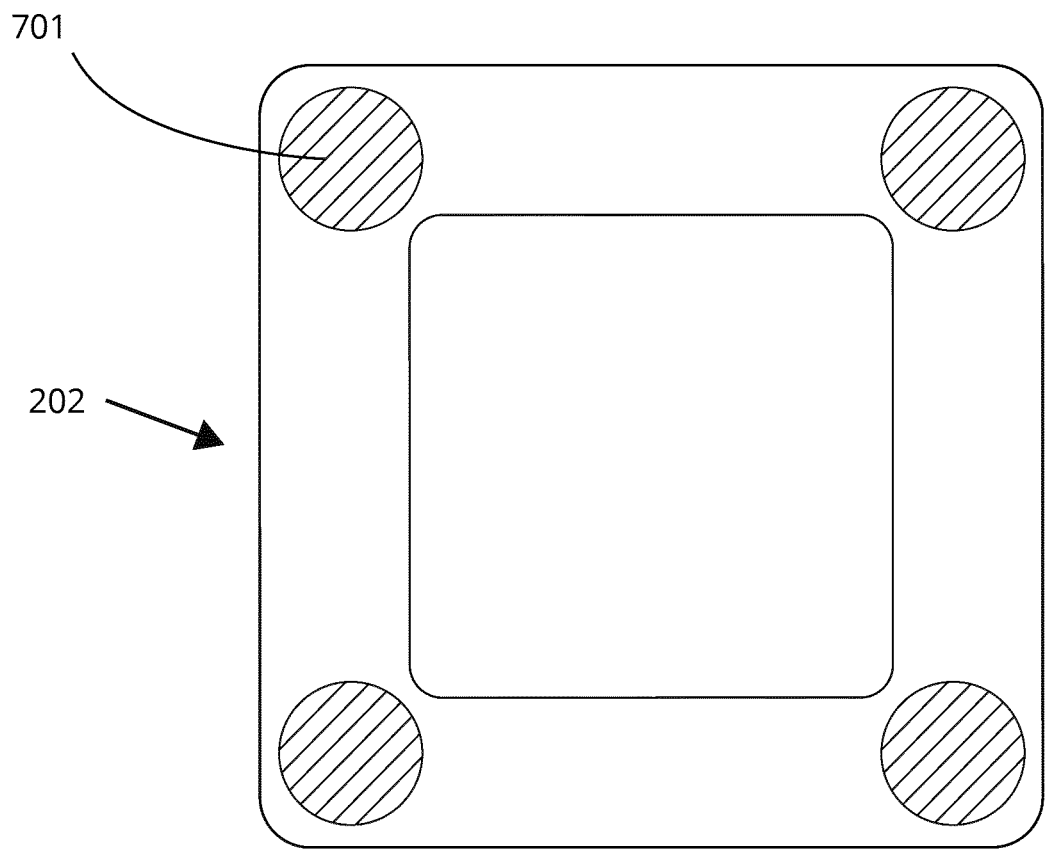
FIGS. 7L-7O illustrate embodiments of a wound dressing with indicia.
Figure 7M:
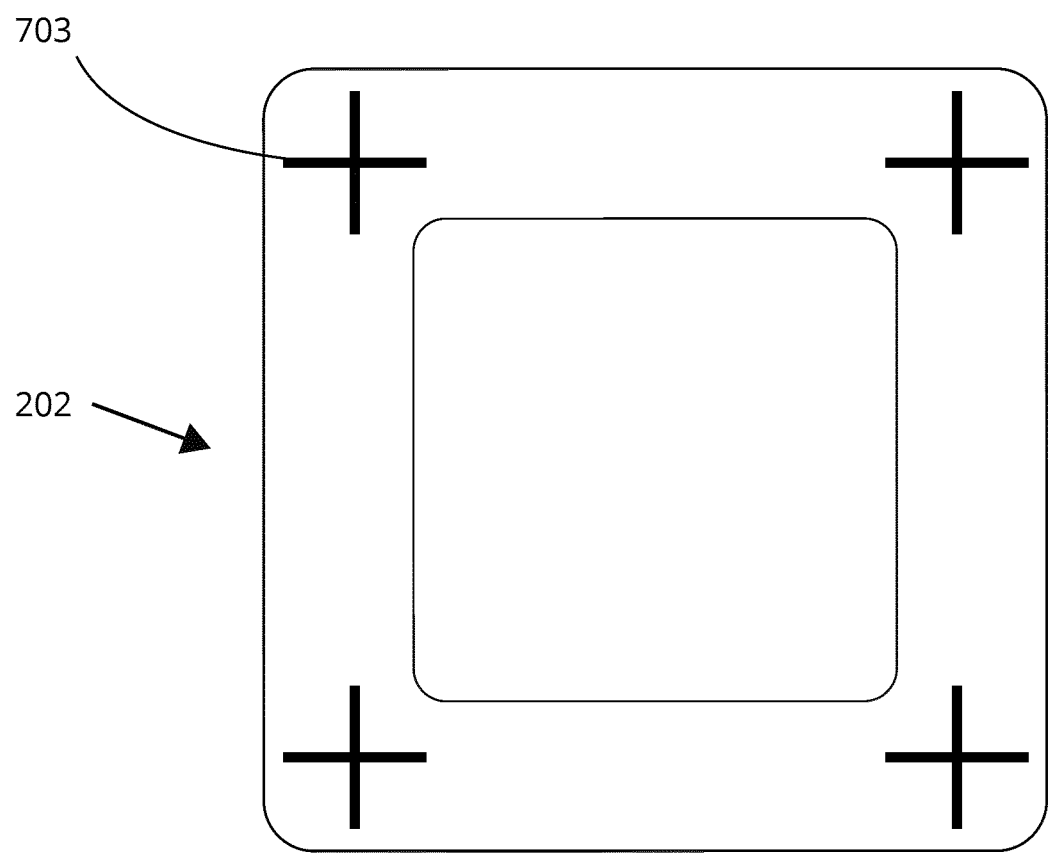

As shown in FIGS. 7L and 7M the wound dressing 202 can have one or more of a color 701 (shown in FIG. 7L) or a pattern 703 (shown in FIG. 7M) similar to those described herein positioned on a location of the wound dressing to determine orientation, detect location of measurement, and/or identify the wound dressing. The hand-held skin perfusion pressure determination device can be positioned over the wound dressing and can utilize a camera to detect the color, pattern, or other indicia on the wound dressing. The hand-held skin perfusion pressure determination device 104 can include a camera to detect the pattern and to identify the measurement location. In some embodiments, the hand-held skin perfusion pressure determination device can include an illumination source to assist in capturing the color, pattern, or other indicia on the surface of the wound dressing.

Figure 7N:
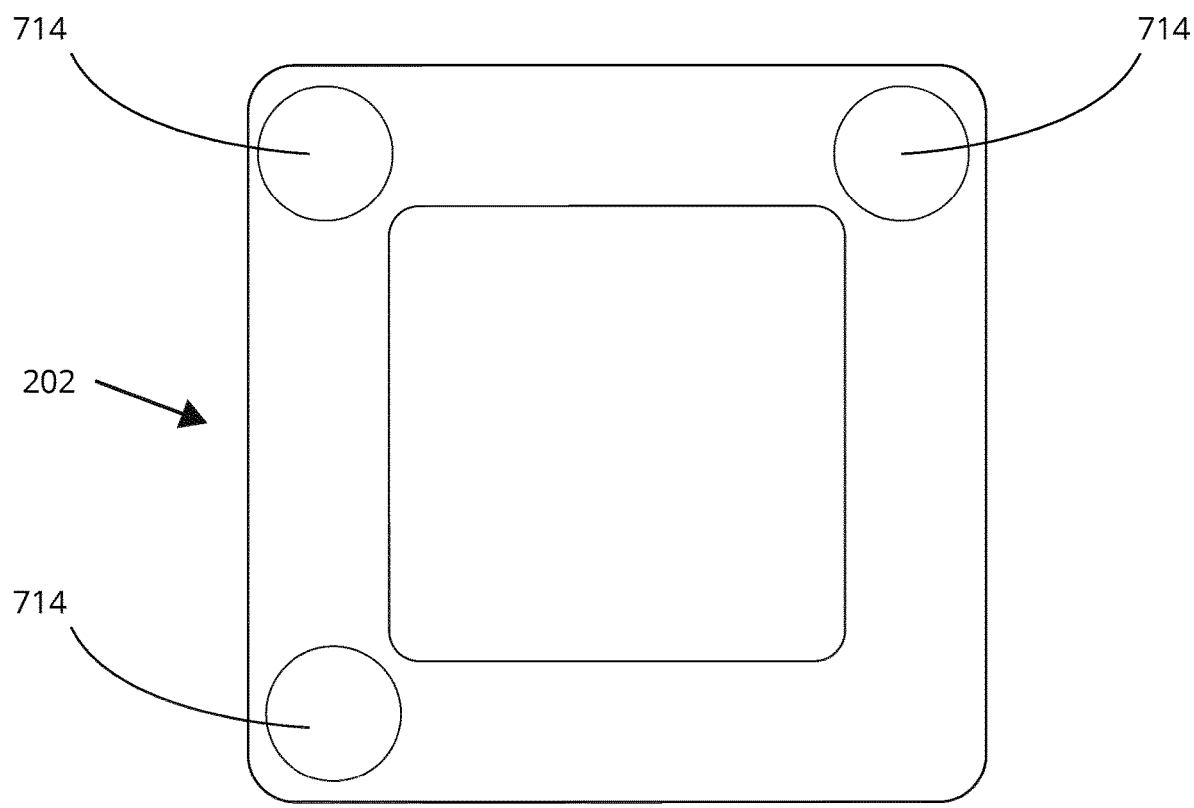

The orientation of the wound dressing, the location of measurement, and/or the identity of the wound dressing can be determined by observing the indicia on the upper surface of a wound dressing. In some embodiments, the indicia can be positioned on the dressing in an asymmetrical way. For example, the indicia 714 can be positioned in three of the four corners of a square dressing 202 as illustrated in FIG. 7N. Since the wound dressing can be sided (including a top backing layer and a wound contact layer) the orientation can be determined by simply using the indicia in three of the corners.

Figure 7O:
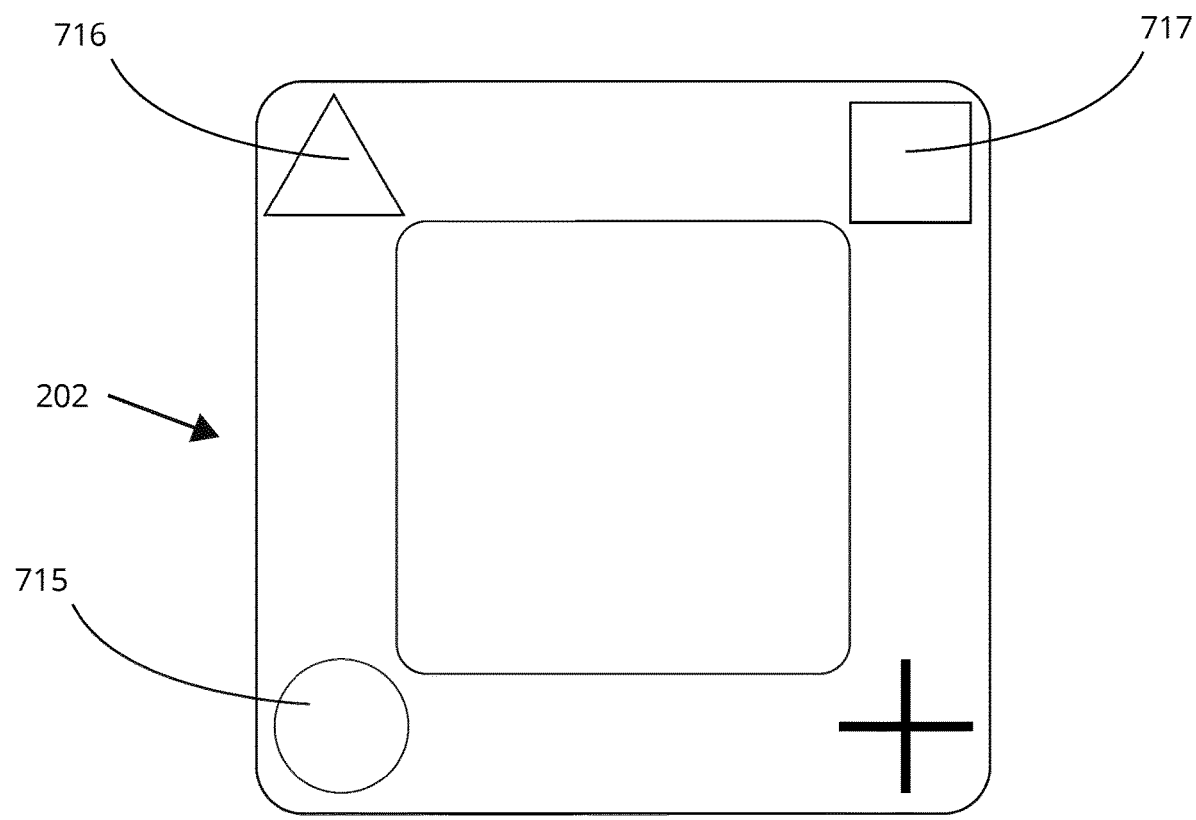

In some embodiments, as illustrated in FIG. 7O, the wound dressing 202 can have indicia of different shapes, styles, and/or sizes positioned at different locations of the wound dressing to determine orientation, detect location of measurement, and/or identify the wound dressing. The wound dressing 202 can have unique indicium at each location. For example, the wound dressing 202 can have a circle indicium 715, a triangle indicium 716, and a square indicium 717. In some embodiments, the unique indicium at each location can assist the user to confirm that readings and/or measurements have been consistently taken from the same location for each measurement time.

While FIGS. 7L-7O illustrate the use of a pattern or a color indicium, any colors, pattern, code, and/or notch in the sides of the dressings can be used instead or in addition to the patterns or colors to identify a location or to identify the dressing.

In some embodiments, magnetic encoding can be utilized to assist the user to identify the location for measurement on the wound dressing. A magnetic material or pattern in the wound dressing can be used next to or on the intended measurement location, a location used to determine orientation, and/or a location used to identify the wound dressing. The hand-held device can include a magnetic sensor (for example, a magnetometer) to detect the magnetic material or pattern in the wound dressing. In some embodiments, the magnetic material can utilize different amounts of magnetic material in different locations to generate a different size of signal detected by the detection device or hand-held device. In some embodiments, the different size of signal detected can be subject to the sensitivity of the magnetometer or magnetic sensor. In some embodiments, various patterns of magnetic material can be used to identify locations on the wound dressing.

Each indicium may comprise an RFID identification tag that is configured to communicate information, such as the location of the RFID tag and/or a window associated with the RFID tag to the hand-held device 104 when the pad portion 110 is located at the respective window. In other embodiments, a combination of an RFID tag and a visible marker could be used in which the visible marker and the RFID tag store information that, when combined, can be used to identify a wound dressing and/or a patient to which a wound dressing is applied. For example, a dressing may have an identifier in the form of a serial number. At least a portion of the serial number may be obtainable from the RFID tag and a different portion of the serial number may be obtainable from the visual marker. The two portions can be combined to enable anonymous identification of a wound dressing, and hence a patient to which the wound dressing has been applied.

The hand-held device may comprise a suitable RFID reader or camera module for acquiring information about the indicia of the wound dressing. The apparatus may be configured to associate a measurement with a wound dressing or a certain window/lobe of the wound dressing.

It will be appreciated that the windows 208A, 208B, 208C, 208D could be formed of a material that is transparent to a wavelength of the light used by the optical sensor of the sensor module. For example, each window 208A, 208B, 208C, 208D may be made of a material that is transparent, or substantially transparent, to green light having a wavelength of between 495 nm and 570 nm. The windows may comprise, for example, at least one of polyvinyl chloride (PVC), cellulose acetate or acrylic or silicone or polyurethane or acylate or other suitable material.

Figure 7P:
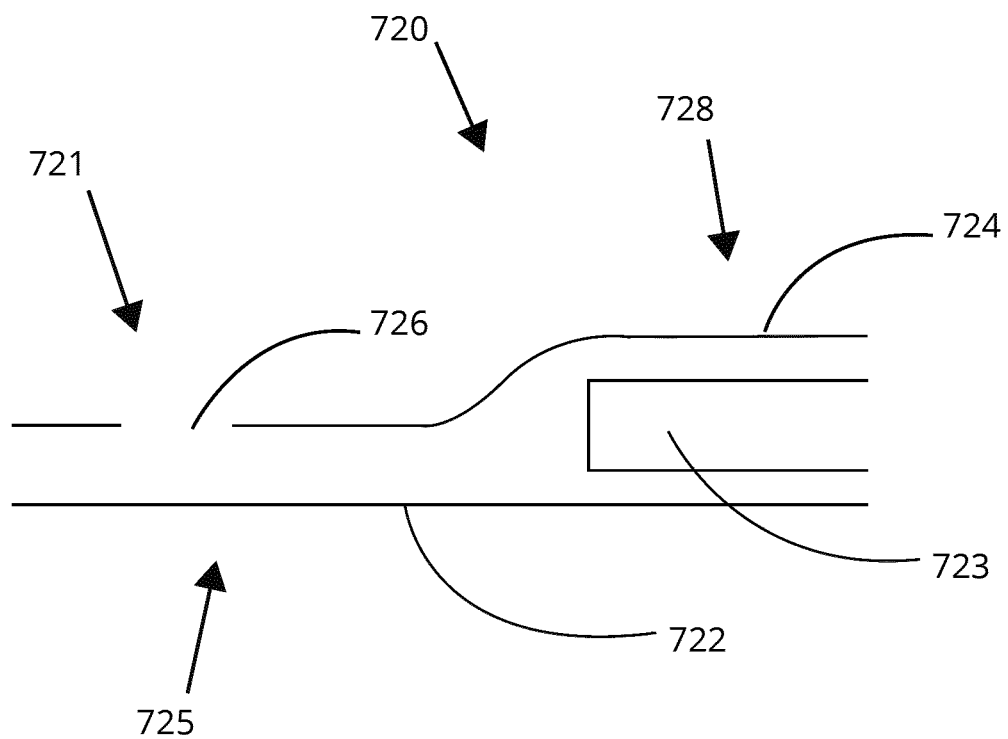
FIGS. 7P-7Q illustrate embodiments of a cross section of a wound dressing.
Figure 7Q:
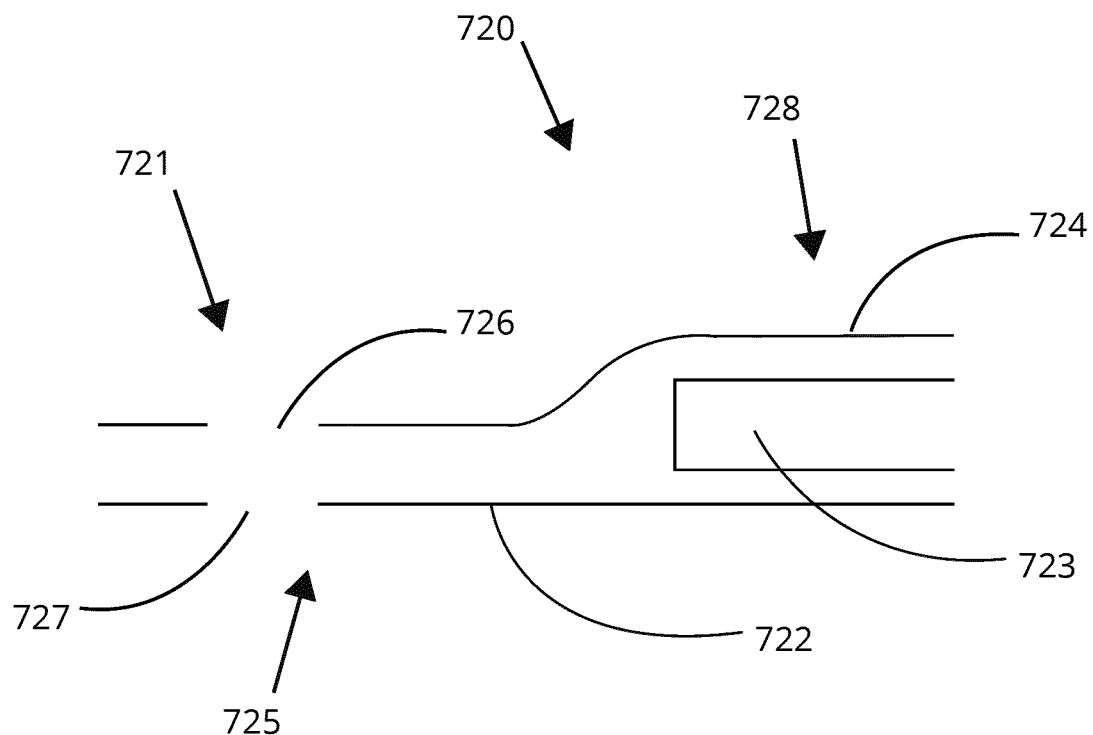

FIGS. 7P-7Q illustrates a cross-sectional view of the wound dressing 720 with a window 721. The wound dressing 720 of FIGS. 7P and 7Q illustrates a cross section of an embodiment of the wound dressing described herein with reference to FIG. 7A. As described previously, the wound dressing 720 can include a peripheral securing portion 725 and a central wound protecting portion 728. As illustrated in FIGS. 7P and 7Q, the wound dressing 720 can include a wound contact layer 722, an absorbent or foam layer 723, and a top film or backing layer 724.

In some embodiments, the windows 208A, 208B, 208C, 208D shown in FIG. 7A could be formed of the material of a wound contact layer from the wound dressing that extends under the window portion of the dressing. As illustrated in FIG. 7P, the wound contact layer 722 can extend across the peripheral securing portion 725 of the dressing 720 and across the window 721. The backing layer 724 can include an opening 726 in the window portion 721 of the wound dressing. In such embodiments, the hand-held skin perfusion pressure determination device can be positioned over the wound contact layer 722 in the window 721.

FIG. 7Q illustrates an embodiment of the wound dressing 720 with an opening 727 in the wound contact layer 722 and an opening 726 in the backing layer 724 in the window portion 721 of the wound dressing. In the embodiment of FIG. 7Q, the hand-held skin perfusion pressure determination device would be positioned in the window 721 and no material would be present in the window portion of the wound dressing between the hand-held skin perfusion pressure determination device and the skin of the patient. In such embodiments, the hand-held skin perfusion pressure determination device can make direct contact with the skin in the window. In some embodiments, the wound contact layer and absorbent or foam layer is optional.

In some embodiments, the backing layer 724 can be formed from a thermoplastic polyurethane. The wound contact layer 722 can be a perforated layer and can optionally include an adhesive. In some embodiments, the absorbent or foam layer 723 can be any dressing construction material, for example, a spacer layers, super absorbers, non-wovens, foams, masking layers, and/or any combination thereof.

In some embodiments, a separate dressing layer can be used to form the material of the window. For example, a wound contact layer can be used under the absorbent and/or foam layer or the central wound protecting portion 728. A separate non-perforated and/or non-adhesive film can be used around the peripheral securing portion 725 of the dressing and/or within the windows. In some embodiments, the material used within the window can be selected for pressure and/or optical transmission.

Figure 7R:
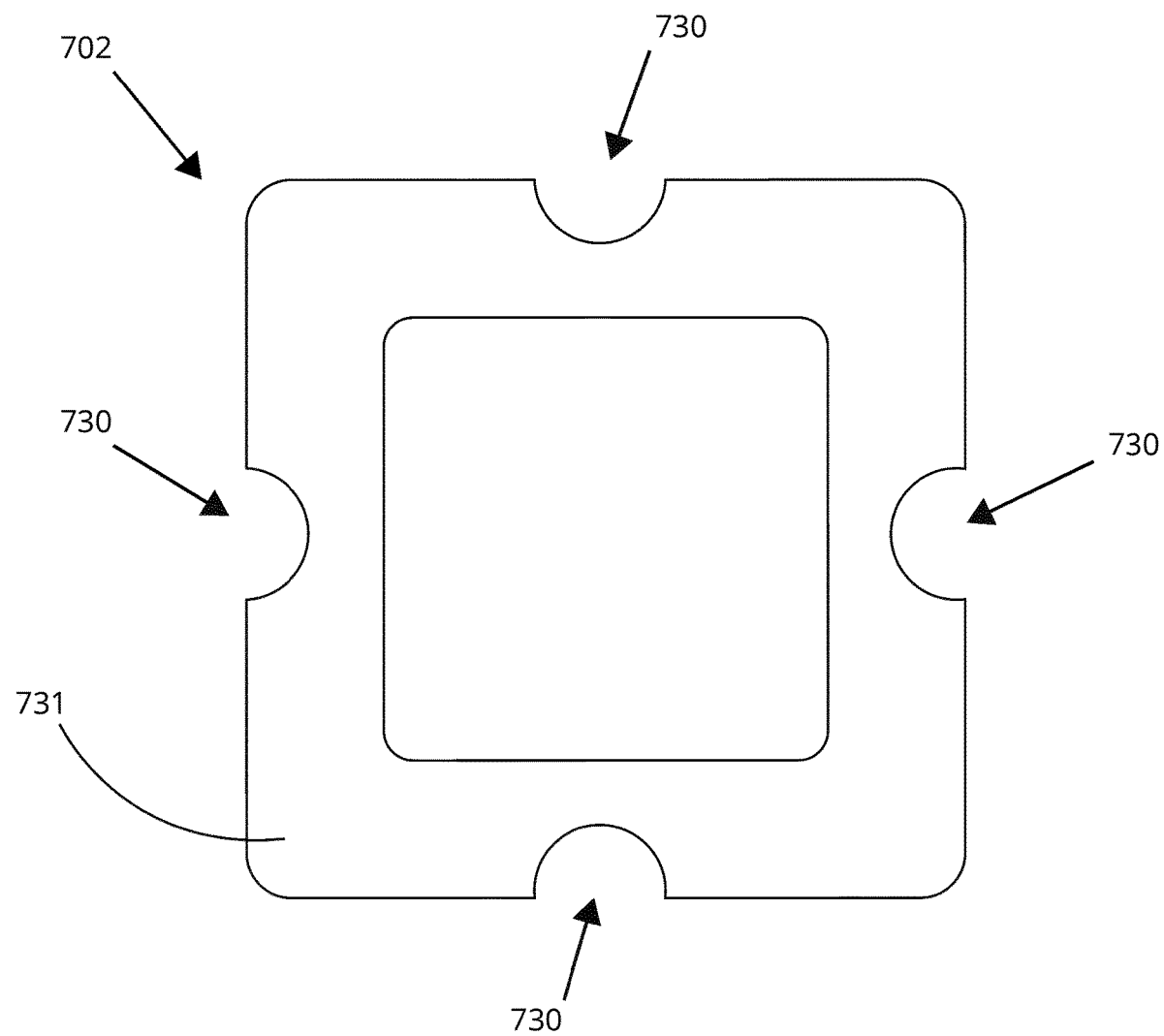
FIG. 7R illustrates an embodiment of a wound dressing with notches.

FIG. 7R illustrates a wound dressing 702 with notches 730 along the peripheral securing portion 731 of the dressing. The notches 730 can indicate the measurement locations for measurements by the hand-held skin perfusion pressure determination device. For example, instead of detaching lobes 210A, 210B, 210C, 210D from the dressing as described with reference to FIG. 7A, the dressing could be designed with the notches illustrated in FIG. 7R.

Figure 8:
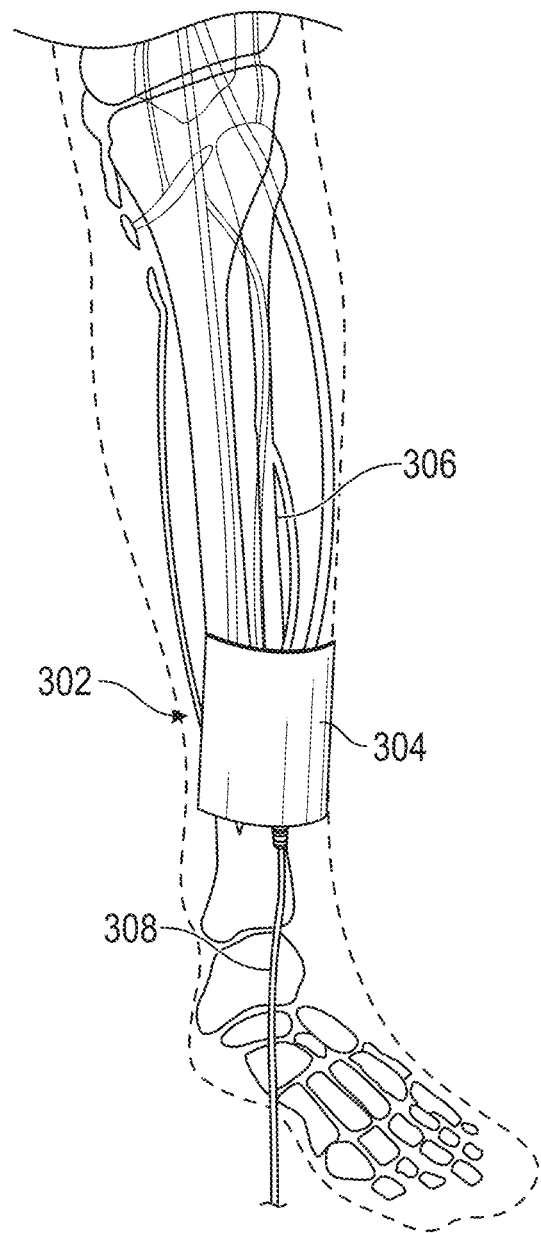
FIG. 8 shows a further embodiment of a skin perfusion pressure determination device comprising a wound dressing.

FIG. 8 shows a skin perfusion pressure determination device 302 comprising a wound dressing 304 having an integrated sensor module that is in accordance with the sensor module 14 shown in FIG. 2. The wound dressing 304 is shown attached to the leg 306 of a patient. A lead 308 connects the sensor module to a monitoring device (not shown) such as that shown in FIG. 1.

Figure 9A:
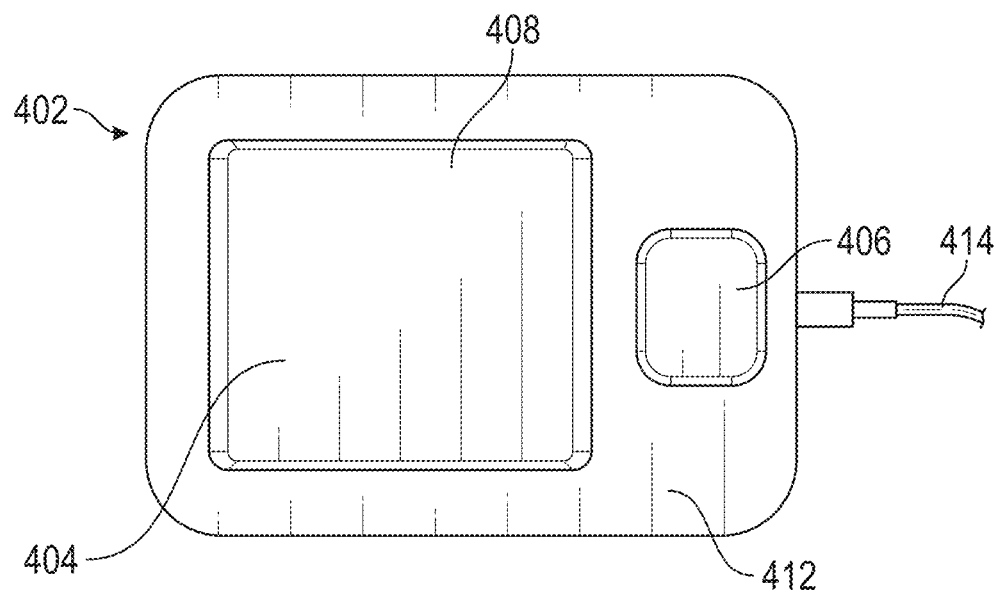
FIG. 9A shows an example of a skin perfusion pressure determination device comprising a wound dressing.

FIG. 9A shows an embodiment a skin perfusion pressure determination device 402 comprising a wound dressing 404 having an integrated sensor module 406 that is in accordance with the sensor module 14 shown in FIG. 2. The wound dressing 404 comprises a central wound protecting portion 408 and a peripheral securing portion 412. The securing portion 412 has an adhesive on its lower surface for securing the wound dressing to a patient's skin. The sensor module 406 is formed integrally with the peripheral securing portion 412 and is connected to a lead 414 which connects the sensor module 406 to a monitoring device, such as that shown in FIG. 10A (described below). In the described embodiment, the wound dressing 404 is an island-type dressing. The thickness of the central portion 408 may include one or more component parts between a lower wound contact layer and the upper layer (seen in FIGS. 9A and 9B).

Figure 9B:
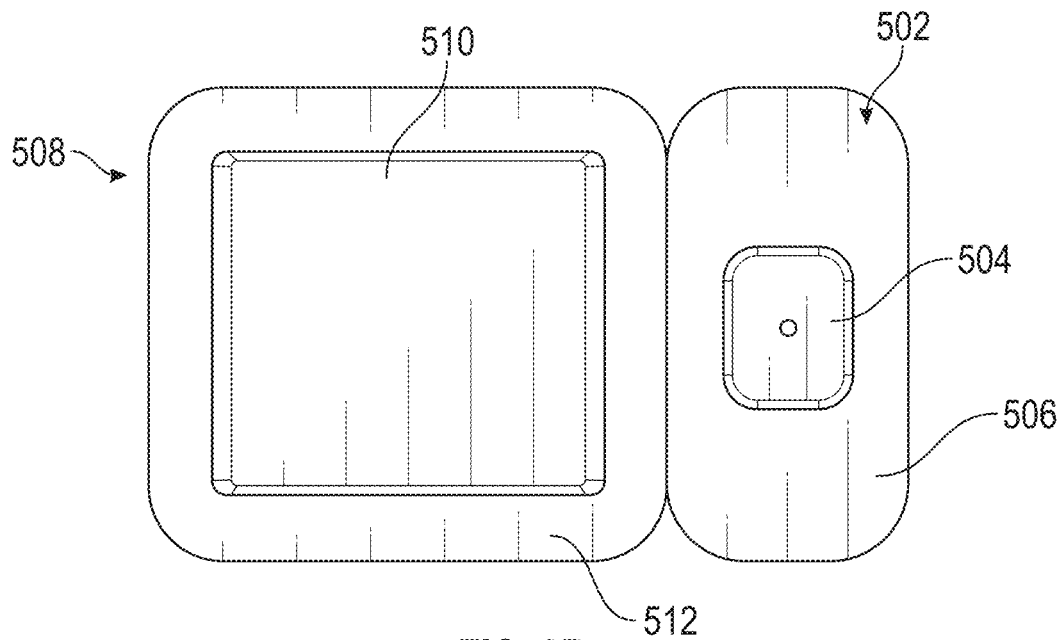
FIG. 9B shows an example of an arrangement comprising a wound dressing and a separate skin perfusion pressure determination device.

FIG. 9B shows an embodiment a skin perfusion pressure determination device 502 comprising a sensor module 504, that is in accordance with the sensor module 14 shown in FIG. 2, and a securing portion 506 with which the sensor module 504 is formed integrally. The device 502 can be secured to a patient's skin adjacent a wound dressing 508 comprising a wound protecting portion 510 and a peripheral securing portion 512, as shown in FIG. 9B. An advantage of the arrangement is that the wound dressing 508 can be changed periodically without having to disturb the skin perfusion pressure determination device 502. In the embodiment shown, the skin perfusion pressure determination device 502 is wireless, and may be configured to communicate with a monitoring device such as that shown in FIG. 10B (described below).

Figure 10A:
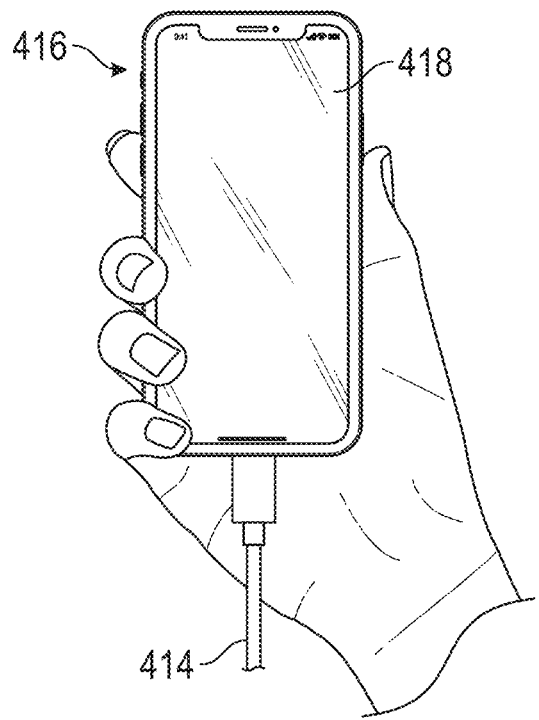
FIG. 10A shows a display device for use with the skin perfusion pressure determination device shown in FIG. 9A.

FIG. 10A shows an example of a monitoring device 416 in the form of a personal hand-held device which is connected to a sensor module by the lead 414 which may be used in conjunction with the skin perfusion pressure determination device 402 shown in FIG. 9A. The monitoring device 416 has an integrated display 418 and may be a portable computer having an integrated display such as a tablet, smartphone or the like. The monitoring device 416 may be carried by a clinician and connected to a wound dressing 404 during a consultation with a patient. The device 416 can then be used to display information about the wound to a clinician and/or stored on the device for future reference or subsequent transfer to a remote database.

Figure 10B:
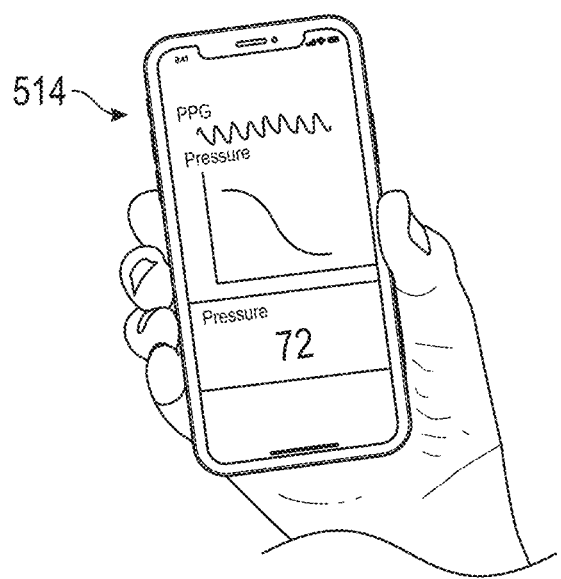
FIG. 10B shows a wireless display device for use with the skin perfusion pressure determination device shown in FIG. 9B.

FIG. 10B shows an example of a monitoring device 514 in the form of a personal hand-held device that is similar to the device shown in FIG. 10A, but is configured to communicate wirelessly with the skin perfusion pressure determination device 502 shown in FIG. 9B.

Figure 11:
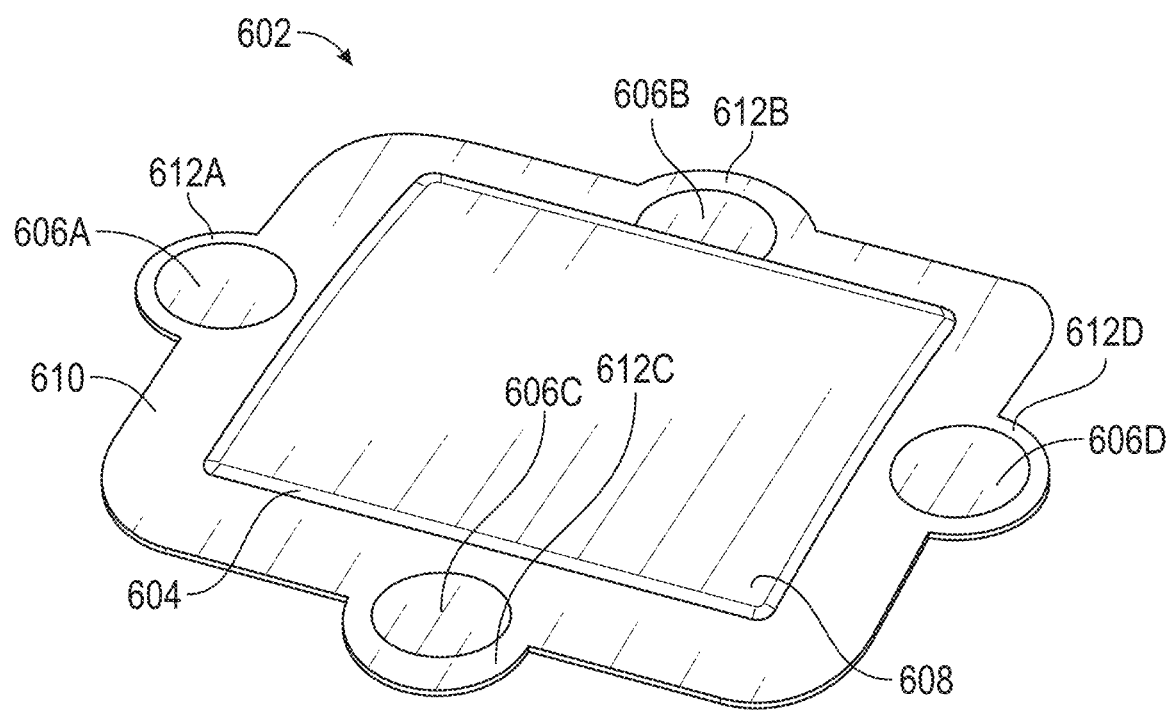
FIG. 11 shows a further embodiment of a skin perfusion pressure determination device comprising a wound dressing and multiple sensor modules.

FIG. 11 shows a skin perfusion pressure determination device 602 comprising a wound dressing 604 having four integrated sensor modules 606A, 606B, 606C, 606D which are each in accordance with the sensor module 14 shown in FIG. 2. The wound dressing 604 comprises a central wound protecting portion 608 and a peripheral securing portion 610. The securing portion 610 has an adhesive on its lower surface for securing the wound dressing to a patient's skin. The sensor modules 606A, 606B, 606C, 606D are formed integrally with the peripheral securing portion 610 and are located at respective lobes 612A, 612B, 612C, 612D. The lobes 612A, 612B, 612C, 612D are spaced apart about the wound protecting portion 608 so that each lobe 612A, 612B, 612C, 612D is spaced opposite one of the other lobes 612A, 612B, 612C, 612D. Other protruding element distribution patterns could of course be utilized.

Figure 12:
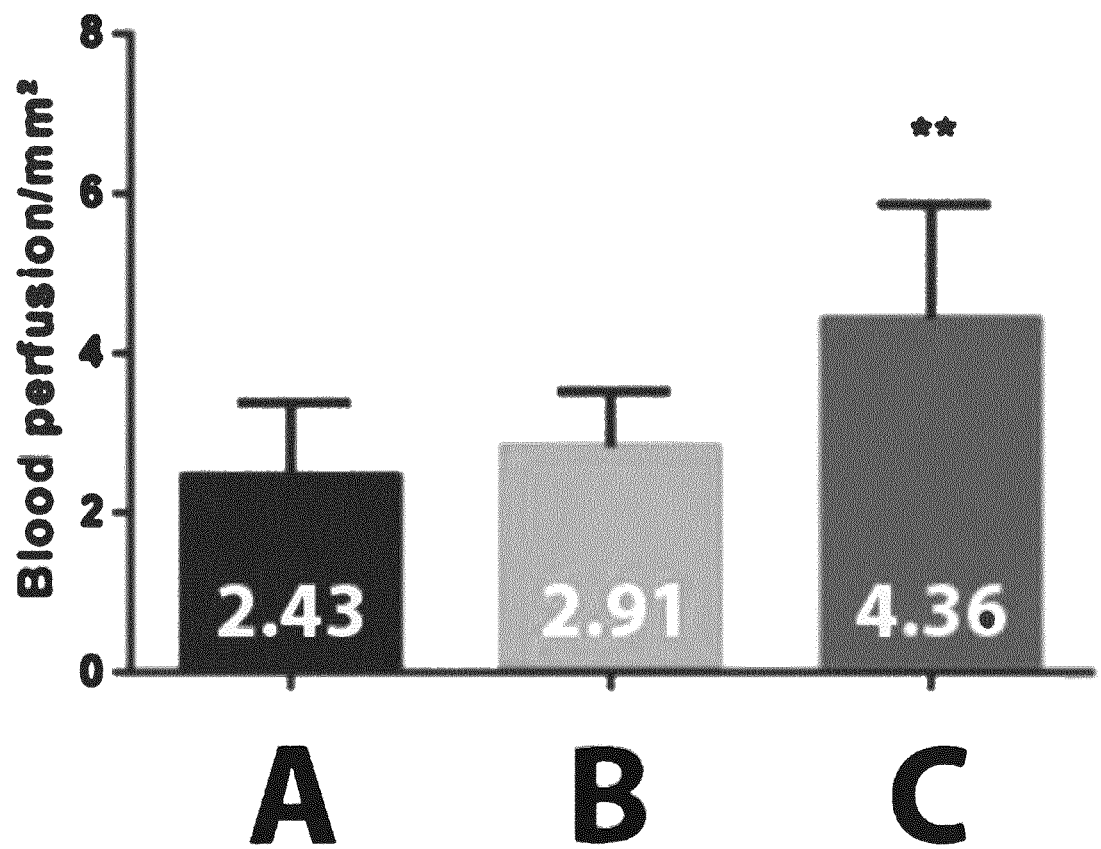
FIG. 12 shows an example display output for the device shown in FIG. 11.

FIG. 12 is an example of a graphical display of information derived from outputs from three of the sensor modules 606A, 606B, 606C (represented by columns A, B and C of the display) shown in FIG. 11. The display provides an indication of how blood perfusion pressures derived from each of the sensor modules 606A, 606B, 606C modules can be displayed together to provide an indication of how blood perfusion pressure may vary about the periphery of a wound to which the dressing 604 is applied.

Figure 13:
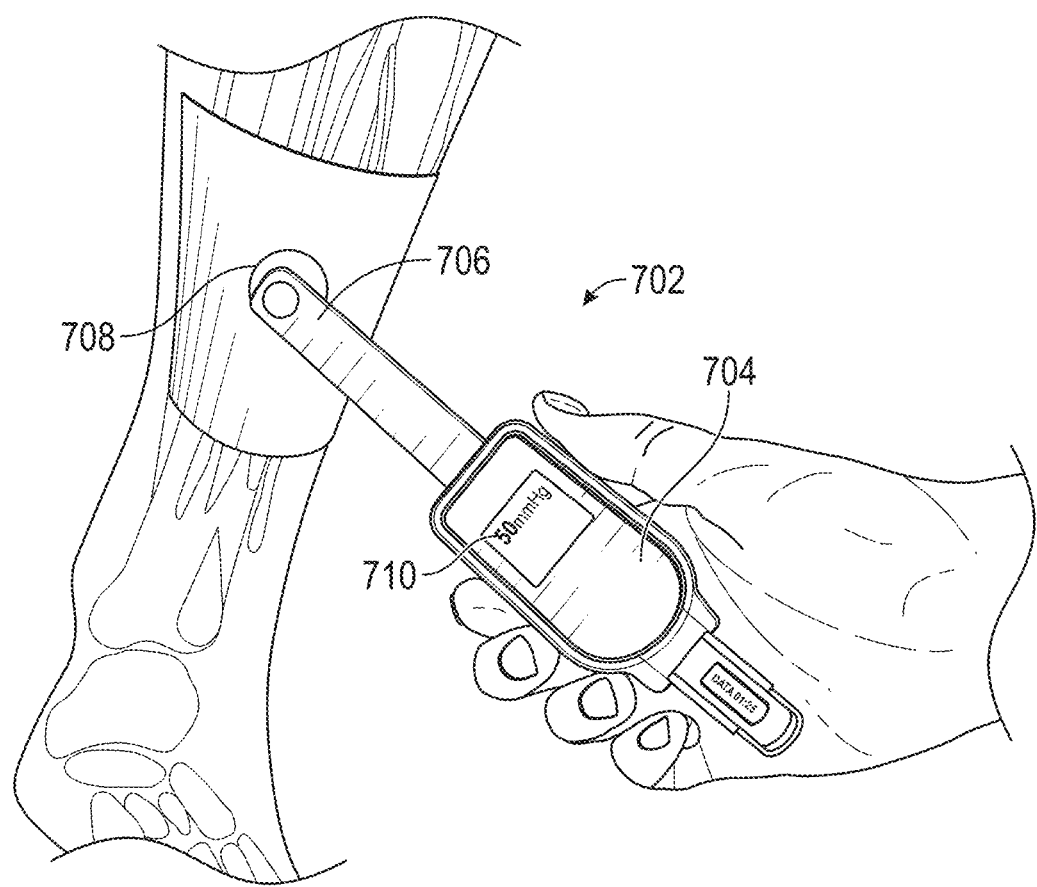
FIG. 13 shows a handheld skin perfusion pressure determination device incorporating a display.

FIG. 13 shows an example of a further embodiment of hand-held skin perfusion pressure determination device 702 comprising a grip portion 704 and a probe portion 706. The device 702 is similar to the device shown in FIG. 6 in that the probe portion 706 comprises a pad portion 708 in which a sensor module is housed. The grip portion 704 comprises an integrated display 710 for displaying information derived from the output of the sensor module.

Figure 14:
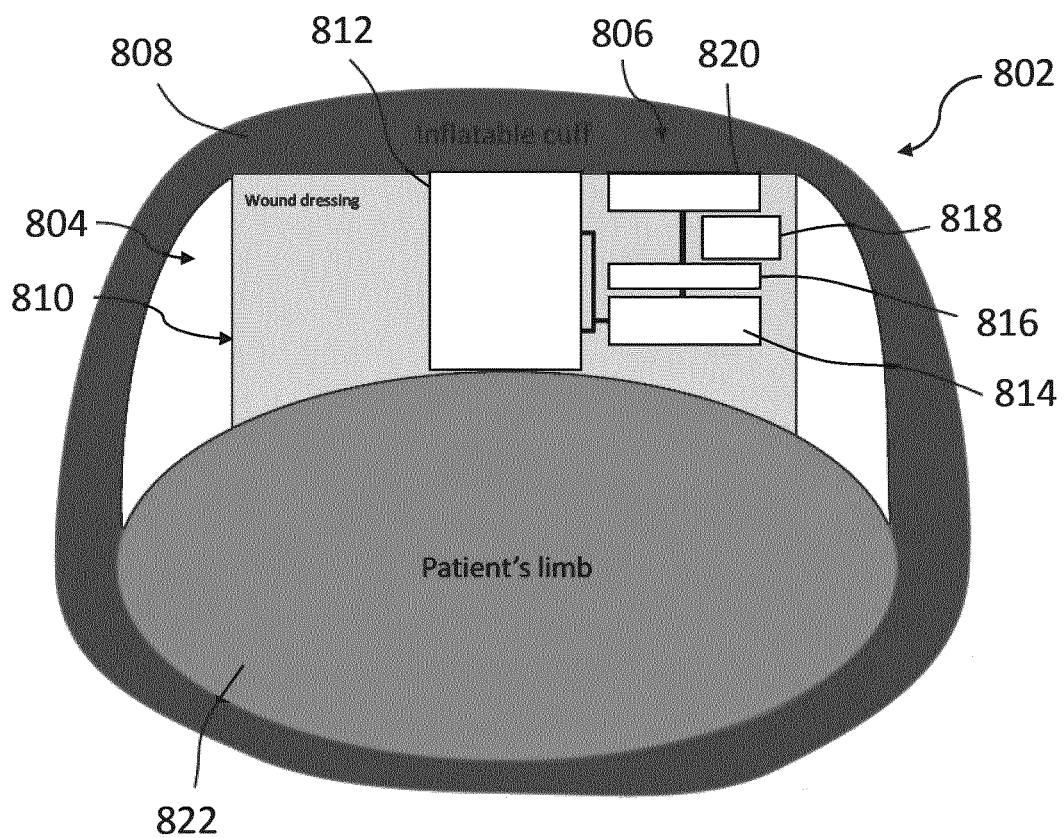
FIG. 14 is a schematic representation of a further embodiment of an apparatus comprising a skin perfusion pressure determination device.

FIG. 14 shows a further apparatus 802 for determining skin perfusion pressure comprising a skin perfusion pressure determination device 804, a monitoring device 806 and an inflatable cuff 808. The skin perfusion pressure determination device 804 comprises a wound dressing 810 and a sensor module 812 formed integrally with the wound dressing 810. The sensor module 812 is in accordance with the sensor module 14 shown in FIG. 1. The monitoring device 806 comprises signal processing electronics 814, a processor 816, a power source in the form of a battery 818 and a display 820. The battery 818 is arranged to supply power to the sensor module 812, processor 816 and display 820. The monitoring device 806 is formed integrally with the wound dressing.

The inflatable cuff 808 is arranged so that, in use, the cuff 808 surrounds the wound dressing 810 and a patient's limb 822 or other region of a patient's body to which the wound dressing is to be secured. The cuff 808 is configured so that the display 820 is visible to a clinician or other such healthcare professional. For example, a window (not shown) may be provided in the cuff 808 in the vicinity of the display 820. The display 820 may be a thin-film display having a thickness which corresponds to, or is less than, the thickness of the wound dressing 810 and which is suitable for incorporation into the wound dressing.

The cuff 808 may be inflated and deflated using an external pump, such as a hand pump, or a pump integrated into the apparatus 802. Inflation of the cuff 808 presses the sensor module 812 against the patient's limb. The cuff 808 can then be deflated in order to reduce the force applied to the sensor module 812 in accordance with the method outlined above with respect to the apparatus shown in FIG. 1 in order to obtain a skin perfusion pressure measurement. Deflation may be done manually by the user or automatically and follow a predetermined sequence of steps and/or in accordance with other sensed parameters.

Figure 15:
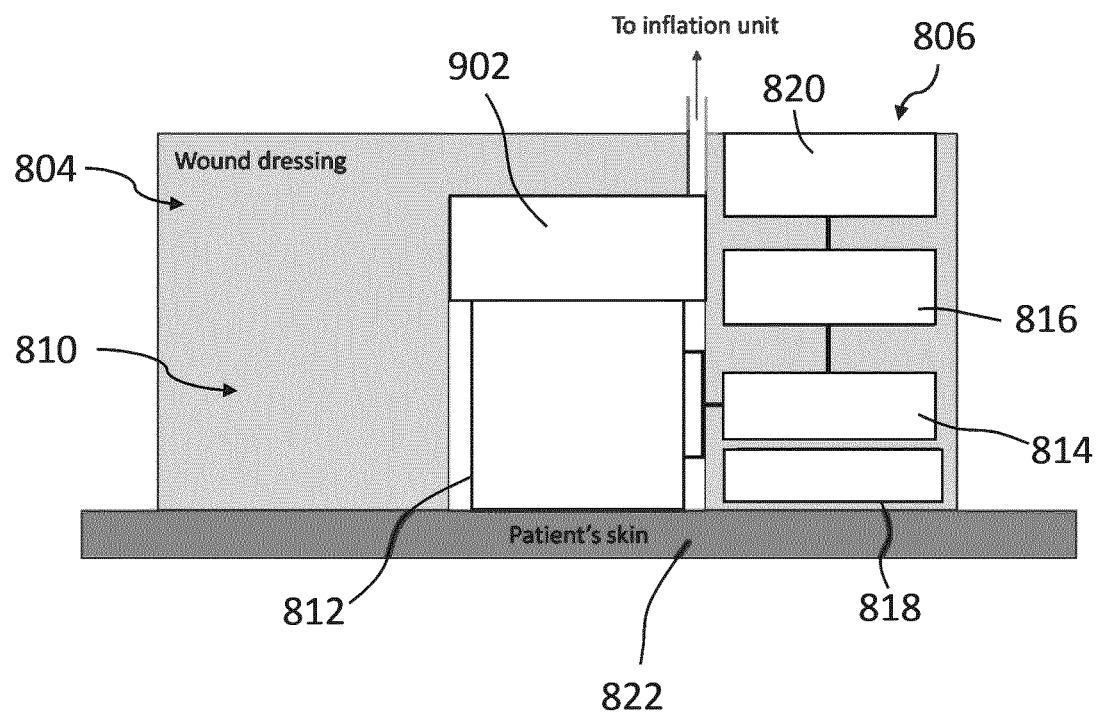
FIG. 15 is a schematic representation of a further embodiment of an apparatus comprising a skin perfusion pressure determination device.

FIG. 15 shows an alternative arrangement of an apparatus comprising a wound dressing and a monitoring device which correspond to the wound dressing and a monitoring device shown in FIG. 14. The same reference signs for the same components have therefore been used. The apparatus further comprises a pneumatic actuator in the form of an inflatable air cushion 902 which is located on top of the sensor module 812 and integrated with the wound dressing 810 such that the air cushion 902 can be inflated to press the sensor module 812 against a patient's skin 822. The apparatus may be configured to automatically take measurements in a predetermined time sequence and store the results to compile data between visits by a clinician or caregiver. The device could further be configured to calculate trends and store them for subsequent retrieval by a caregiver.

Figure 16:
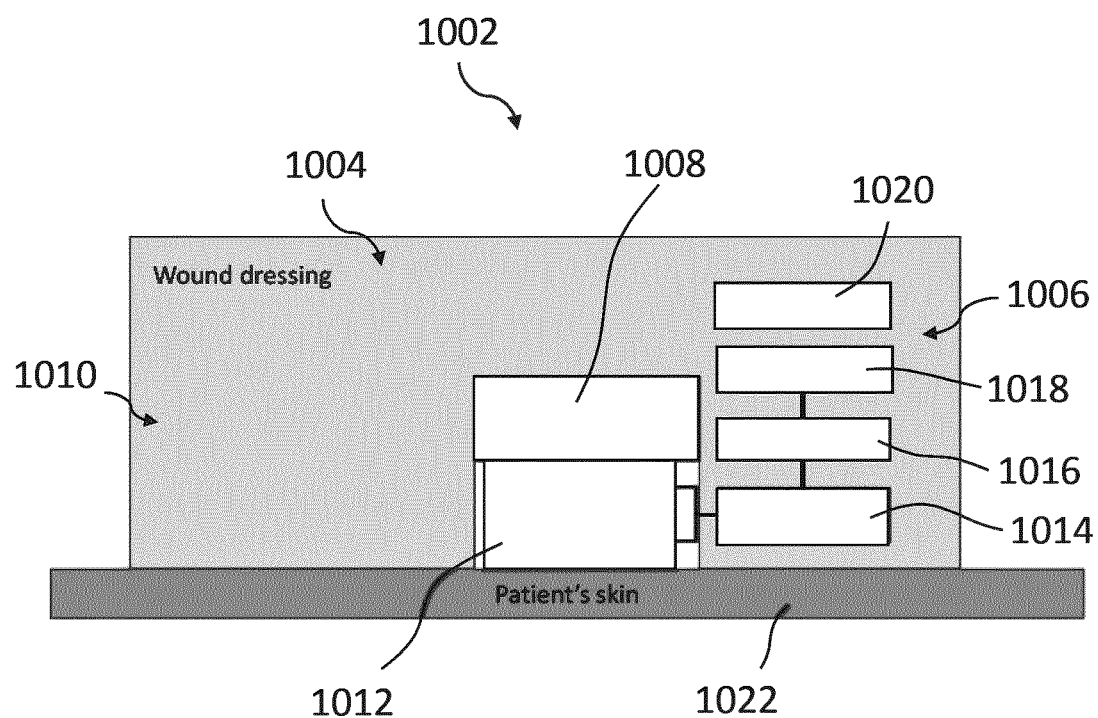
FIG. 16 is a schematic representation of a further embodiment of an apparatus comprising a skin perfusion pressure determination device.

FIG. 16 shows a further apparatus 1002 for determining skin perfusion pressure comprising a skin perfusion pressure determination device 1004, a monitoring device 1006 and a force actuator 1008. The skin perfusion pressure determination device 1004 comprises a wound dressing 1010 and a sensor module 1012 formed integrally with the wound dressing 1010. The sensor module 1012 is in accordance with the sensor module 14 shown in FIG. 1. The monitoring device 1006 comprises signal processing electronics 1014, a processor 1016, a data storage device in the form of a memory 1018 and a power source in the form of a battery 1020. The battery is arranged to supply power to the sensor module 1012, the processor 1016 and the memory 1018. The monitoring device 1006 is formed integrally with the wound dressing 1010. The force actuator 1008 may be an electromechanical actuator, a thermal actuator or a pneumatic actuator such as an air cushion as described with respect to the arrangement shown in FIG. 15, which is arranged to press the sensor module 1012 against a patient's skin 1022. Examples of suitable actuators include: motors, solenoids, shape-memory actuators, wax actuators and piezo-electric actuators or the like. The force actuator 1008 may be calibrated such that the force applied can be determined from the a drive signal supplied to the force actuator. In such embodiments, no additional force sensor may be required.

The processor is configured to both drive the force actuator 1008 and to process outputs from the sensor module 1012 (although separate processors may be used instead) and is programmed to conduct a series of skin perfusion pressure measurements automatically in accordance with a predetermined requirement such as a predetermined time pattern or on an ad hoc basis when initiated by a user. The memory is configured to store data obtained from the sensor module 1012. The stored data can be subsequently transmitted to a further device for storage and/or processing, for example, during consultations with a clinician. This may be done via a wired link or wirelessly.

FIGS. 14, 15 and 16 show a power source in the form of a battery. However, alternative power sources may be used such as one or more capacitors, fuel cells or energy generators, which generate energy, for example, from the movement of the wearer, e.g. based on some piezo elements or the like, from temperature differences and heat generated by the user or the environment, using, for example, thermopiles, or from light, using, for example, photovoltaic cells, or other energy generating systems, for example clockwork type mechanisms which can be charged by the user. Any battery used may be non-rechargeable or rechargeable. Recharging may be conducted using wired or contactless charging techniques.

Figure 17A:
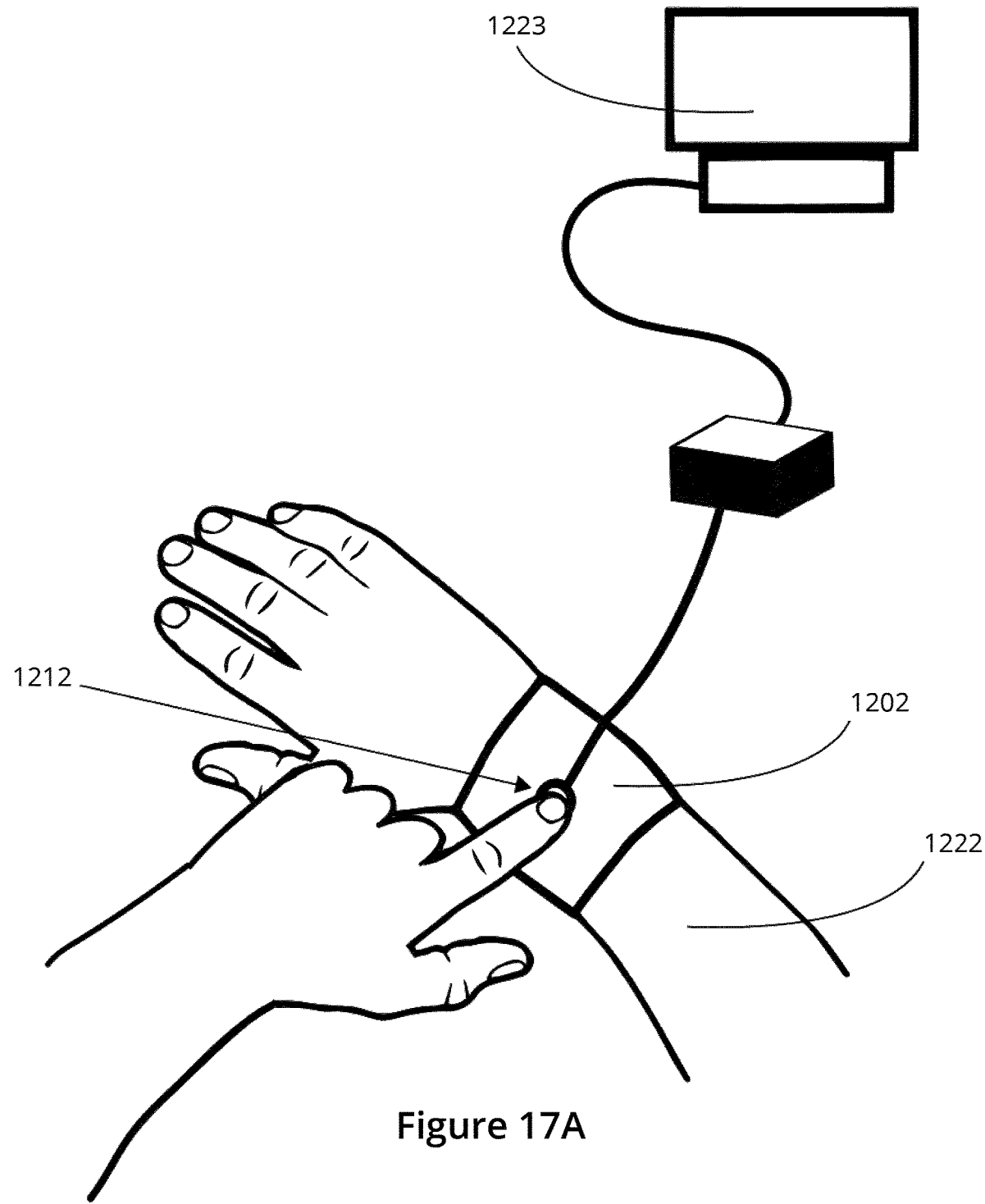
FIGS. 17A-17B and 18A-18B illustrate embodiments of a skin perfusion pressure determination device in use.

FIG. 17A illustrates an embodiment of a cuff 1202. As used herein, the terms cuff and detachable band can be used interchangeable to refer to a detachable band that may be secured to the limb or body of a patient by wrapping it around the limb or body and securing opposite end portions together using a fastener, such as an adhesive strip or hook and loop fastener or the like. The cuff 1202 can have a sensor module 1212 similar to and is in accordance with the sensor module 14 shown in FIG. 1. In some embodiments, manual actuation can be used to apply pressure to the cuff 1202 and press the sensor module 1212 against a patient's limb or other region of a patient's body to which the device is to be secured. The manual actuation can utilize a user's hand and/or fingers to control the amount of force applied to the device and/or patient's skin. FIG. 17A illustrates a cuff 1202 surrounding a patient's limb 1222. The user can press the cuff 1202 at the position of the sensor module 1212 as shown in FIG. 17A. The sensor module 1212 can be pressed against the patient's limb 1222. The pressure asserted on the sensor module 1212 can be released in order to reduce the force applied to the sensor module 1212. These steps can be conducted in accordance with the method outlined above with respect to the apparatus shown in FIG. 1 and the method shown in FIG. 4 in order to obtain a skin perfusion pressure measurement. Release of the manual pressure may follow a predetermined sequence of steps and/or in accordance with other sensed parameters. As illustrated in FIG. 17A, in some embodiments, the device can communicate with a remote device 1223 which displays the results and provides user feedback as described in more detail herein.

Figure 17B:
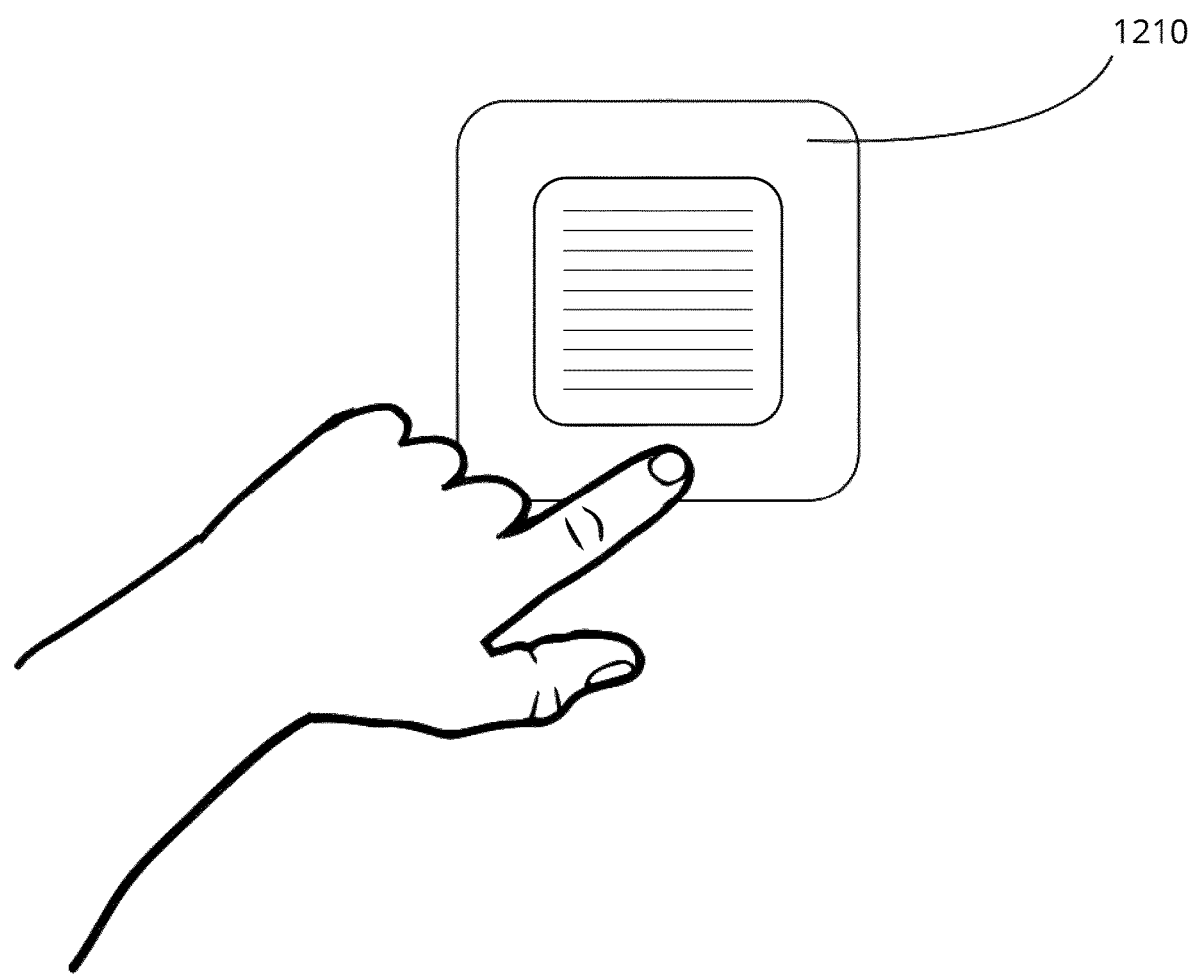

In some embodiments, the sensor module (not shown) can be integrated into the wound dressing 1210. A user can press the sensor module within the wound dressing 1210 to carry out a measurement as illustrated in FIG. 17B.

Figure 18A:
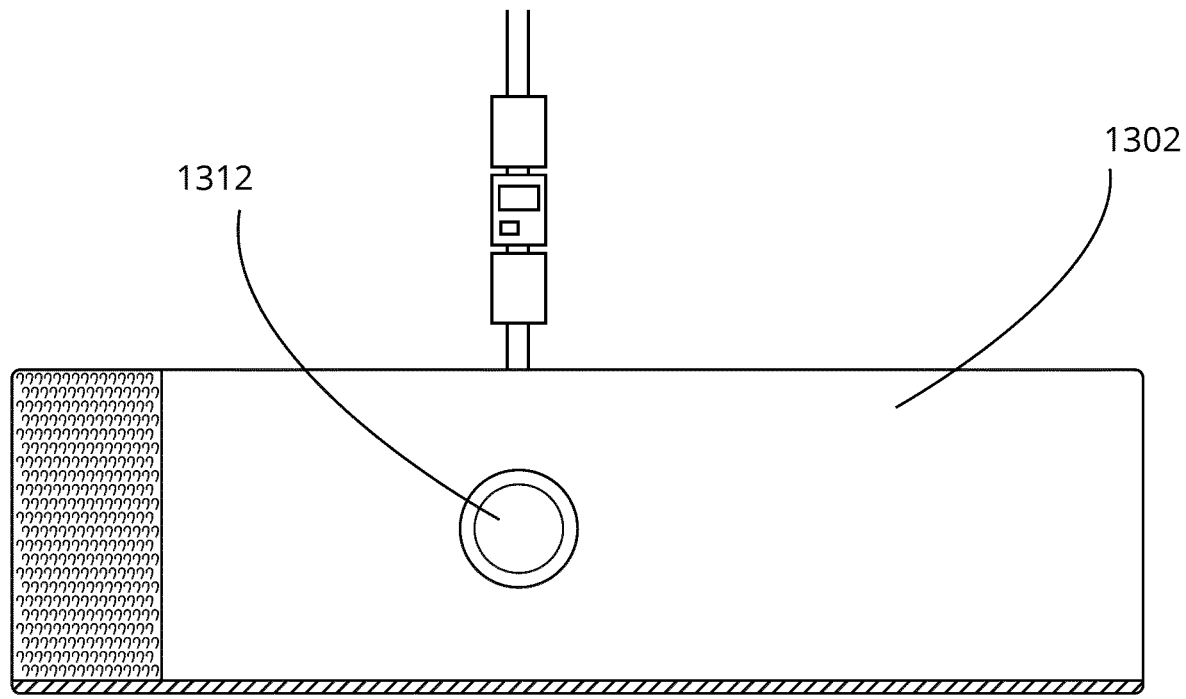
Figure 18B:
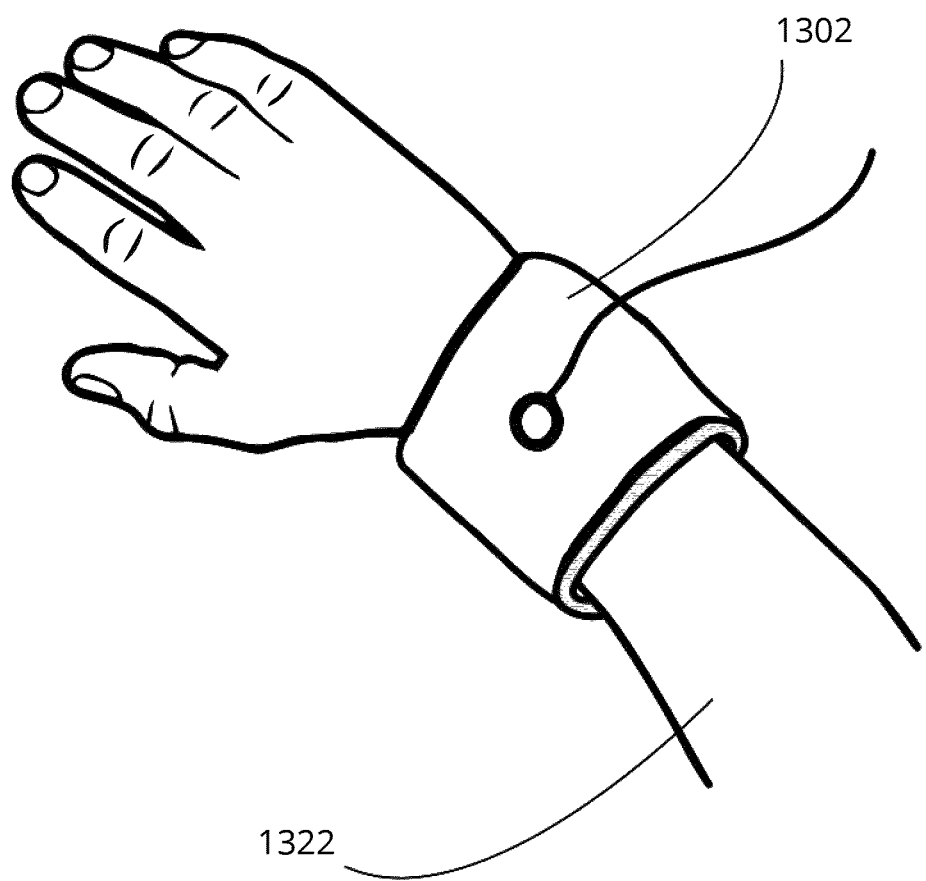

FIGS. 18A and 18B illustrates embodiments of a cuff 1302 with a sensor module 1312 to be used against a patient's limb 1322 or other region of a patient's body to which the device is to be secured. In some embodiments, the cuff 1302 can apply pressure and release pressure against a patient's skin in accordance with the method outlined above with respect to the apparatus shown in FIG. 1 and the method shown in FIG. 4 in order to obtain a skin perfusion pressure measurement.

In some embodiments, the application and release of pressure on a sensor module can be fully automated in order to obtain a skin perfusion pressure measurement. The cuff can use electromechanical actuators which can control the cuff as is shrinks around a patient's limb. Once the appropriate pressure has been applied to the patient's limb, the cuff can automatically release the pressure. In other embodiments, the cuff 1302 can use fluid-based inflatable pads or devices to control the inflation and/or release of pressure on the cuff 1302 by inflating and deflating the cuff 1302 as shown in FIG. 18B. FIG. 18B illustrates the cuff 1302 in an inflated state around a patient's limb 1322. The automated application and/or release of pressure may follow a predetermined sequence of steps and/or can occur in accordance with other sensed parameters.

As described previously, the hand-held skin perfusion pressure determination device or other device with a sensor module can be used to obtain a skin perfusion pressure measurement. The hand-held skin perfusion pressure determination device or other device with a sensor module described herein can be placed either above, below, to the left, and/or to the right of the wound bed to obtain a measurement. In some embodiments, the hand-held skin perfusion pressure determination device or other device with a sensor module can be placed 5 cm from the edge of the wound bed. In some embodiments, the hand-held skin perfusion pressure determination device or other device with a sensor module can be placed about 2 cm to 10 cm from the edge of the wound bed. In some embodiments, measurements can be taken up to the edge of the wound. In some embodiments, measurements can be taken any distance from the wound or from a location on the patient's body not associated with a wound. The skin perfusion measurement can be obtained from one or more locations near or on the wound bed. In some embodiments, the skin perfusion measurement can be obtained from each location, one at a time.

The hand-held skin perfusion pressure determination device or other device with a sensor module can be placed in a first location and measurements can be obtained from the first location in accordance with the methods described herein. Then the hand-held skin perfusion pressure determination device or other device with a sensor module can be placed in a second location and measurements can be obtained from the second location in accordance with the methods described herein. The process can be repeated at each location where a measurement is desired.

In some embodiments, the hand-held skin perfusion pressure determination device or other device with a sensor module can include or be in communication with signal processing electronics and a processor for processing signals received from the sensors in the sensor module. In some embodiments, the hand-held skin perfusion pressure determination device or other device with a sensor module can be connected to or in communication with a monitoring device similar to that shown in FIG. 1. In some embodiments, the processor can display data representing the processed signals on a display. The processor may be configured to display instructions to a patient/clinician on the display such as instructions to increase the applied force or to reduce the applied force at each stage of the measurement process. In some embodiments, the display can be located on a remote device. For example, the display can be located on a computer monitor, laptop, tablet, smart phone, and/or other device with a user interface. In other embodiments, the display can be on the device comprising the sensor module. For example, the display can be located on the hand-held skin perfusion pressure determination device.

FIGS. 19A-19F illustrate embodiments of a display that can provide a user instructions to increase the applied force or to reduce the applied force at each stage of the measurement process. The display 1916 can include an indicator bar 1917. The indicator bar 1917 can rise or increase in size as force is applied to the measurement location or applied with the sensor module. The indicator bar 1917 can fall or decrease in size as the applied force is reduced. In some embodiments, the display can be a computer monitor, laptop, tablet, smart phone, and/or other device with a user interface. FIGS. 19A-19F illustrate a display 1916 with an indication bar 1917 and a hand-held skin perfusion pressure determination device 1902 positioned above or on a wound dressing 1901. While the hand-held skin perfusion pressure determination device 1902 is shown above or on the wound dressing 1901, in some embodiments, the hand-held skin perfusion pressure determination device 1902 could be positioned proximal to the wound dressing 1901. The indication bar 1917 can move between a bottom portion 1918 and a top portion 1919 of the display 1916. FIGS. 19A-19F illustrate embodiments of a wound dressing 1901 and a hand-held device 1902 throughout the steps of the measurement method as described herein. As illustrated in FIGS. 19A-19F, the interaction between the wound dressing 1901 and the hand-held device 1902 can correspond to the movement or location of the indication bar 1917 of the display 1916.

Figure 19A:
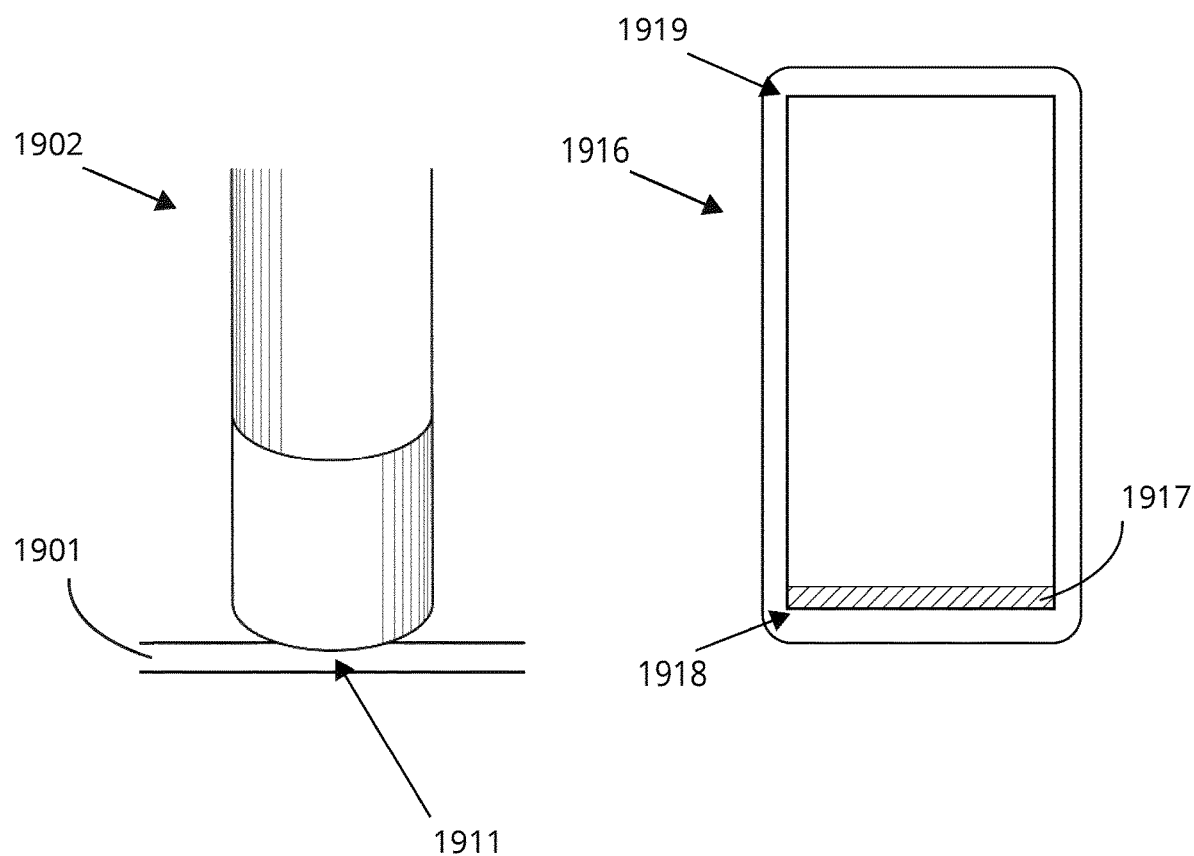
FIGS. 19A-19F illustrate embodiments of a display for use with a skin perfusion pressure determination device and a skin perfusion pressure determination device in use with a wound dressing.

FIG. 19A illustrates a hand-held device 1902 placed on a measurement location or target area 1911 of a wound dressing 1911. As used herein, the measurement location and/or target area are used herein interchangeably to refer to the location where the skin perfusion pressure measurement is taken. The display 1916 shows the indicator bar 1917 near the bottom 1918 of the display 1916. The location of the indicator bar 1917 on the display provides feedback to the user that little to no pressure is applied to the measurement location 1911 by the hand-held device 1902. Pressure can be applied to the measurement location 1911 until the indicator bar 1917 on the display 1906 fills up or rises to the top portion 1919 of the display 1916.

Figure 19B:
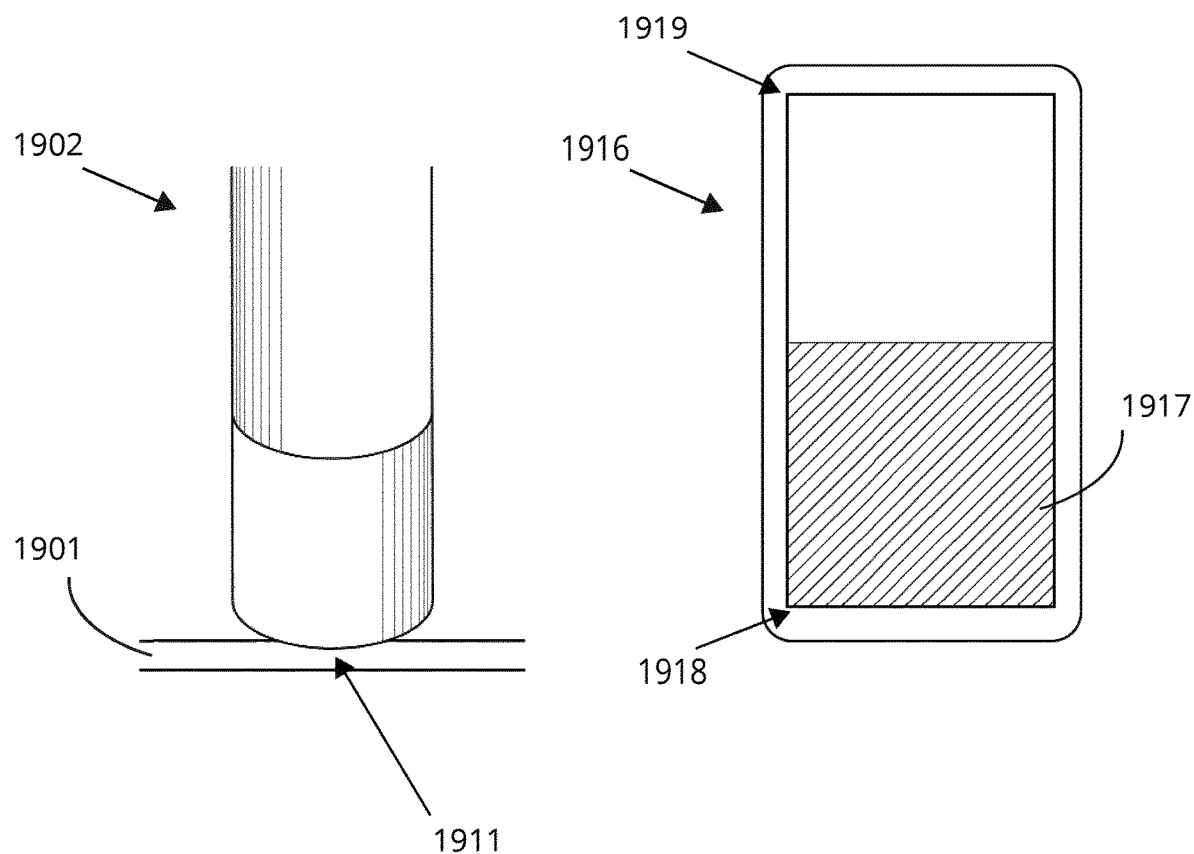

As shown in FIG. 19B, the hand-held device 1902 can be positioned on the measurement location 1911 and a force can be applied to the measurement location 1911. As the force applied to the measurement location 1911 is increased, the indicator bar 1917 on the display 1916 can rise as illustrated in FIG. 19B. In some embodiments, the display 1916 can provide an indicator, symbol, or color change when the incorrect amount or correct amount of force is applied to the measurement location 1911 by the hand-held device 1902.

Figure 19C:
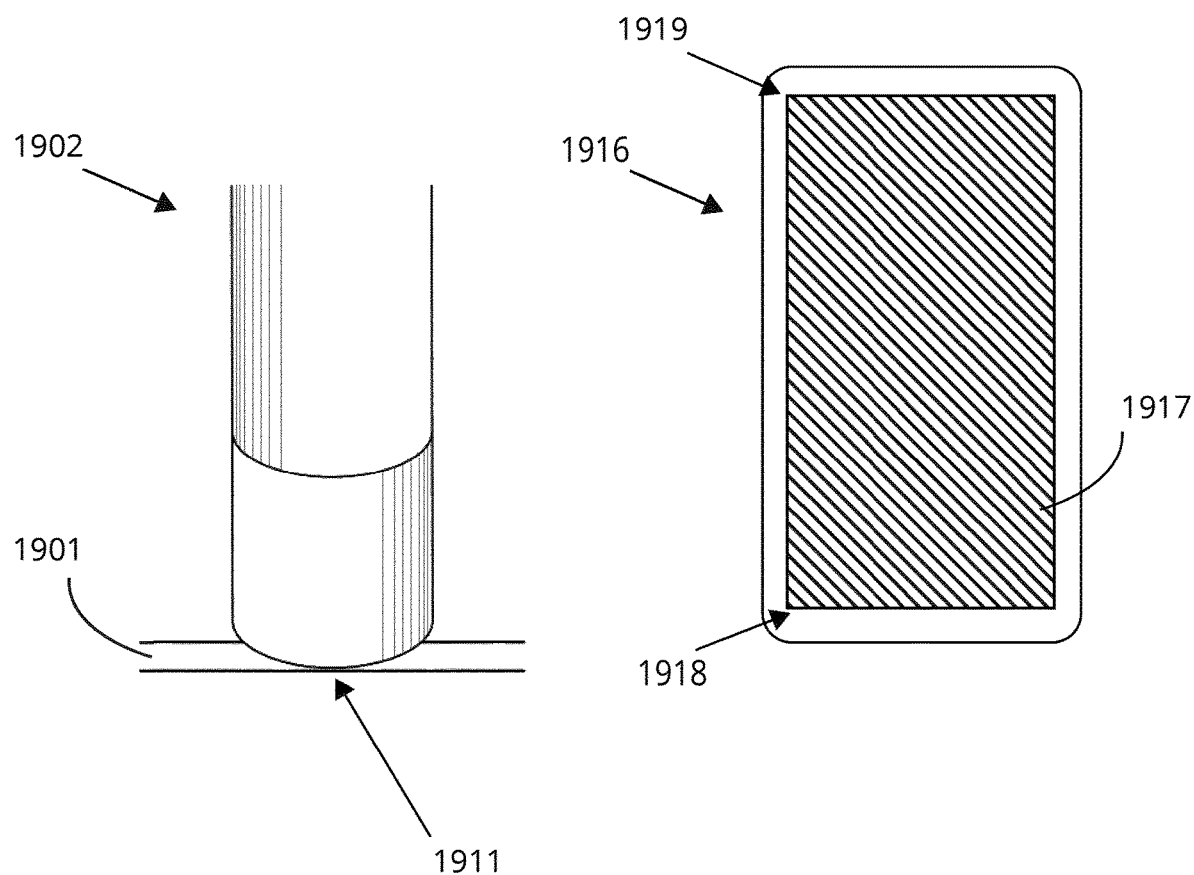

Force can continue to be applied until the indicator bar 1917 on the display 1916 reaches the top 1919 of the display as shown in FIG. 19C. In some embodiments, the indicator bar 1917 can change colors or pattern to indicate the appropriate amount of force has been or is being applied to the measurement location 1911. In other embodiments, a symbol or indicator can be displayed to indicate the appropriate amount of force has been or is being applied to the measurement location 1911.

Figure 19D:
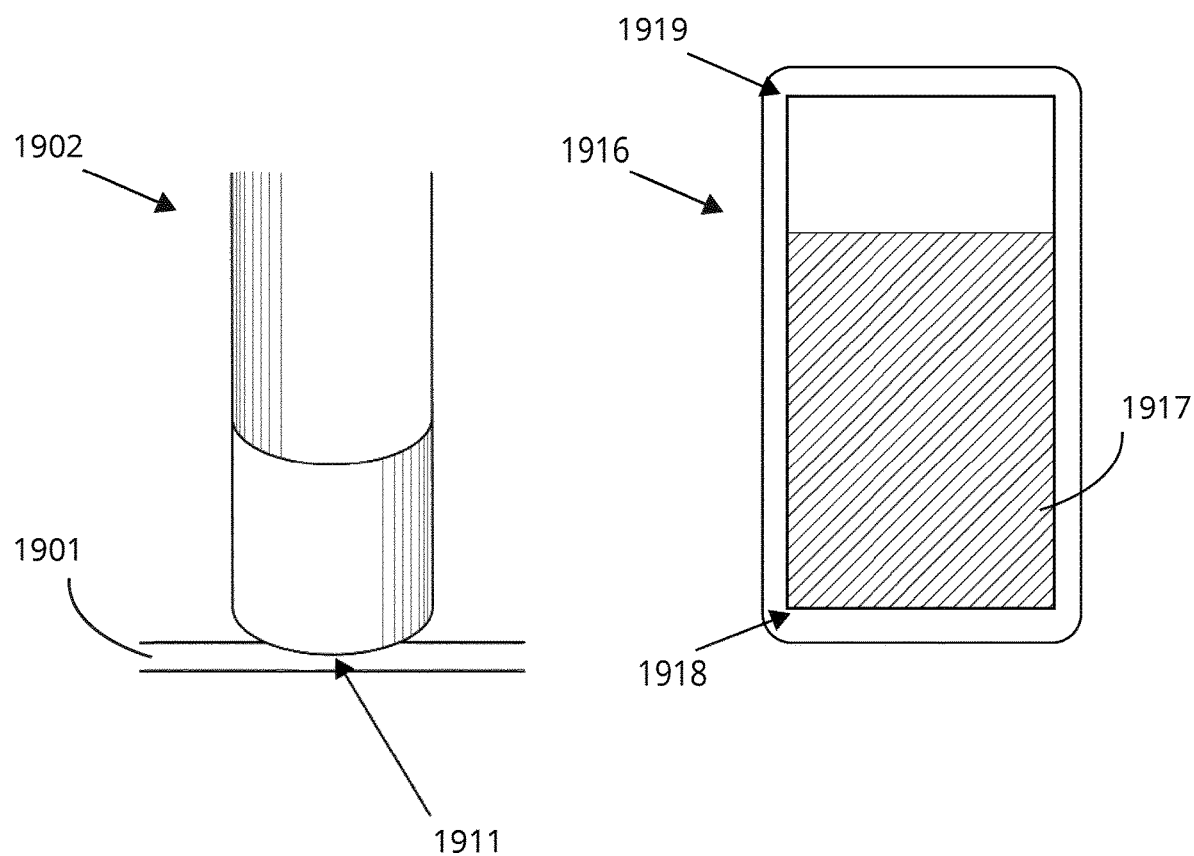
Figure 19E:
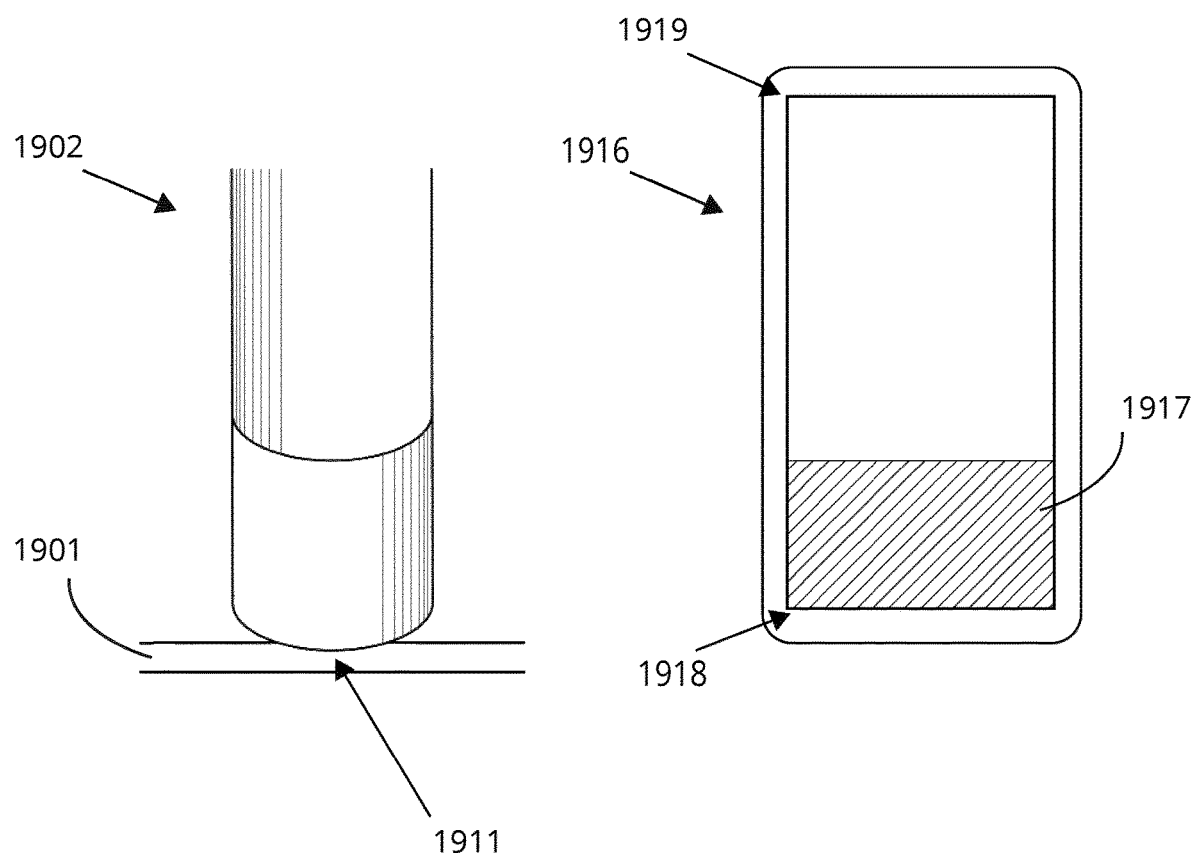
Figure 19F:
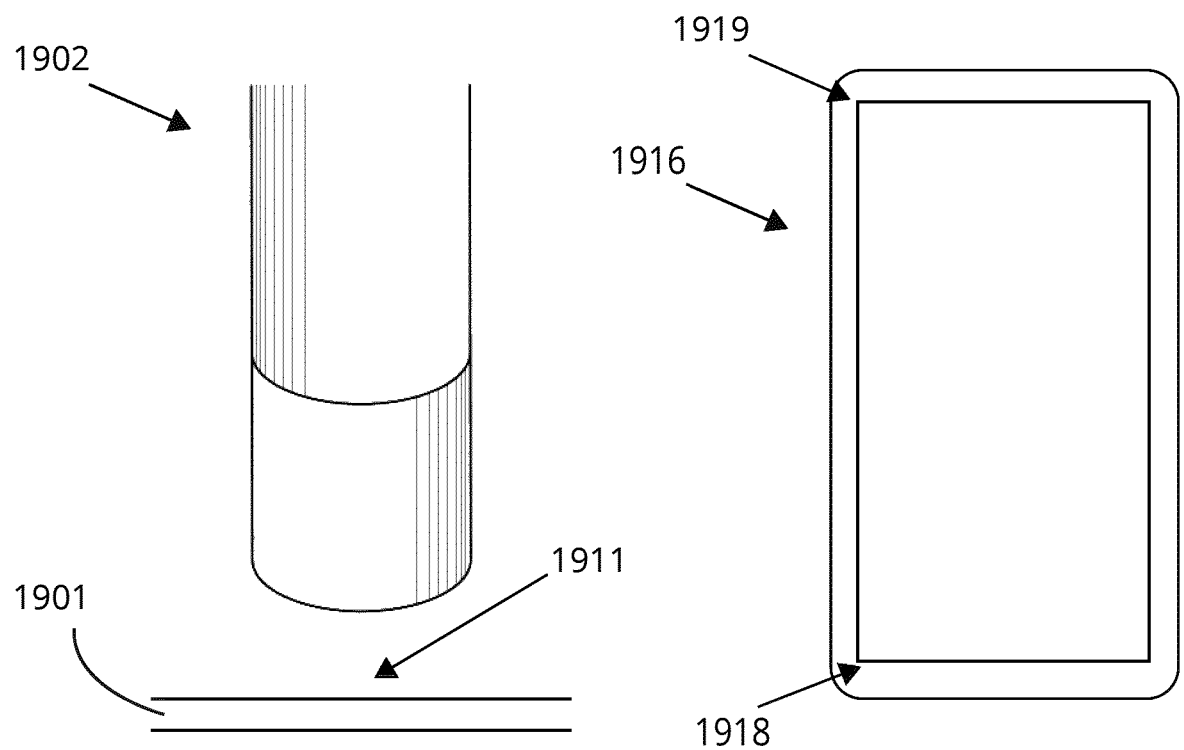

Once the appropriate amount of force has been applied to the measurement location 1911 to conduct the perfusion measurement according to the methods described herein, the force applied by the hand-held device 1902 can be decreased as the hand-held device 1902 is removed from the measurement location 1911 as illustrated in FIG. 19D. In some embodiments, the hand-held device 1092 is slowly removed from the measurement location 1911 to obtain the appropriate measurements. As the hand-held device 1902 is removed from the measurement location 1911, the indicator bar 1917 can begin to decrease or fall as illustrated in FIG. 19D and FIG. 19E. In some embodiments, the indicator bar 1917 can assist the user in slowly removing the hand-held device 1902 from the measurement location. For example, if the indicator bar falls or decreases too quickly the user can adjust to remove the hand-held device 1902 at a slower rate. In some embodiments, the display 1916 can provide an indicator, symbol, or color change if the hand-held device 1902 is removed too quickly or too slowly. As illustrated in FIG. 19F, once the hand-held device 1902 is completely removed from the measurement location 1911, the indicator bar 1917 is no longer present or visible on the display 1916.

The display 1916 can give live or real time feedback on the current amount of pressure being applied versus the pressure that should be applied. The display 1916 and indication bar 1917 can give helpful, education feedback to improve performance for the next use if the first use was insufficient to collect data.

Once the measurement is taken at a first location, the hand-held device 1902 can be applied to a second measurement location and the process can be repeated with the force application instructions provided by the user on the display 1916 as illustrated in FIGS. 19A-19F.

In some embodiments, the display or user interface can be used to provide guidance and/or feedback to a user. In some embodiments, the display or user interface can provide guidance and/or feedback with respect to the measurement location and the applied force to conduct the perfusion measurement according to the methods described herein. In some embodiments, the display can indicate various conditions. For example, the display can provide a visual indication of a measurement location, an applied force, an occlusion reached indication, high force warning, speed of movement indication, perfusion measurement result, and/or a measurement quality indication. In some embodiments, these conditions or indicators can be displayed on a remote display such as a computer monitor, laptop, tablet, smart phone, and/or other device with a user interface. In some embodiments, these conditions or indicators can be displayed on a device comprising a sensor module, for example, a hand-held skin perfusion pressure determination device.

Figure 20A:
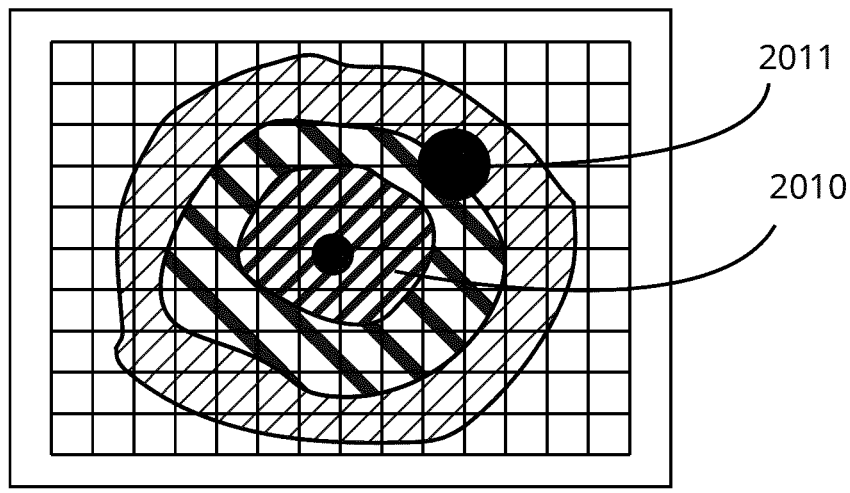
FIGS. 20A-20F illustrate embodiments of a display for use with a skin perfusion pressure determination device.
Figure 20B:
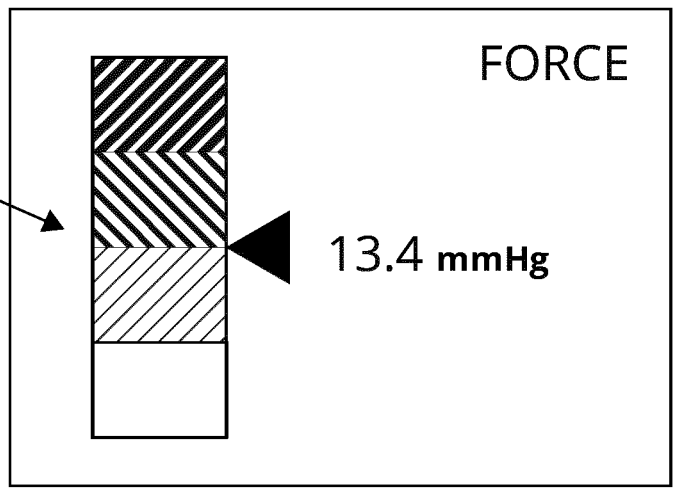

FIG. 20A illustrates an embodiment of a display indicating the location of measurement 2011 with respect to the wound 2010. FIG. 20B illustrates an embodiment of a display or user interface with a force indicator used to indicate the force applied by a skin perfusion pressure determination device or other measurement device to the measurement location. The force indicator can assist the user by indicating when the appropriate amount of force is applied to the measurement location. As illustrated in FIG. 20B, the force indicator display can provide a visual indication of the force applied to the measurement location. The visual indication of the force applied can be indicated with a multi-segment gauge type indicator 2012 as illustrated in FIG. 20B.

Figure 20C:
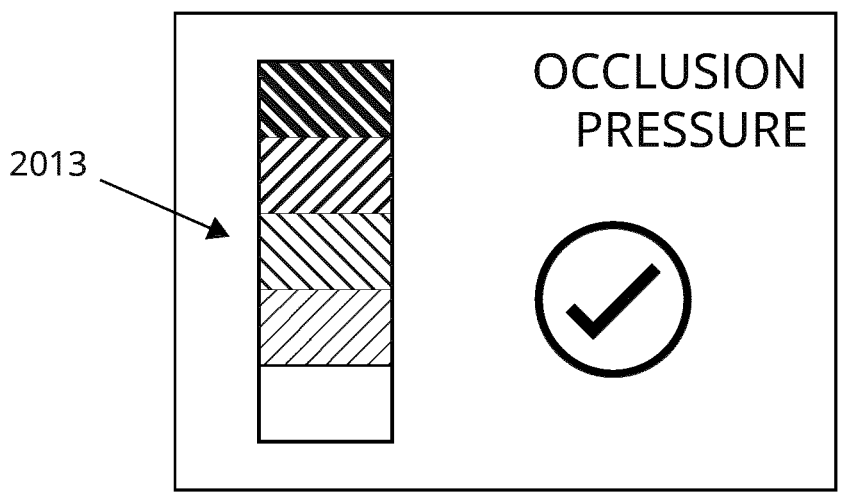

FIG. 20C illustrates an embodiment of an occlusion pressure indicator. The occlusion pressure indicator can provide a visual indication of the occlusion pressure and/or when the occlusion pressure is reached. The occlusion pressure indicator can assist the user by indicating when the appropriate amount of pressure has been applied to the measurement location to cause occlusion. In some embodiments, the visual indication of the force applied can be indicated with multi-segment gauge type indicator 2013 as illustrated in FIG. 20C.

Figure 20D:
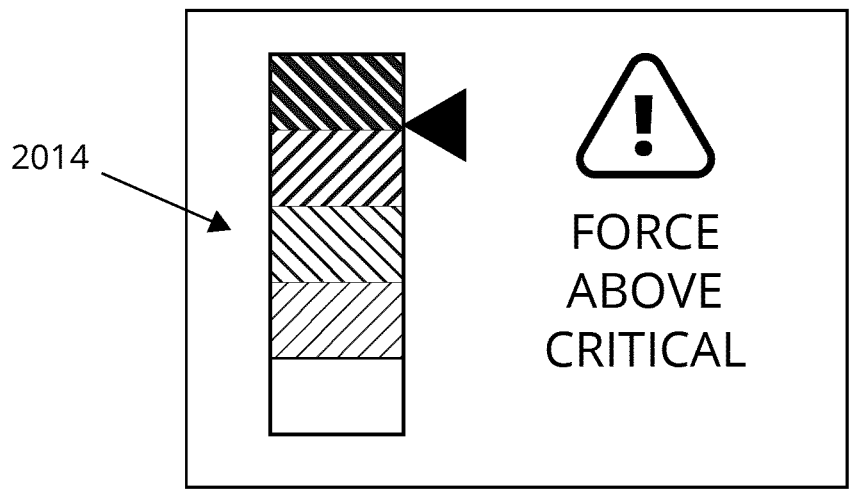

FIG. 20D illustrates an embodiment of a display with a visual indicator used to indicate when a force is above a critical level. In some embodiments, the visual indication of the force applied can be indicated with multi-segment gauge type indicator 2014 as illustrated in FIG. 20C.

In some embodiments, the display can be a high force warning indicator with a two-level indication. The two-level indication can include an indication when occlusion pressure is reached and when the force is above a critical level. In other embodiments, the high force warning can have a three-level indication. The three-level indication can include an indication when occlusion pressure is reached, when force has reached a desired level, and when the force is above a critical level.

Figure 20E:
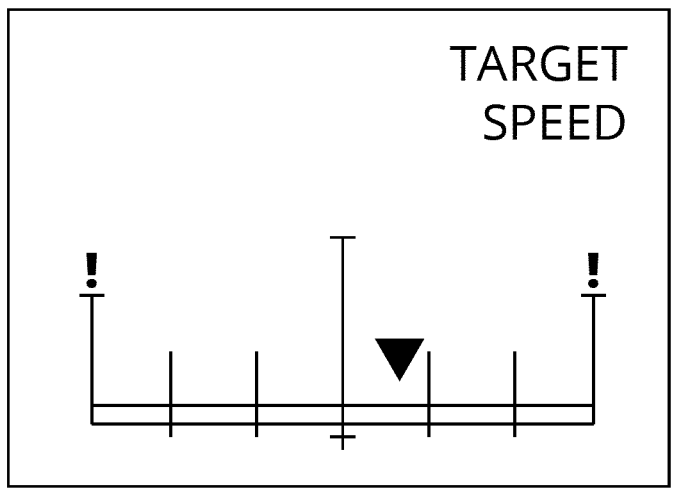

FIG. 20E illustrates an embodiment of a display with a visual indication of the speed of movement of the hand-held device. In some embodiments, the speed of movement indicator can include an indication if the speed is appropriate (for example, target speed), if the speed is too slow, and/or if the speed is too high or fast. In some embodiments, the speed of movement indicator can be a graphical representation of the speed as illustrated in FIG. 20E.

Figure 20F:
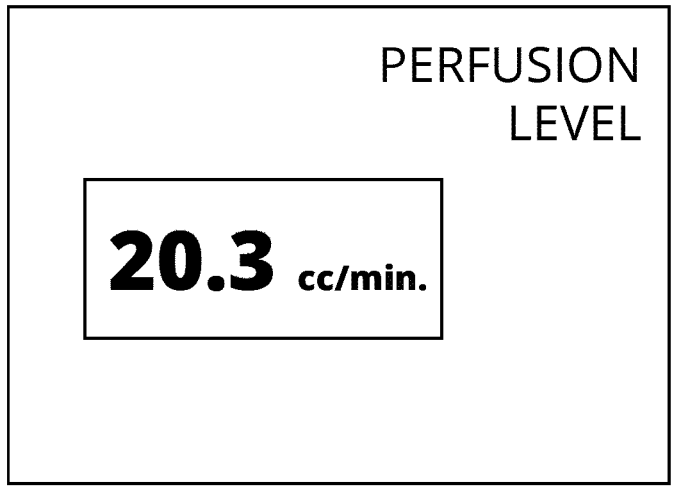

FIG. 20F illustrates a display with a visual indication of a perfusion level and/or perfusion measurement result. In some embodiments, the visual indication of prefusion level and/or perfusion measure results can be displayed with a text and/or numeric indication display as shown in FIG. 20F. For example, perfusion measure result can be expressed in units of pressure.

In some embodiments, the display can include an indication of the quality of the measurement obtained from the measurement location.

Figure 21A:
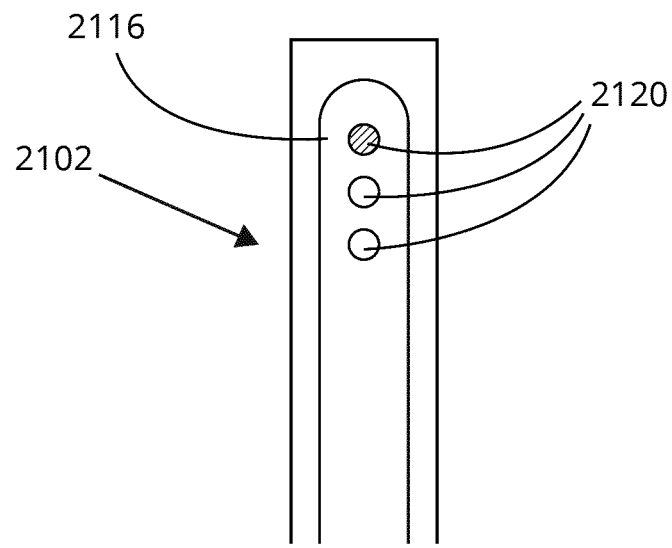
FIGS. 21A-21G, 22A-22E, and 23 illustrate embodiments of a display or user interface on the hand-held skin perfusion pressure determination device.

FIGS. 21A-21G illustrate embodiments of a display or user interface on a hand-held skin perfusion pressure determination device 2102. FIG. 21A illustrates a hand-held device 2102 with a display 2116. In some embodiments, the display 2116 can include one or more visual indicators 2120. In some embodiments, the visual indicators 2120 can include a light source, for example, a light emitting diode (LED). The visual indicators 2120 can be different colors, can change colors, and/or can illuminate in a pattern or sequence to provide guidance or feedback to the user. In some embodiments, multiple visual indicators 2120 can be used to indicate one or more conditions or parameters of the wound dressing or hand-held device. In some embodiments, the light source can be a single color, multi-color, and/or blinking light source.

Figure 21B:
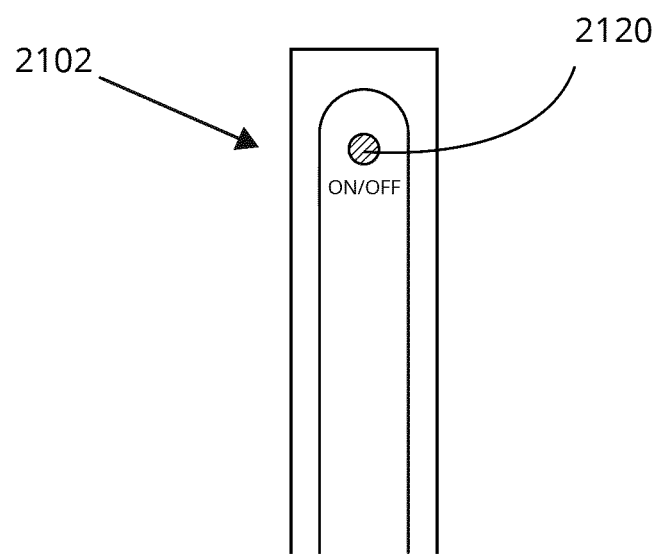
Figure 21C:
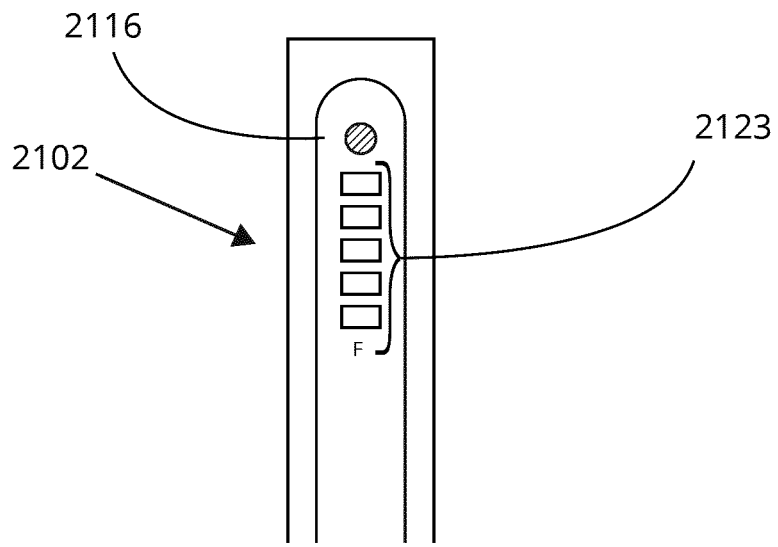

FIG. 21B illustrates a hand-held device 2102 with a visual indicator 2120 for signaling if the device is powered on or off. In some embodiments, the indicator 2120 can display different colors depending on the condition or can switch between being illuminated or not illuminated depending on the condition. FIG. 21C illustrates a hand-held device 2102 with a visual indicator 2123 for indicating that a particular force has been applied. For example, the visual indicator 2123 can indicate when an occlusion force is reached. The visual indicator 2123 can have a force indication displayed with a multi-segment gauge type indicator including a column of light sources that can be illuminated one by one as the force applied to the dressing in increased. As shown in FIG. 21C, the hand-held skin perfusion pressure determination device 2102 can include two types of visual indicators. The display 2016 of the hand-held skin perfusion pressure determination device 2102 can include a circular visual indicator 2120 and the multi-segment gauge type indicator 2123.

Figure 21D:
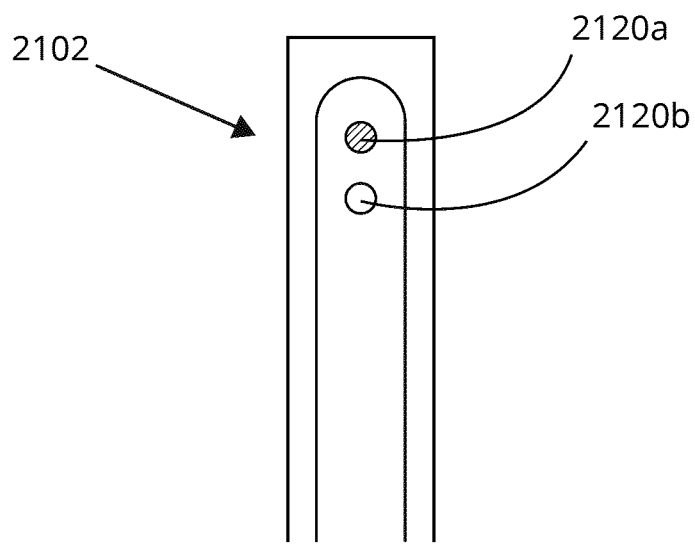
Figure 21E:
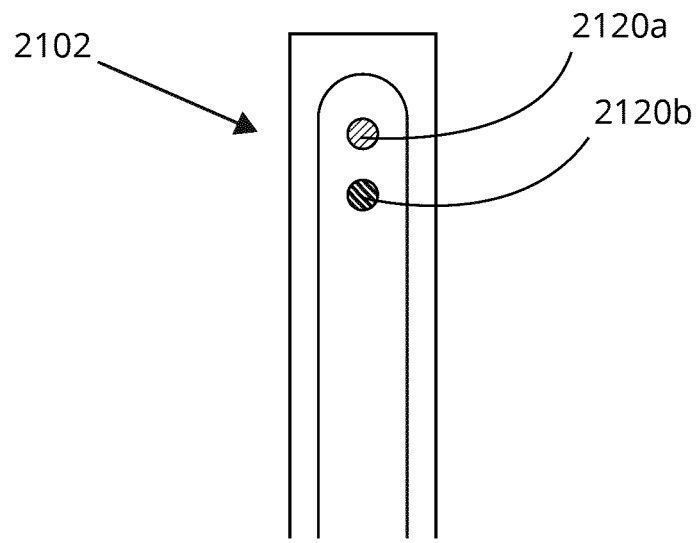

FIGS. 21D and 21E illustrates a hand-held skin perfusion pressure determination device 2102 with two visual indicators 2120*a* and 2120*b*. In some embodiments, the two visual indicators 2120*a* and 2120*b* can indicate when the appropriate speed for application and withdrawal or force is used. To indicate different conditions, the indicators can be illuminated or not illuminated. For example, FIG. 21D illustrates an embodiment of a hand-held device 2102 with indicator 2120*b* not illuminated and FIG. 21E illustrates an embodiment of a hand-held device 2102 with indicator 2120*b* illuminated. In other embodiments, one of the two visual indicators 2120*b* can display a first color when the speed is correct and a second color as when the speed is too high. In some embodiments, the two visual indicators can be used in combination to display or indicate a certain condition. The two visual indicators can display different color combinations and/or illumination combinations depending on the condition.

Figure 21F:
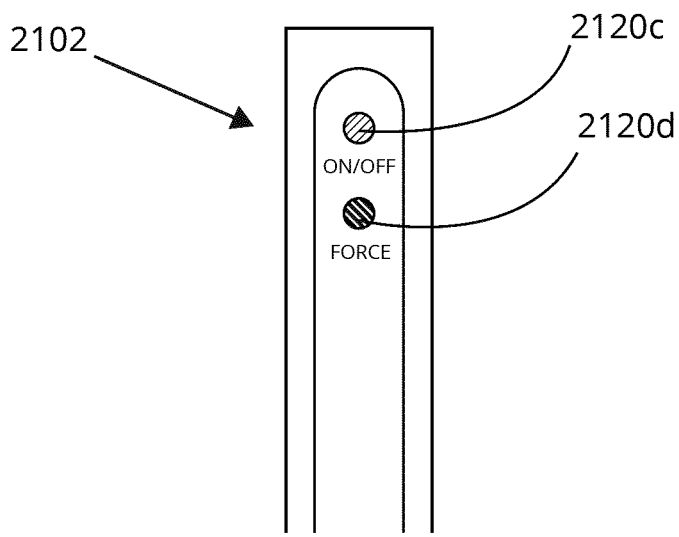

In some embodiments, the two visual indicators 2120*a* and 2120*b* can be used to indicate two different conditions. As illustrated in FIG. 21F, the visual indicator 2120*a* can be used to indicate if the device is on or off and the visual indicator 2120*b* can be used to indicate that the force applied to the measurement location has reached a desired level.

Figure 21G:
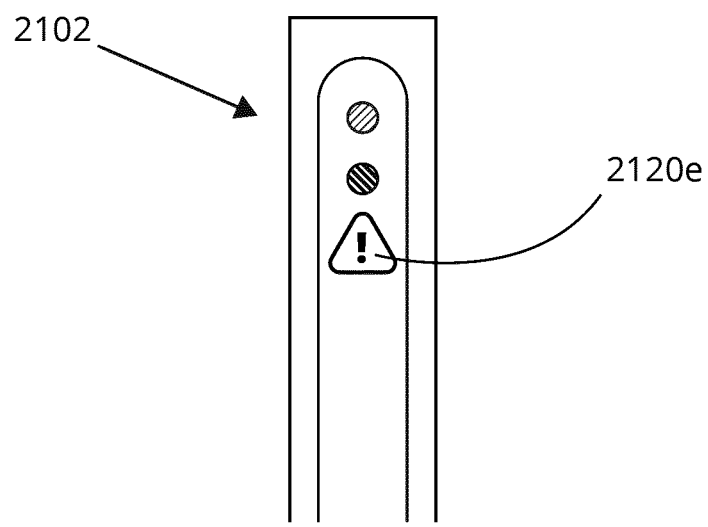

FIG. 21G illustrates an embodiment of a hand-held device 2102 with multiple indicators. Visual indicator 2120*e* can be a caution symbol or other symbol that is illuminated when a condition has occurred. The indicators can be any shape or symbol, a light source, a multi-segment gauge type indicator, and/or any other indicator type.

Figure 22A:
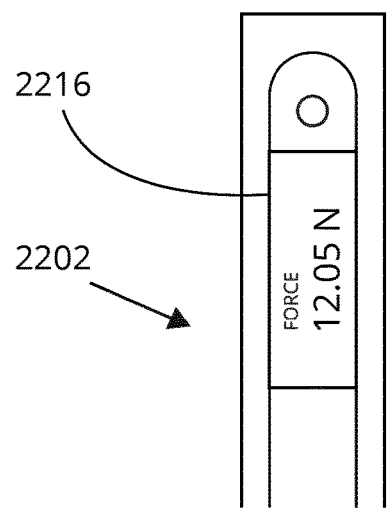
Figure 22B:
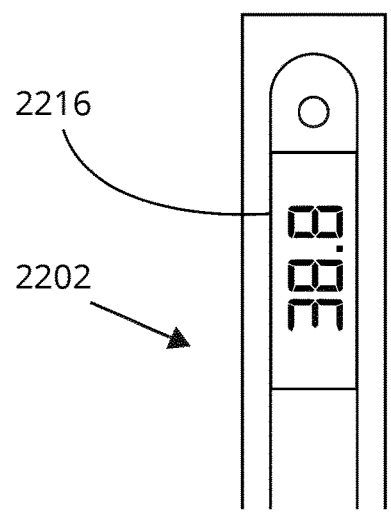

As illustrated in FIGS. 22A and 22B a hand-held skin perfusion pressure determination device 2202 can include a display 2216 that provides a text and/or numeric indication of various conditions of the hand-held skin perfusion pressure determination device, measurement technique, and/or measurement information. For example, the display 2216 can provide a text and/or numeric indication of the force (shown in FIG. 22A), the withdrawal speed (shown in FIG. 22B), or a measurement result.

Figure 22C:
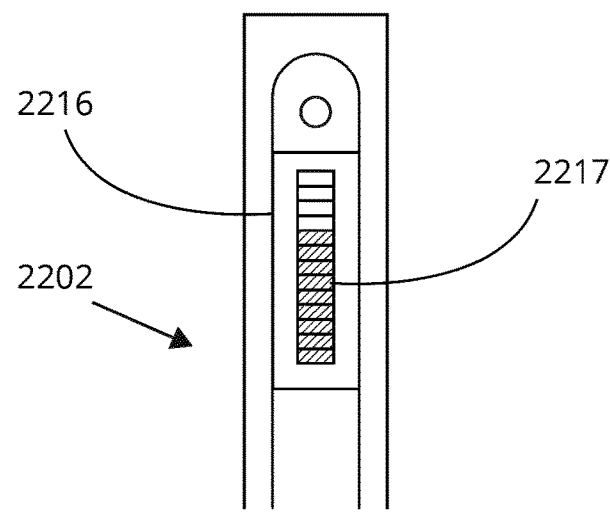
Figure 22D:
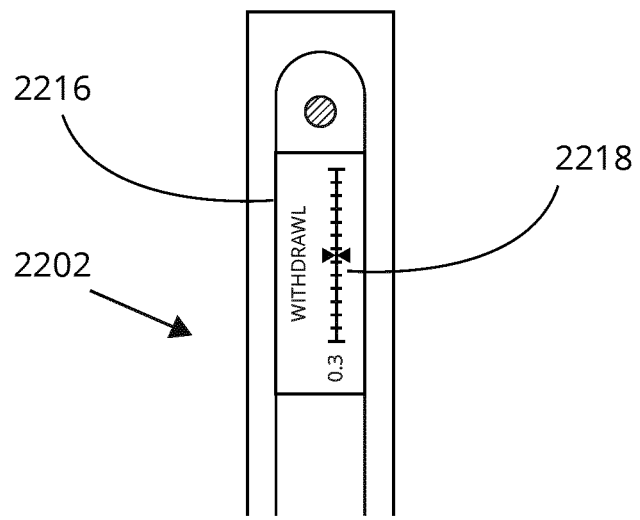
Figure 22E:
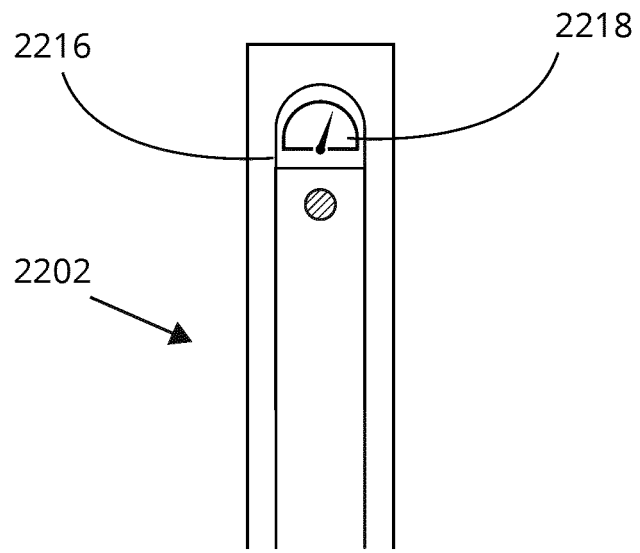

In some embodiments, the hand-held device 2202 can include a display 2216 that provides a graphical indication of various conditions of the hand-held device 2202, measurement technique, and/or measurement information. In some embodiments, the graphical indicator can include multiple visual indicators. In some embodiments, as shown in FIG. 22C, the graphical indicator can be a multi-segment gauge type indicator 2217. In some embodiments, the graphical indicator can be an analogue display 2218 as illustrated in FIGS. 22D and 22E.

In some embodiments, the visual indicators can be LED indicators, organic light emitting diodes (OLED) indicators, and/or electronic paper display technology (EINK) indicators.

An audible and/or tactile indicators can be used in addition to or in place of the visual indicators on the hand-held device. In some embodiments, the audible and/or tactile indicators can provide an audible and/or tactile signals to indicate and/or monitor the force level and/or withdrawal speed. The audible signal or tactile indicator may be generated to inform a clinician/patient of a condition or parameter. In some embodiments, an audible and/or tactile signal can be used to provide warnings or alerts including a warning when the occlusion pressure is reached and/or a high force warning. In some embodiment, the audible signal may be continuous or a series of beeps that vary in frequency or volume depending on the magnitude of the pulsatile component of the trace or when a condition is reached. The tactile signal may be a continuous or series of vibrations that vary in frequency or volume depending on the magnitude of the pulsatile component of the trace or when a condition is reached. For example, an audible beep pattern or vibration pattern may stop when the pulsatile component drops below a threshold value and re-emerges when the pulsatile component returns indicating the return of blood flow in the tissue at the target area.

Figure 23:
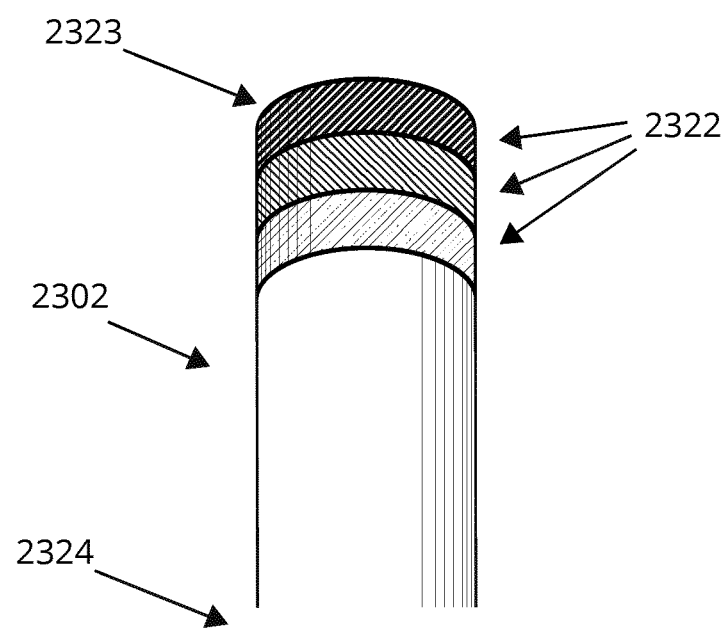

In some embodiments, the indicators can be circumferential indicators. FIG. 23 illustrates an embodiment of a hand-held skin perfusion pressure determination device 2302 with a circumferential indicator 2322. The circumferential indicator 2322 can be located on the distal end 2323 of the hand-held skin perfusion pressure determination device 2302 furthest from the proximal sensor end 2324 of the hand-held device 2302. The circumferential indicator 2322 can indicate one or more characteristics or parameters of the hand-held skin perfusion pressure determination device 2302, the sensor, the measurement location, the measurement method, and/or any other characteristics that can provide guidance or feedback to the user. In some embodiments, the hand-held skin perfusion pressure determination device 2302 can include one or more circumferential indicators 2322 to provide visual force feedback to the user. The visual force feedback can be real time or substantially real time feedback. In some embodiments, each circumferential indicator 2322 can provide guidance or feedback with respect to a different characteristic. For example, a first circumferential indicator can provide guidance to the user regarding a first characteristic and a second circumferential indicator can provide guidance to the user regarding a second characteristic, and so on. In some embodiments, the circumferential indicators 2322 can be used to display the different levels of the same characteristic. For example, a first circumferential indicator can illuminate or provide a visual indication when a first characteristic reaches a first threshold and a second circumferential indicator can illuminate or provide a visual indication when a first characteristic reaches a second threshold, and so on. The circumferential indicators 2022 can be color changing indicators. In some embodiments, the circumferential indicators 2022 can be LED indicators and one or more LED colors can be used. As illustrated in FIG. 23, the hand-held skin perfusion pressure determination device 2302 can have three circumferential indicators 2322.

Although, FIGS. 7A-7C, 7L-7O, 7R, 8, 9A-9B, 11, and 17B illustrate a square, rectangular, substantially rectangular, or substantially rectangular dressing with lobes, in some embodiments, various dressing shapes and sizes can be used.

In some embodiments, the dressing can be rectangular, square, round, oval, rounded rectangle, triangular, and/or any other shape. In some embodiments, multi-lobe dressings can be used. For example, quadrilobe, trilobe, and/or sacral dressings such as dressings available for ALLEVYN™ or ALLEVYN Life™ product line available from Smith & Nephew can be used with the embodiments described herein. In some embodiments, the dressing can include an asymmetrical lobed or notched dressing with no line of symmetry so that the measurement device can determine the orientation.

It will be appreciated that the blood perfusion sensor may comprise other types of optical sensor or may be a non-optical sensor, the monitoring device could comprise other types of data storage devices. It will also be appreciated that, where applicable, each embodiment described previously could be modified so that recorded data is processed and/or stored locally on a skin perfusion pressure determination device or transmitted for remote processing and/or storage and vice versa.

The embodiments described above comprise a sensor module which is configured such that an optical sensor can be positioned adjacent the skin and a force sensor is located above the optical sensor. Other possible arrangements include a sensor module in which a force sensor and an optical sensor are arranged such that, in use, the force sensor is placed next to a target region of skin tissue and the optical sensor is positioned above the force sensor. In such an arrangement, the force sensor may comprise through-holes or transparent portions through which light can be transmitted.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sternotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma and venous ulcers or the like.

It will be understood that embodiments of the present disclosure are generally applicable for use in topical negative pressure ("TNP") therapy systems, such as be incorporated into a TNP dressing. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg. The negative pressure range for some embodiments of the present disclosure can be approximately −80 mmHg, or between about −20 mmHg and −200 mmHg. Note that these pressures are relative to normal ambient atmospheric pressure, which can be 760 mmHg. Thus, −200 mmHg would be about 560 mmHg in practical terms. In some embodiments, the pressure range can be between about −40 mmHg and −150 mmHg. Alternatively a pressure range of up to −75 mmHg, up to −80 mmHg or over −80 mmHg can be used. Also in other embodiments a pressure range of below −75 mmHg can be used. Alternatively, a pressure range of over approximately −100 mmHg, or even −150 mmHg, can be supplied by the negative pressure apparatus.

In the drawings like reference numerals refer to like parts.

Throughout the description and claims of this specification, the words "comprise" and "contain" and variations of them mean "including but not limited to" and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics or groups described in conjunction with a particular aspect, embodiment or example of the disclosure are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of the features and/or steps are mutually exclusive. The disclosure is not restricted to any details of any foregoing embodiments. The disclosure extends to any novel one, or novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

What is claimed is:

1. A skin perfusion pressure determination device comprising:
    an elongate probe comprising a distal end, a grip portion, and a sensor module comprising a first sensor for sensing a first parameter associated with a pressure exerted on a target area by the sensor module and a second sensor for sensing a second parameter associated with an amount of blood perfusion at the target area, wherein the first sensor and the second sensor are arranged such that, when the distal end is pressed against the target area the first sensor produces an output corresponding to the sensed first parameter and the second sensor produces an output corresponding to the sensed second parameter;
    wherein the first sensor comprises a force sensor arranged to determine the force exerted by the sensor module on the target area, such that when the distal end is pressed against the target area, the second sensor is disposed between the target area and the force sensor, and
    wherein the grip portion is configured to be held by a user to press the distal end against the target area.

2. The skin perfusion pressure determination device of claim 1, wherein the second sensor comprises a light source and an optical detector arranged to receive light emitted by the light source which has been reflected by the target area.

3. The skin perfusion pressure determination device of claim 2, wherein the light source comprises at least one light emitting diode and the optical detector comprises at least one photodetector.

4. The skin perfusion pressure determination device of claim 1, wherein the second sensor is a pulse sensor.

5. The skin perfusion pressure determination device of claim 1, wherein the device is a portable device.

6. The skin perfusion pressure determination device of claim 1, wherein the distal end further comprises a pad comprising a lower surface configured to be pressed against the target area.

7. The skin perfusion pressure determination device of claim 1, further comprising a processor for processing an output of the first sensor and an output of the second sensor, wherein the processor is configured to determine that the output of the second sensor satisfies a predetermined condition associated with a predetermined amount of blood perfusion at the target area.

8. The skin perfusion pressure determination device of claim 7, wherein the predetermined condition is a condition which corresponds to an amount of blood perfusion at the target area which exceeds a predetermine threshold.

9. The skin perfusion pressure determination device of claim 7, wherein the predetermined condition is a condition that corresponds to the presence of a pulsatile component of blood flow at the target area.

10. The skin perfusion pressure determination device of claim 7, wherein the processor is further configured to produce an output which represents a pressure exerted on the target area by the sensor module when the second parameter satisfies the predetermined condition.

11. The skin perfusion pressure determination device of claim 7, further comprising a memory for storing at least one of the predetermined condition and the output of the processor.

12. Apparatus comprising the skin perfusion pressure determination device of claim 1, wherein the apparatus comprises a display for displaying information representing at least one output of the first sensor and the second sensor.

13. An apparatus comprising:
    a wound dressing;
    a skin perfusion pressure determination device comprising an elongate probe portion comprising a distal tip, a hand grip portion, and a sensor module, the sensor module comprising a sensor configured to sense at least one characteristic associated with a wound or a region of tissue proximate to a wound and a force sensor arranged to determine the force exerted by the sensor module on the wound or the region of tissue, wherein the sensor is disposed between the distal tip and the force sensor; and a display configured to indicate at least one condition relating to the at least one characteristic associated with the wound or the region of tissue proximate to the wound sensed by the sensor module.

14. An apparatus comprising:
a wound dressing;
a skin perfusion pressure determination device comprising an elongate probe portion comprising a hand grip, a distal end, a contact section at the distal end, and a sensor module, the sensor module comprising a sensor configured to sense at least one characteristic associated with a wound or a region of tissue proximate to a wound and a force sensor arranged to determine the force exerted by the sensor module on the wound or the region of tissue, wherein the sensor is disposed between the wound or the region of tissue and the force sensor; and
an audible and/or tactile indicator configured to indicate at least one condition relating to the at least one characteristic associated with a wound or a region of tissue proximate to a wound sensed by the sensor module.

15. The apparatus of claim 14, wherein the contact section further comprises a pad comprising a lower surface configured to be pressed against a portion of the wound dressing.

16. A method of determining at least one characteristic associated with a wound or a region of tissue proximate to a wound comprising:
locating a wound dressing comprising a wound protecting portion over a wound whereby the wound protecting portion overlies the wound;
gripping a skin perfusion pressure determination device comprising an elongate probe portion comprising a hand grip portion and a sensor module;
positioning the skin perfusion pressure determination device at a target area on or adjacent to the wound dressing, wherein the sensor module comprises a sensor configured to detect at least one characteristic associated with a wound or a region of tissue proximate to a wound and a force sensor arranged to determine the force exerted by the sensor module on the target area, wherein the sensor is disposed between the target area and the force sensor; and
receiving a visual, audible, or tactile indicator relating to the at least one characteristic associated with a wound or a region of tissue proximate to a wound detected with the sensor of the skin perfusion pressure determination device.

17. The method of claim 16, further comprising processing an output of the sensor and an output of the force sensor and determining that the output of the force sensor satisfies a predetermined condition associated with a predetermined amount of blood perfusion at the target area.

18. The method of claim 17, wherein the predetermined condition is a condition which corresponds to an amount of blood perfusion at the target area which exceeds a predetermine threshold.

19. The method of claim 17, wherein the predetermined condition is a condition that corresponds to the presence of a pulsatile component of blood flow at the target area.

20. The method of claim 17, further comprising producing an output which represents a pressure exerted on the target area by the sensor module when the second parameter satisfies the predetermined condition.

* * * * *

UNITED STATES PATENT AND TRADEMARK OFFICE
CERTIFICATE OF CORRECTION

| | | |
|---|---|---|
| PATENT NO. | : 12,178,597 B2 | Page 1 of 1 |
| APPLICATION NO. | : 16/492531 | |
| DATED | : December 31, 2024 | |
| INVENTOR(S) | : Brownhill et al. | |

It is certified that error appears in the above-identified patent and that said Letters Patent is hereby corrected as shown below:

On the Title Page

Column 1, Page 4 (U.S. Patent Documents), Line 35, delete "Cemasov et al." and insert -- Cernasov et al. --.

Column 2, Page 4 (Foreign Patent Documents), Line 51, delete "WVO 2015/112095." and insert -- WO 2015/112095 --.

Signed and Sealed this
Twenty-ninth Day of April, 2025

Coke Morgan Stewart
*Acting Director of the United States Patent and Trademark Office*